(12) United States Patent
Hyun

(10) Patent No.: US 11,338,004 B2
(45) Date of Patent: May 24, 2022

(54) COMPOSITION FOR PREVENTING OR TREATING CRANIAL NERVE DISEASE COMPRISING FOMES FOMENTARIUS EXTRACT, FRACTION THEREOF, OR COMPOUND ISOLATED THEREFROM AS ACTIVE INGREDIENT

(71) Applicant: DONG-EUI UNIVERSITY INDUSTRIAL-ACADEMIC COOPERATION FOUNDATION, Busan (KR)

(72) Inventor: Kyung-Yae Hyun, Busan (KR)

(73) Assignee: DONG-EUI UNIVERSITY INDUSTRIAL-ACADEMIC COOPERATION FOUNDATION, Busan (KR)

( * ) Notice: Subject to any disclaimer, the term of this patent is extended or adjusted under 35 U.S.C. 154(b) by 715 days.

(21) Appl. No.: 15/761,969

(22) PCT Filed: Sep. 22, 2016

(86) PCT No.: PCT/KR2016/010583
§ 371 (c)(1),
(2) Date: Mar. 21, 2018

(87) PCT Pub. No.: WO2017/052227
PCT Pub. Date: Mar. 30, 2017

(65) Prior Publication Data
US 2018/0289758 A1  Oct. 11, 2018

(30) Foreign Application Priority Data

Sep. 22, 2015 (KR) .................. 10-2015-0133767
Nov. 26, 2015 (KR) .................. 10-2015-0166540
Nov. 26, 2015 (KR) .................. 10-2015-0166549
Nov. 26, 2015 (KR) .................. 10-2015-0166552

(51) Int. Cl.
| | | |
|---|---|---|
| *A61K 36/07* | (2006.01) | |
| *A61K 36/30* | (2006.01) | |
| *A61K 36/72* | (2006.01) | |
| *A61K 36/20* | (2006.01) | |
| *A23L 33/105* | (2016.01) | |
| *A23L 33/10* | (2016.01) | |
| *A23L 31/00* | (2016.01) | |
| *A61P 25/28* | (2006.01) | |
| *A61K 36/77* | (2006.01) | |

(52) U.S. Cl.
CPC .............. *A61K 36/07* (2013.01); *A23L 31/00* (2016.08); *A23L 33/10* (2016.08); *A23L 33/105* (2016.08); *A61K 36/20* (2013.01); *A61K 36/30* (2013.01); *A61K 36/72* (2013.01); *A61K 36/77* (2013.01); *A61P 25/28* (2018.01); *A23V 2002/00* (2013.01); *A61K 2236/00* (2013.01)

(58) Field of Classification Search
None
See application file for complete search history.

(56) References Cited

FOREIGN PATENT DOCUMENTS

| CN | 104305180 A | * | 1/2015 |
|---|---|---|---|
| JP | 2000-351710 A | | 12/2000 |
| KR | 10-2007-0048673 A | | 5/2007 |
| KR | 2009078703 A | * | 7/2009 |
| KR | 10-2013-0039561 A | | 4/2013 |
| KR | 10-2013-0140338 A | | 12/2013 |

OTHER PUBLICATIONS

Byers et al., Depression and Risk of Developing Dementia, 2012, Nat Rev Neurol, 7: 323-331.*
Donggurami, "Effect and Taking Method of Fomes fomentarius-," Sep. 1, 2015, inner pp. 1-5 <URL: http://blog.naver.com/qndjqskfk/22046997552>. See p. 2.
Zhang, Y. et al., Chemical Compositions and Antiproliferation Activities of the Chloroform Fraction from Pyropolyporus Fomentarius in K562 Cells, Human and Experimental Toxicology, [Electronic publishing], Nov. 17, 2014, vol. 34, No. 7, pp. 732-743. See abstract; table 1; figure 1.

* cited by examiner

*Primary Examiner* — Terry A McKelvey
*Assistant Examiner* — Catheryne Chen
(74) *Attorney, Agent, or Firm* — FisherBroyles, LLP; Joseph Hyosuk Kim

(57) ABSTRACT

The present disclosure relates to a pharmaceutical composition for preventing or treating a cranial nerve disease, comprising a *Fomes fomentarius* extract, a fraction thereof, or a compound isolated therefrom as an active ingredient. According to the present disclosure, the *Fomes fomentarius* extract is included as an active ingredient so that there are significant effects of inhibiting the production or expression of inflammatory cytokines and improving the activity of glucose metabolism in the brain to prevent or treat cranial nerve diseases, of lowering side effects on the human body as a natural product, and of being easily prepared and ingested.

10 Claims, 30 Drawing Sheets

[FIG. 1]
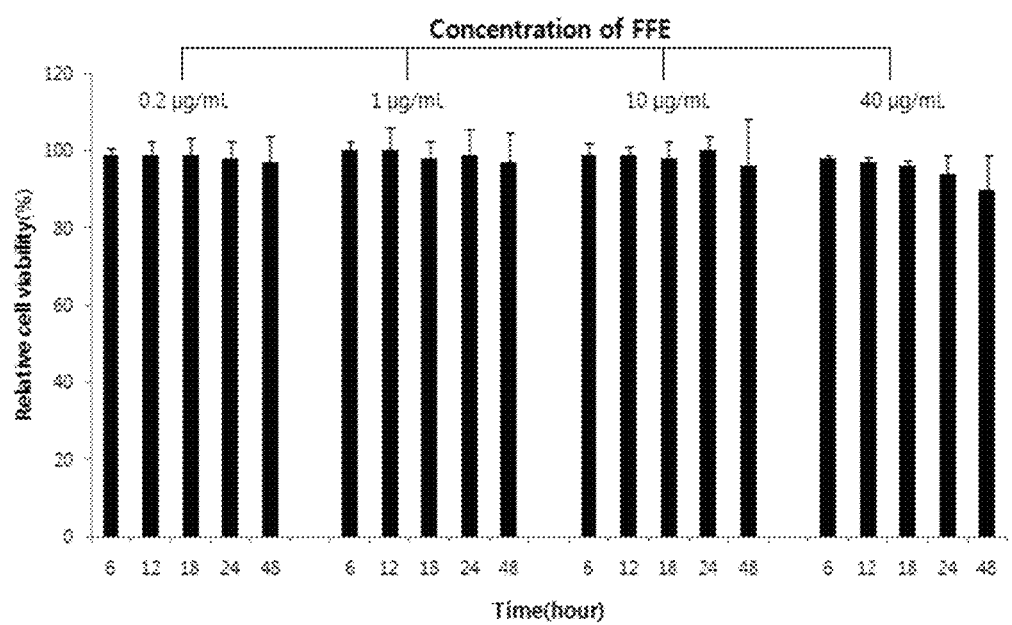

[FIG. 2a]
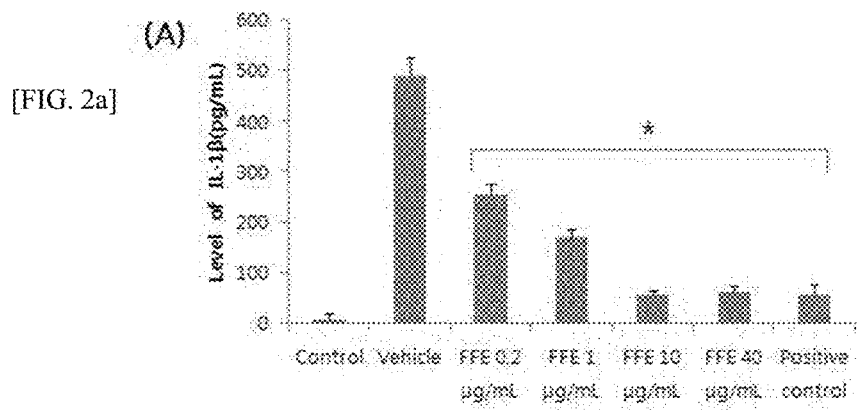
[FIG. 2b]
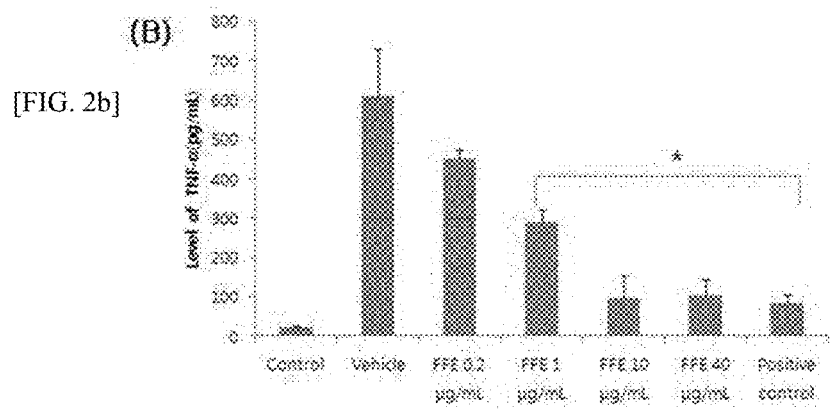
[FIG. 3]
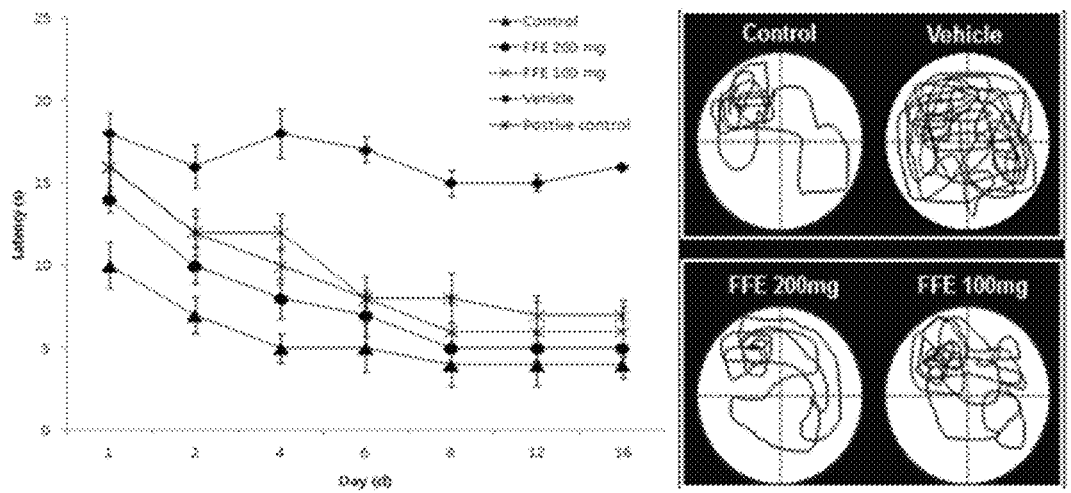

[FIG. 4]
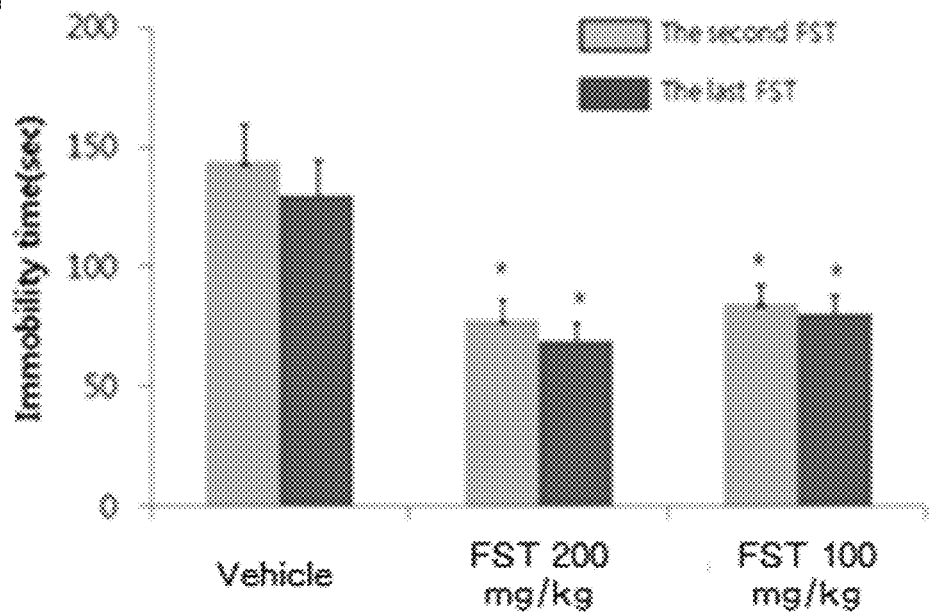
[FIG. 5a]
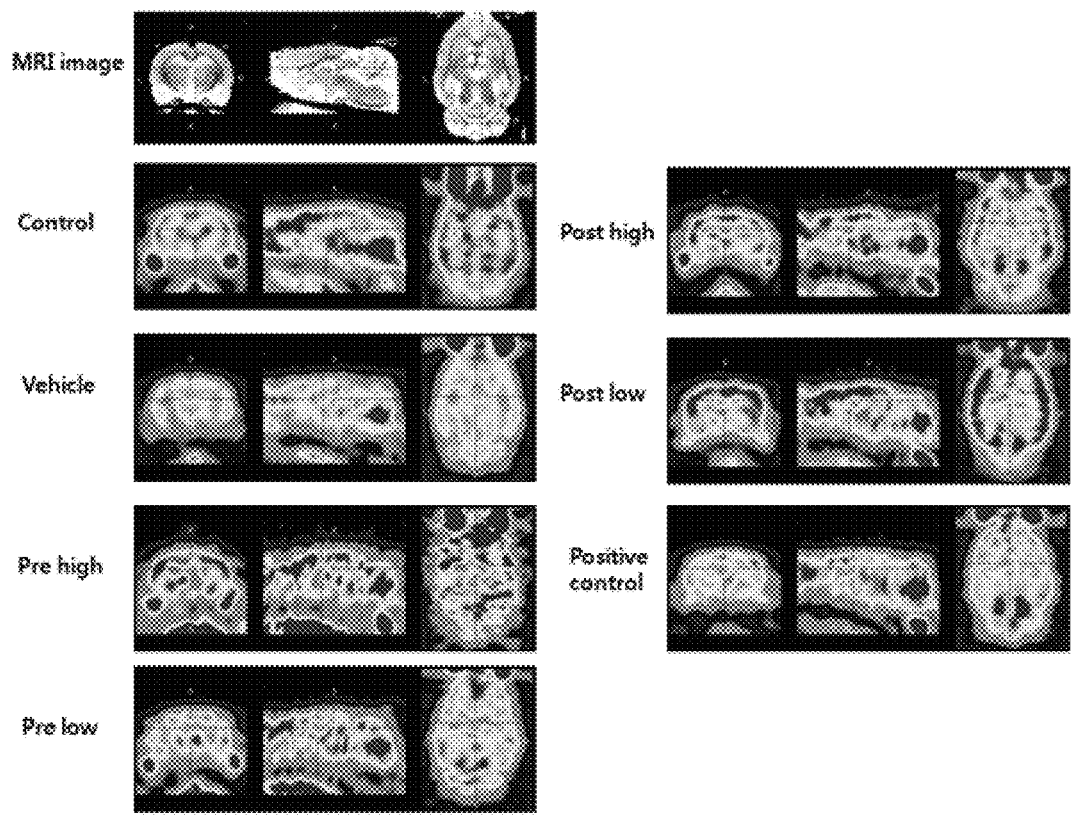

[FIG 5b]
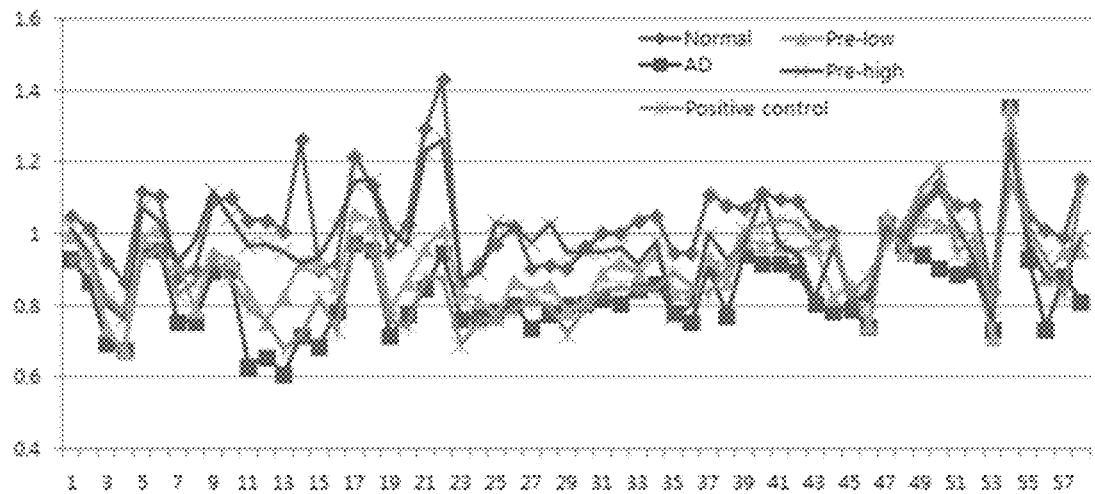
[FIG. 5c]
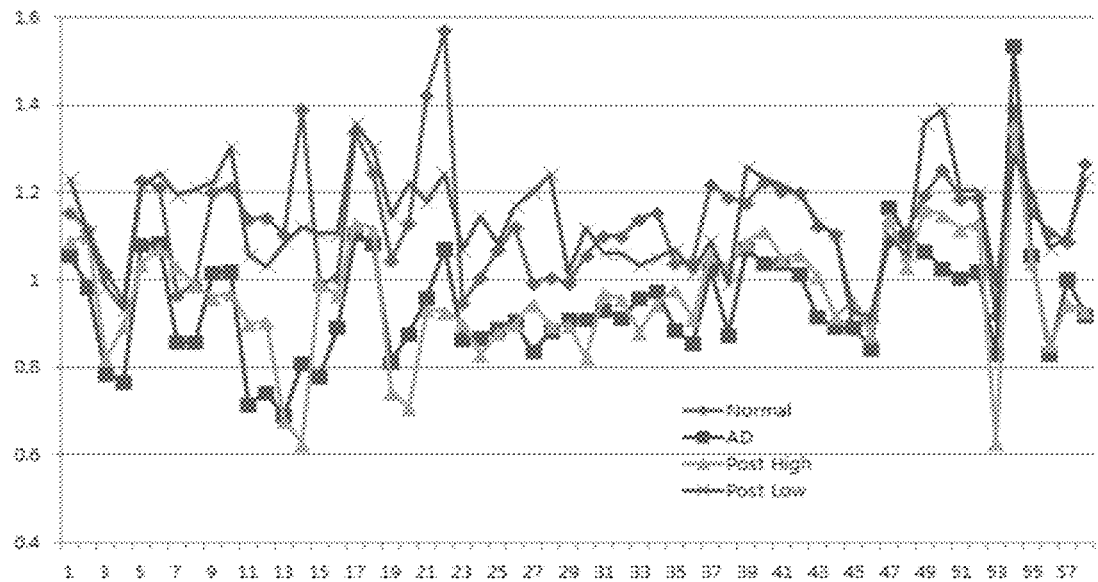

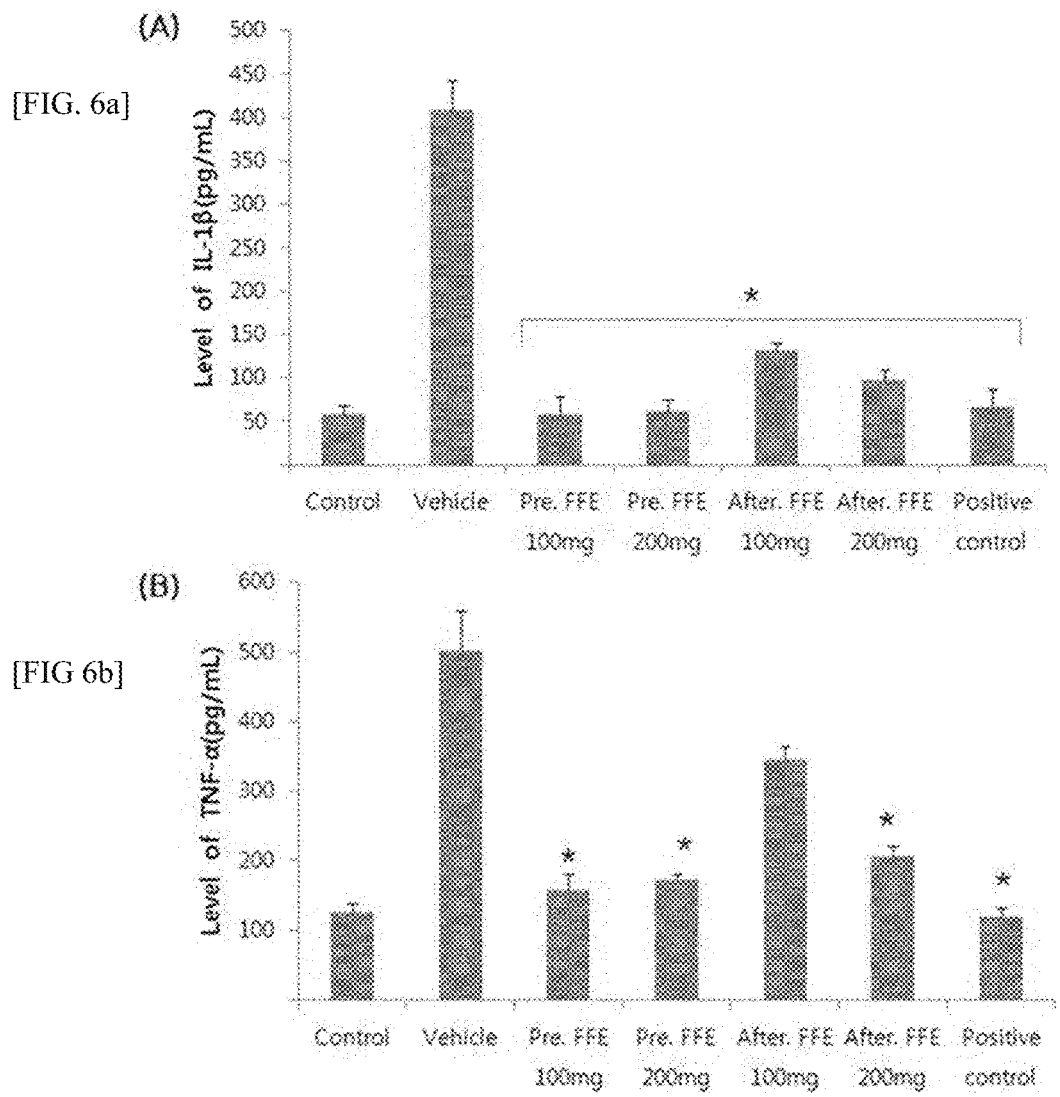
[FIG. 6a]
[FIG 6b]

[FIG. 7a]
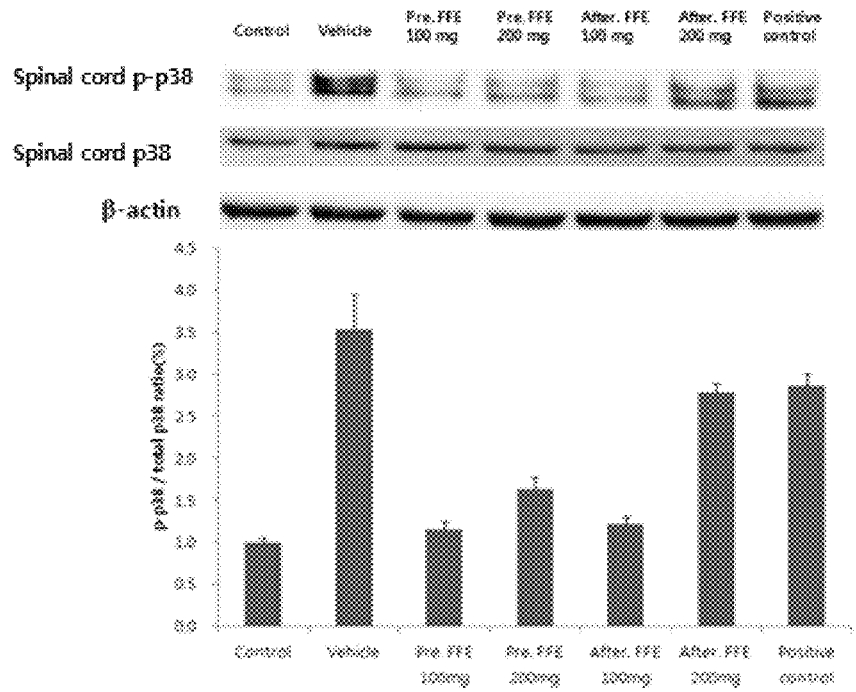
[FIG. 7b]
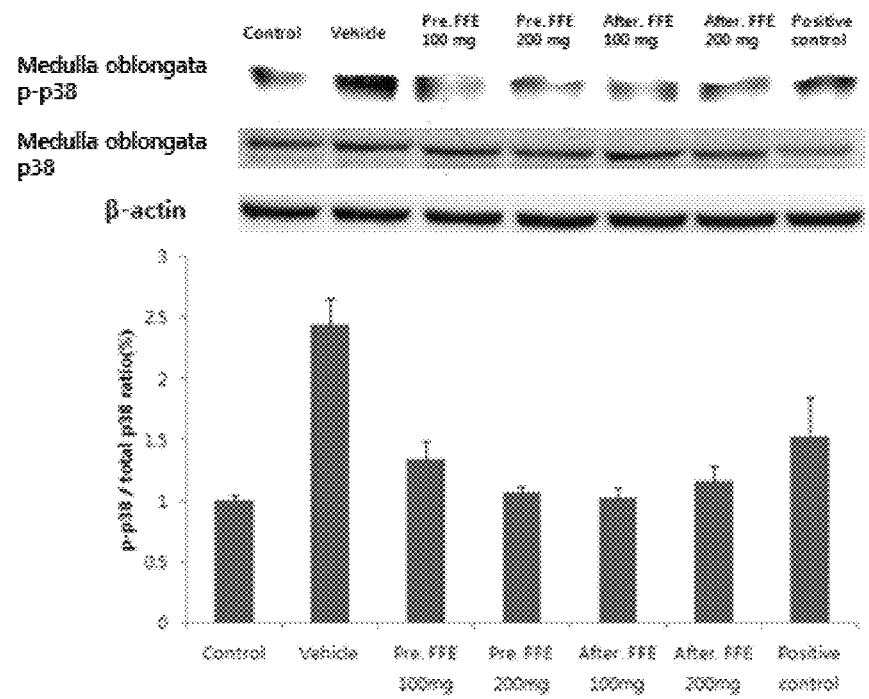

[FIG. 8a]
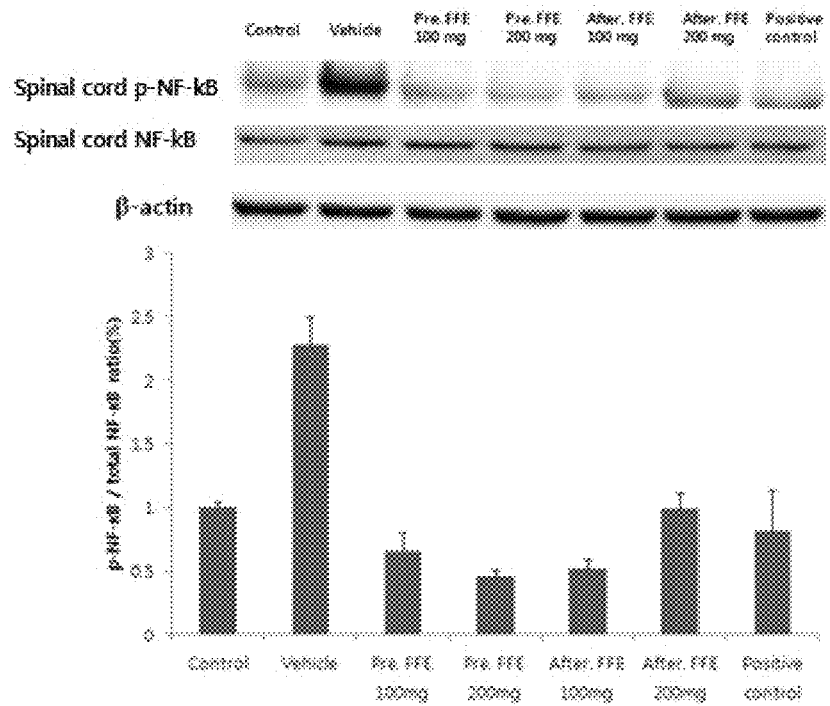
[FIG. 8b]
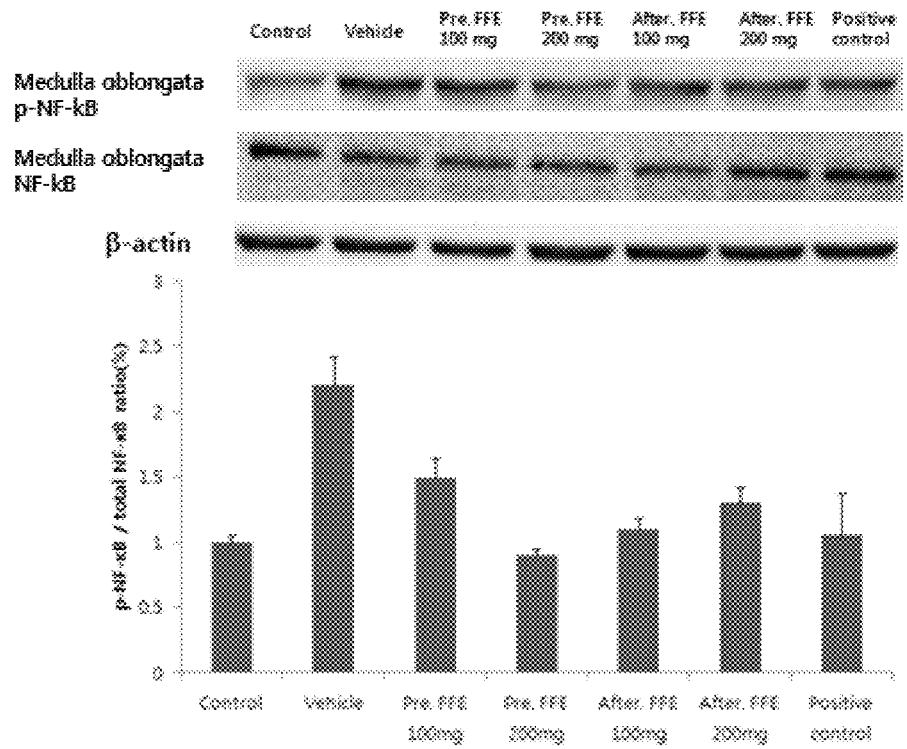

[FIG. 9]
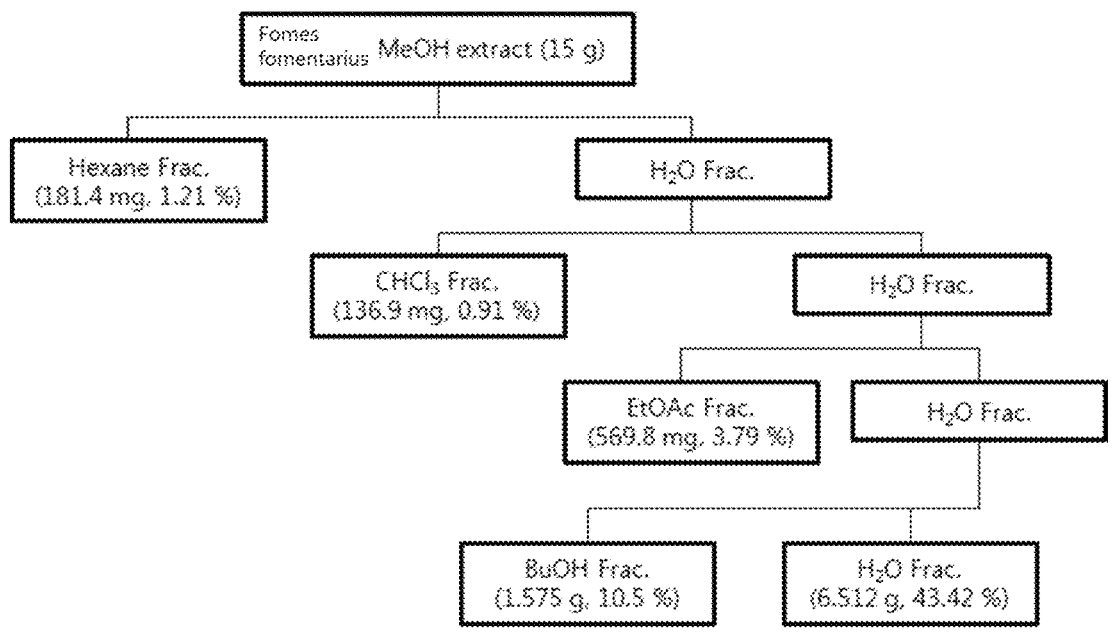
[FIG. 10]
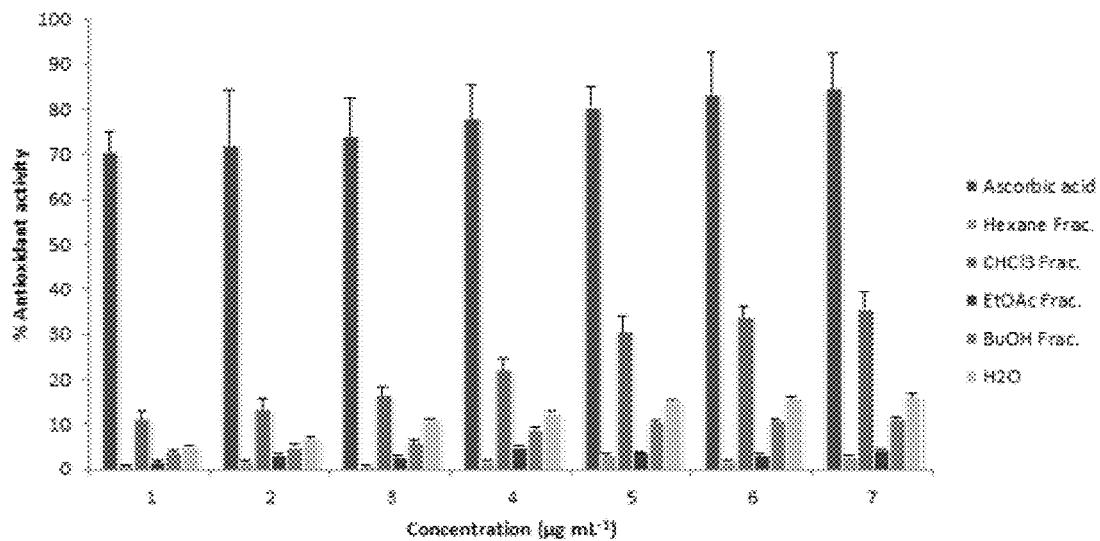

[FIG. 11]
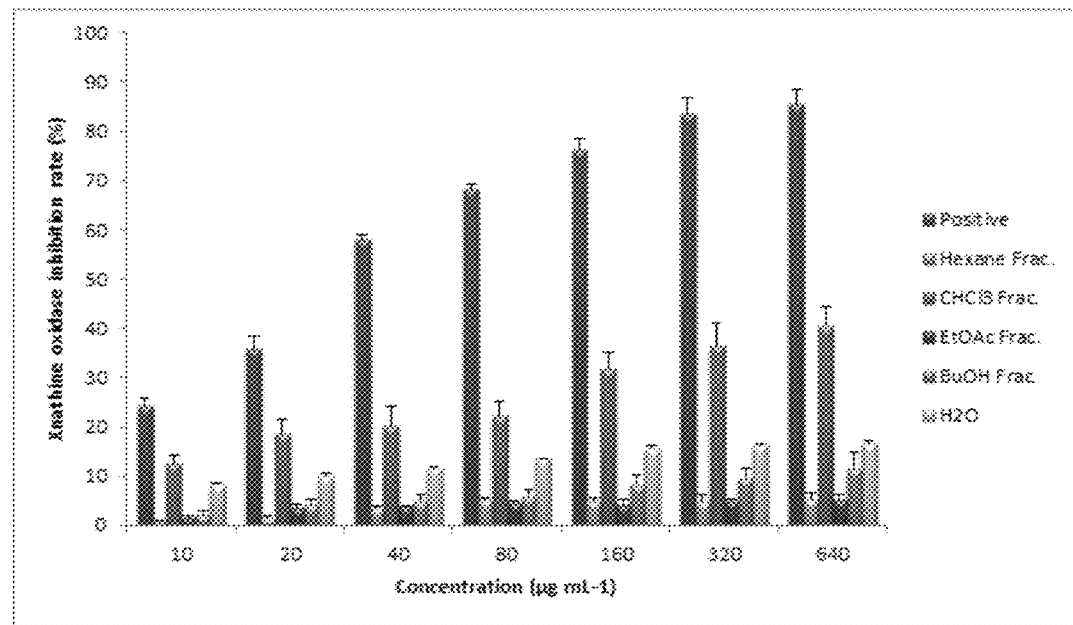
[FIG. 12]
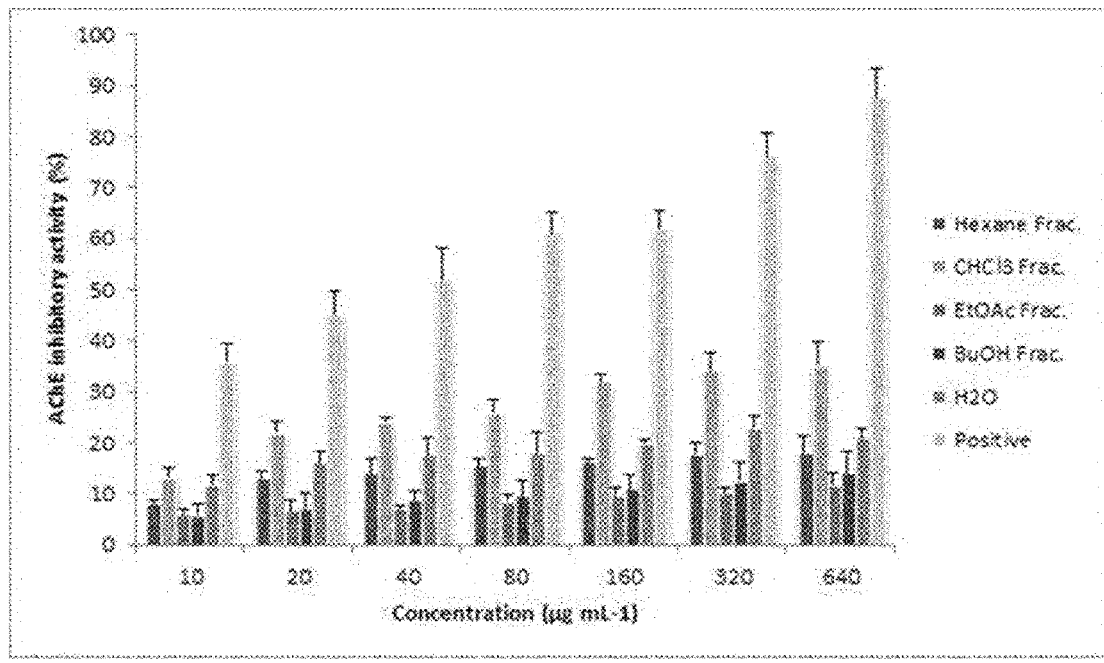

[FIG. 13]
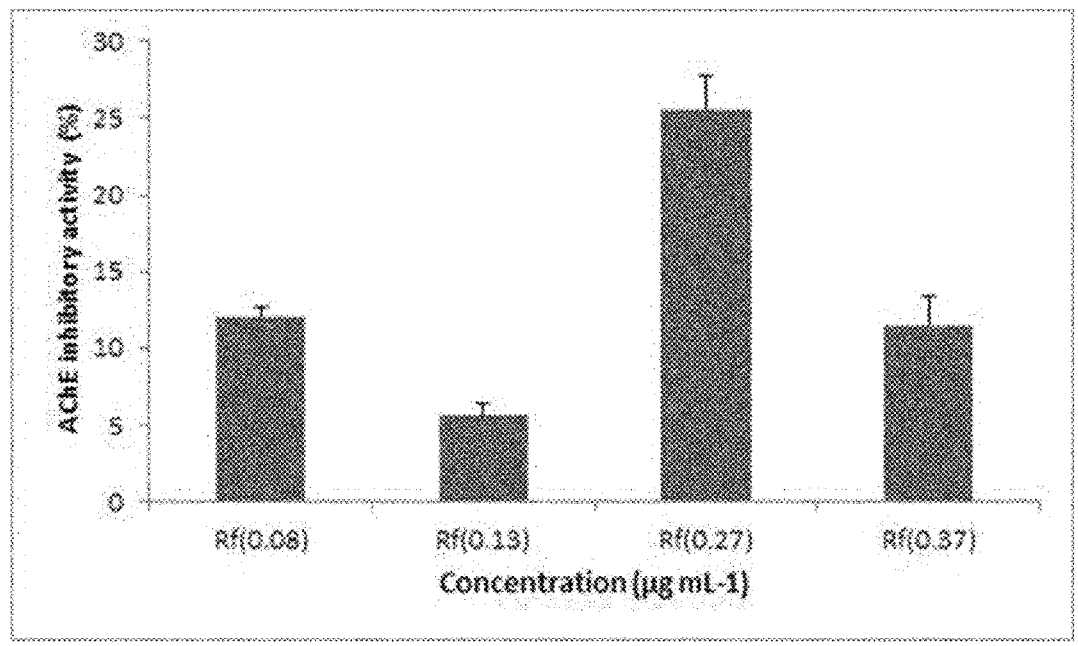
[FIG. 14]
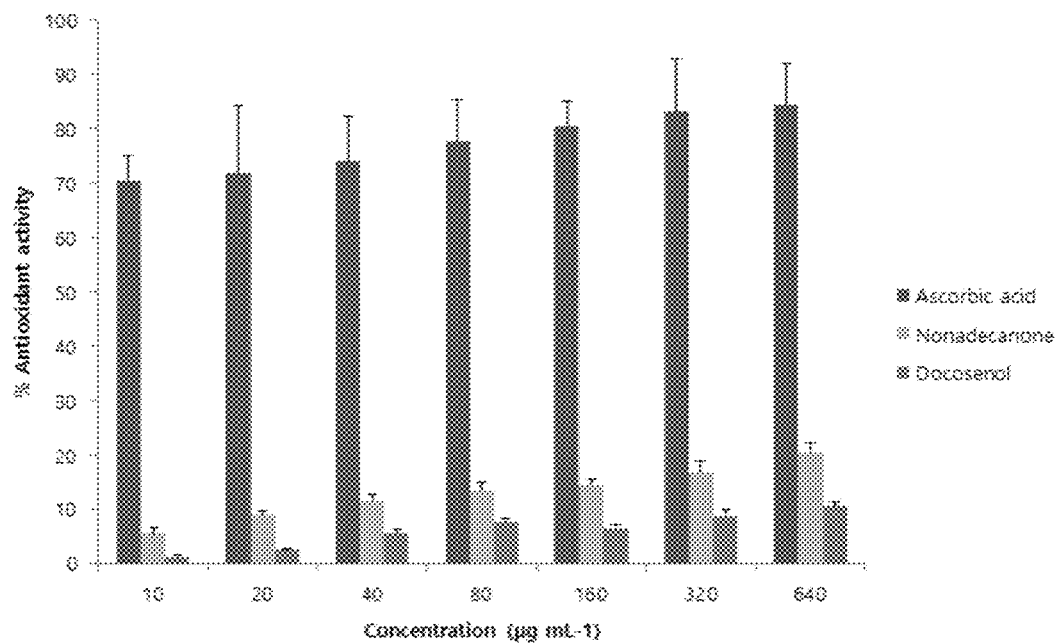

[FIG. 15]
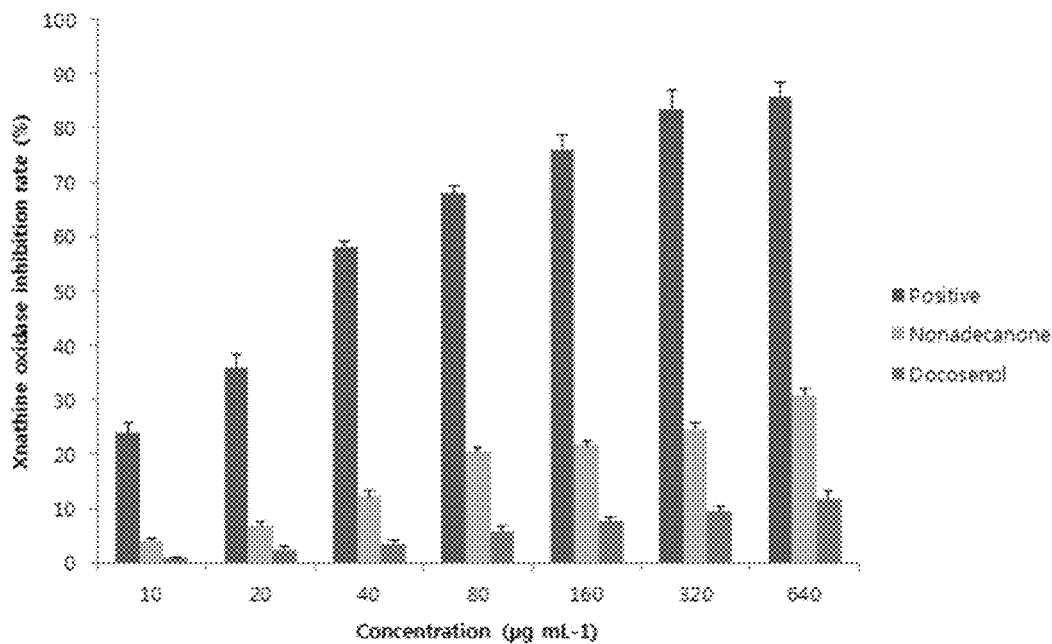
[FIG. 16]
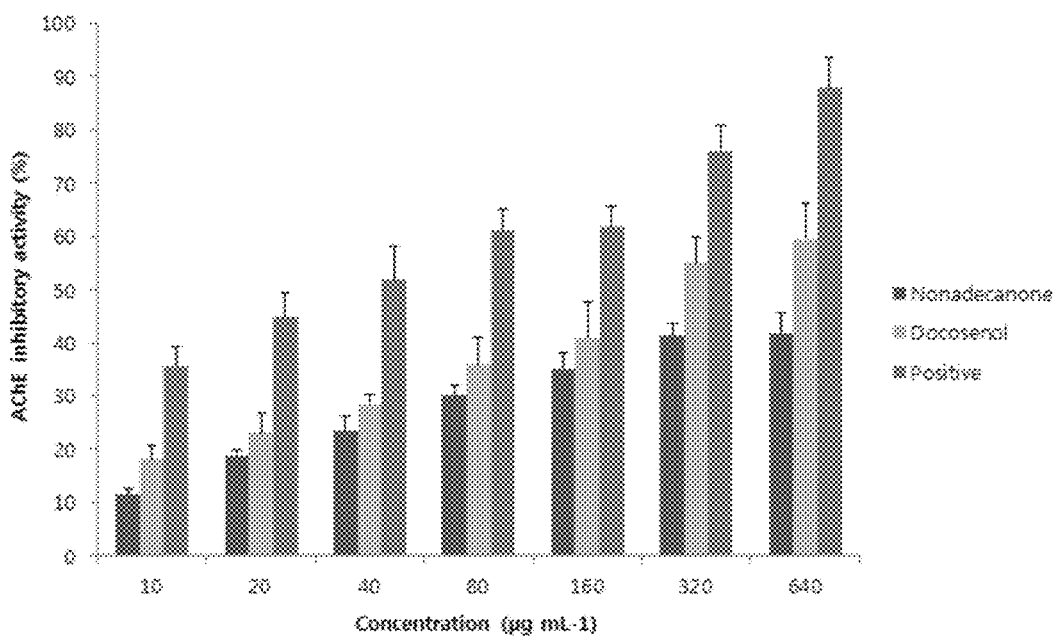

[FIG. 17]
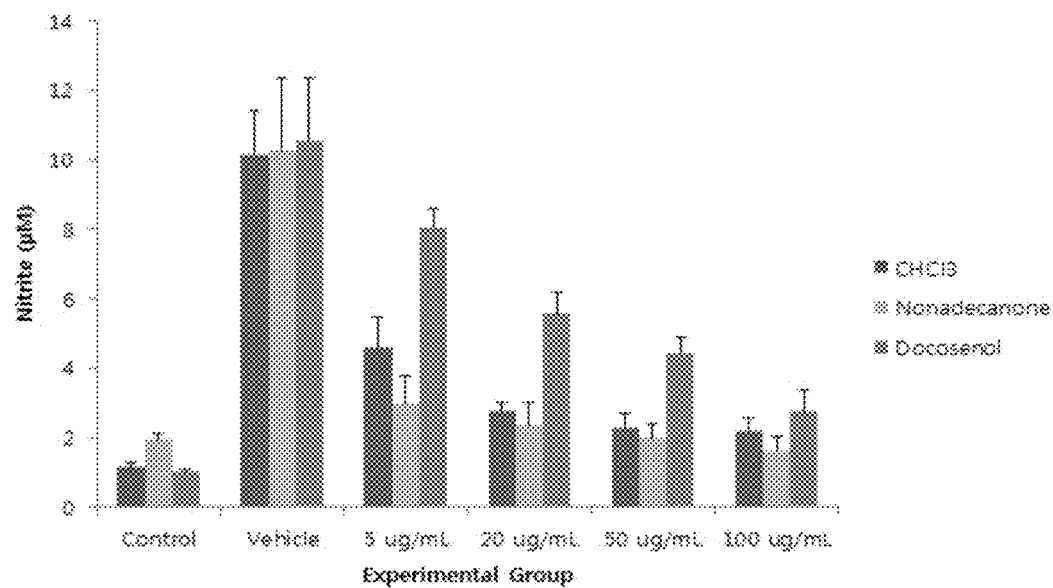
[FIG. 18]
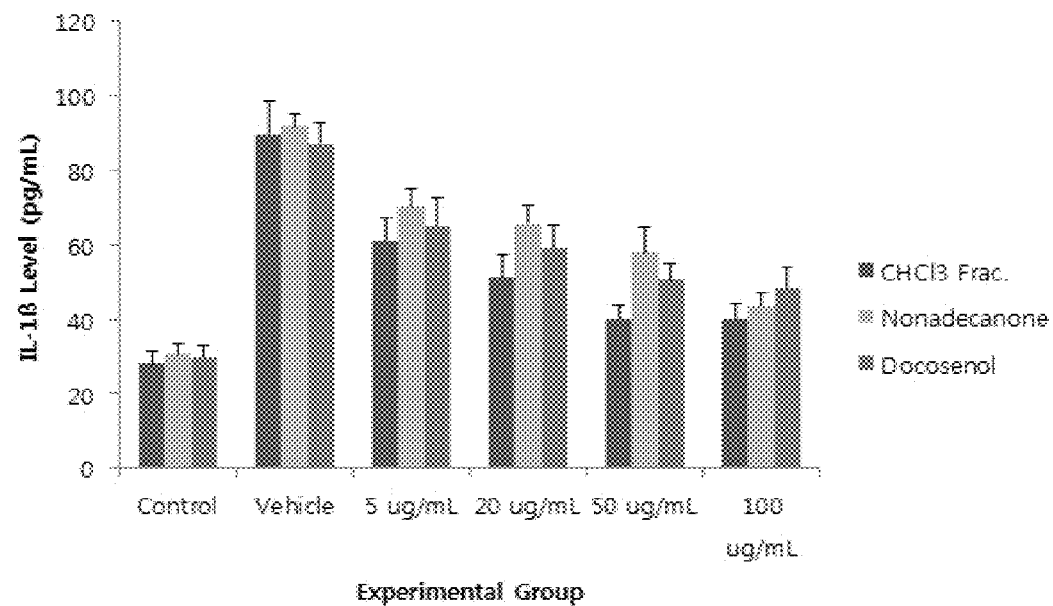

[FIG. 19]
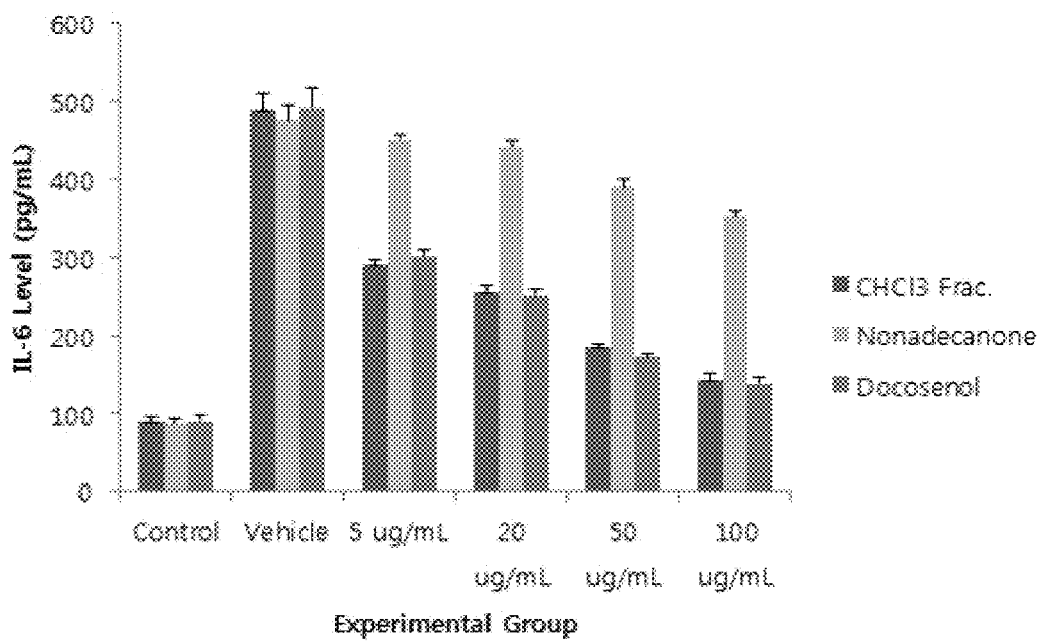
[FIG. 20]
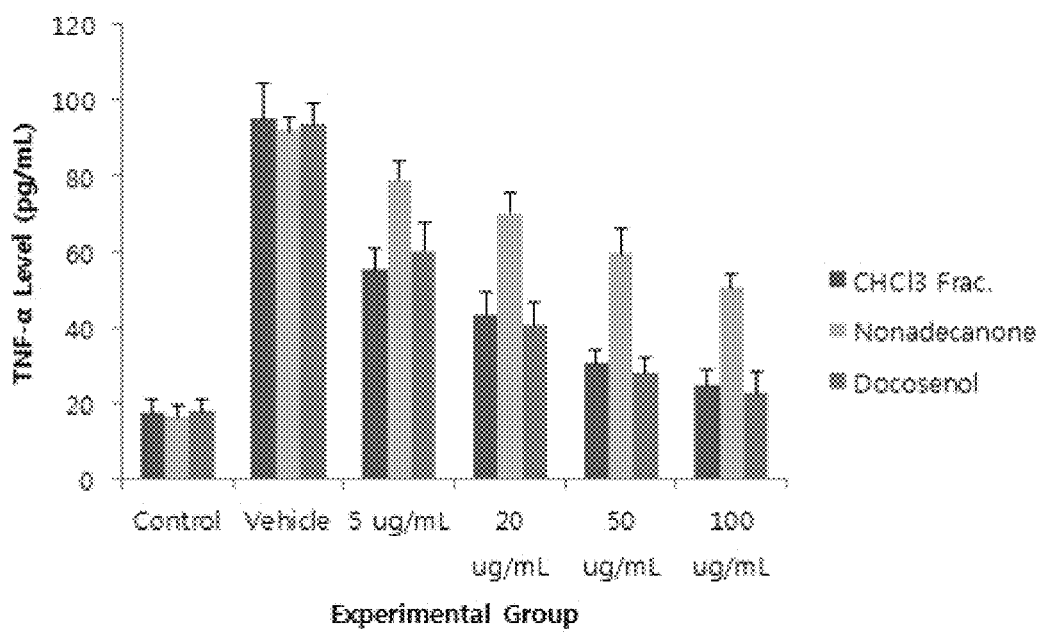

[FIG. 21]
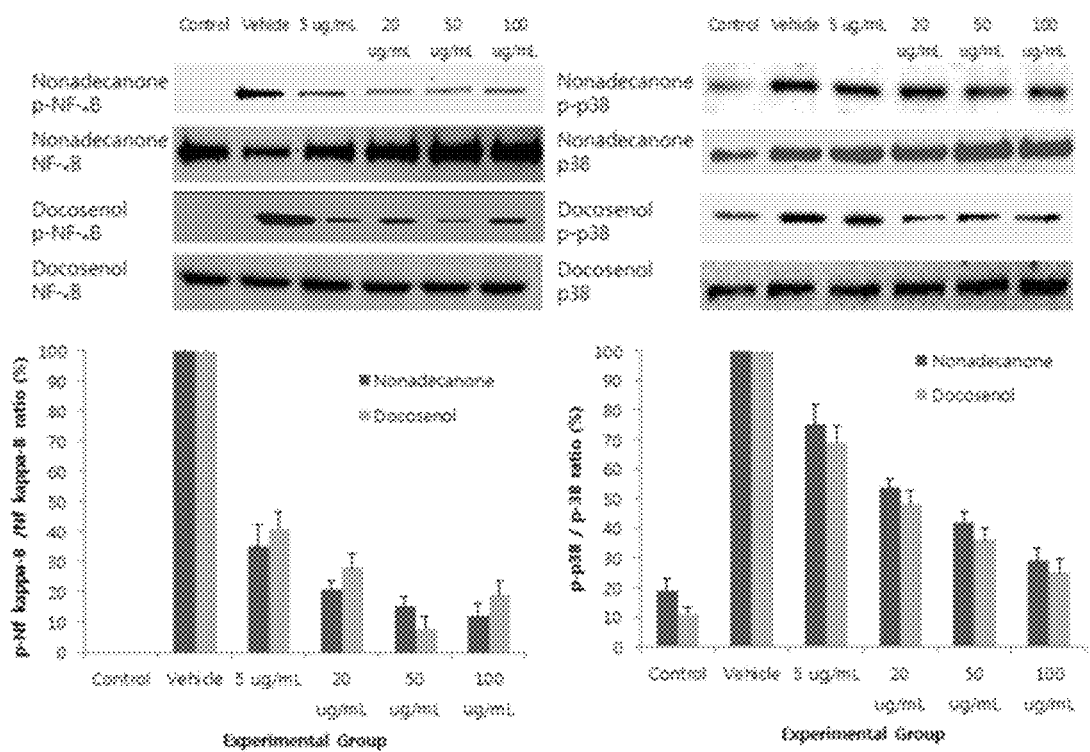
[FIG. 22]
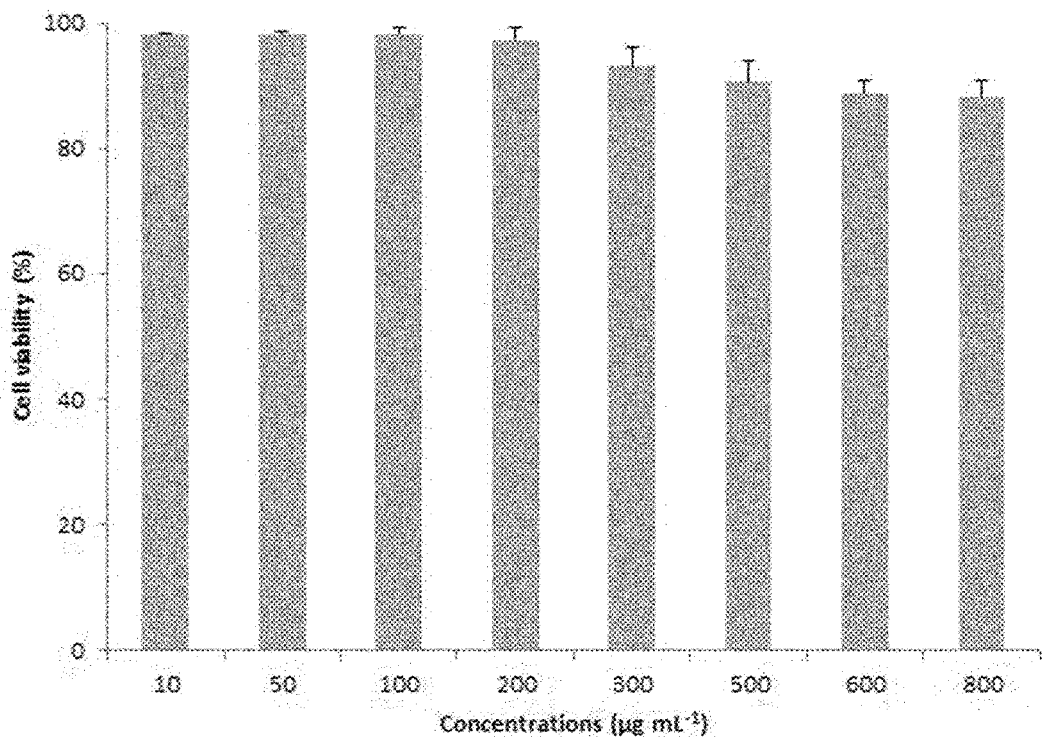

[FIG. 23]
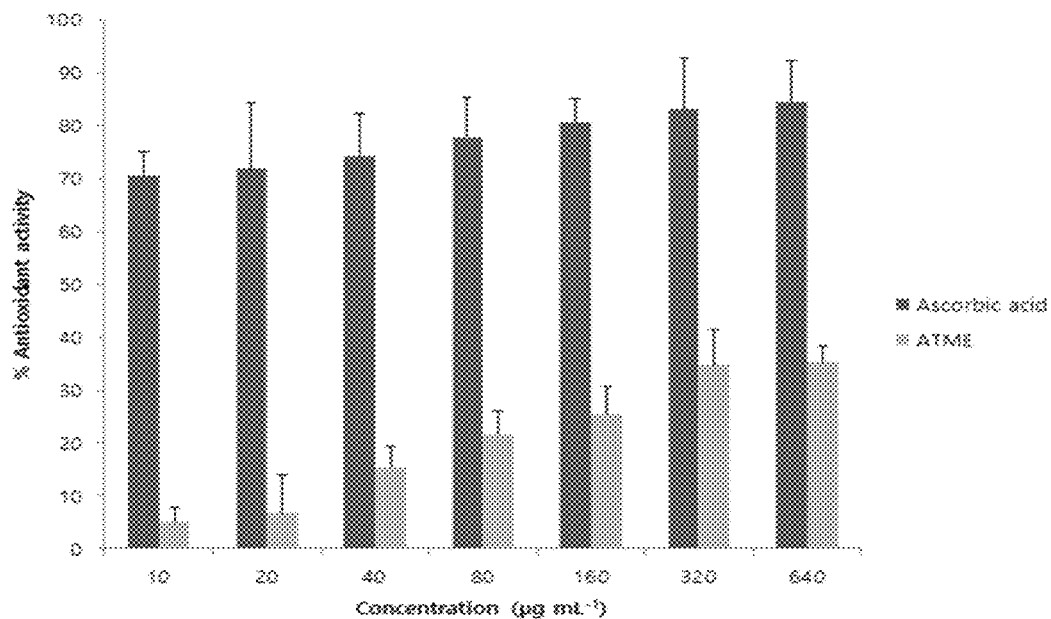
[FIG. 24]
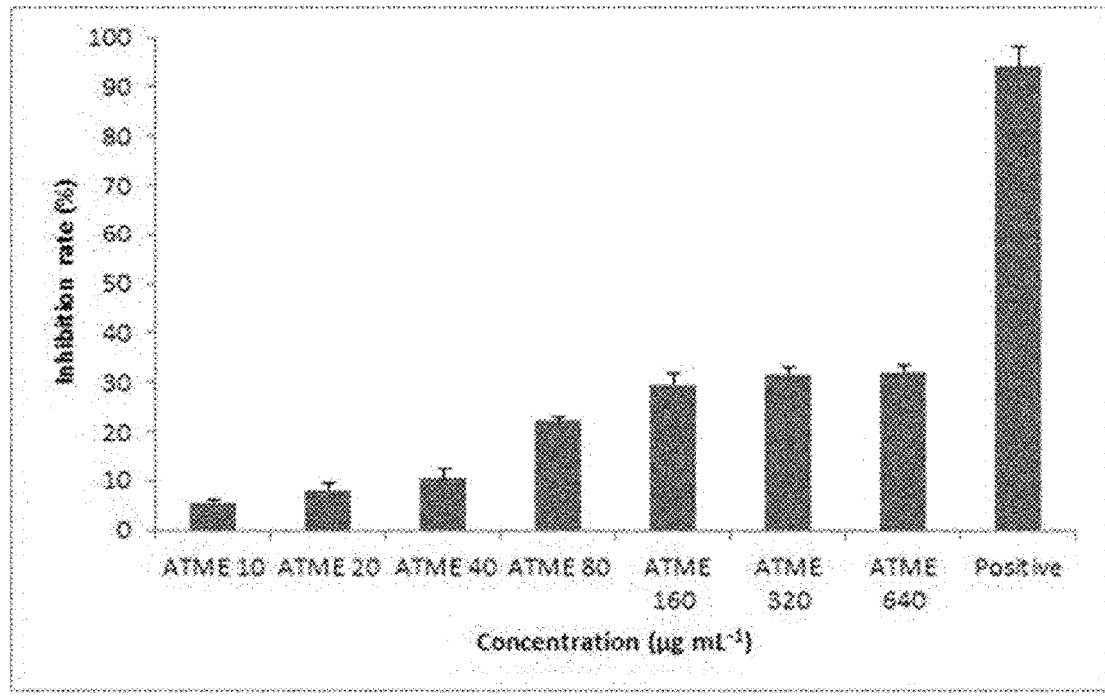

[FIG. 25]
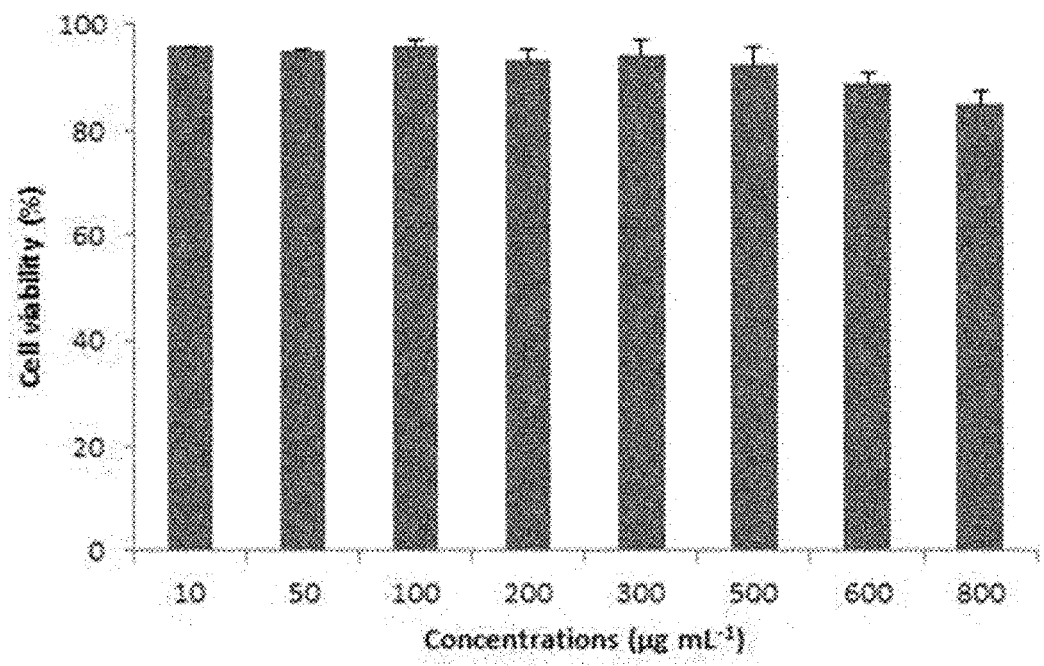
[FIG. 26]
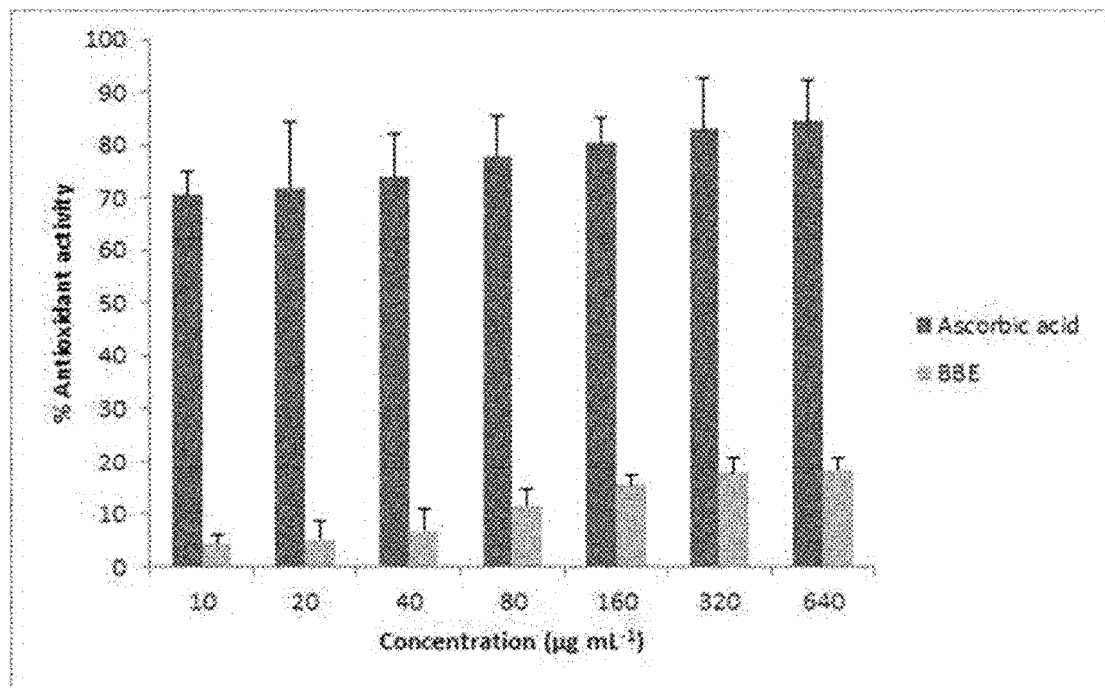

[FIG. 27]
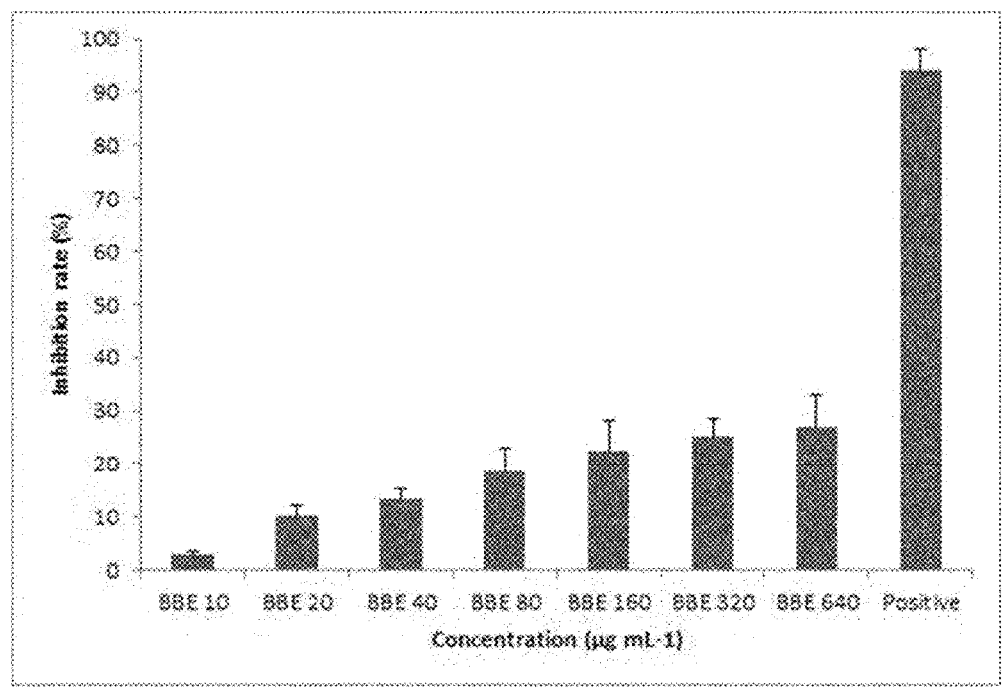
[FIG. 28]
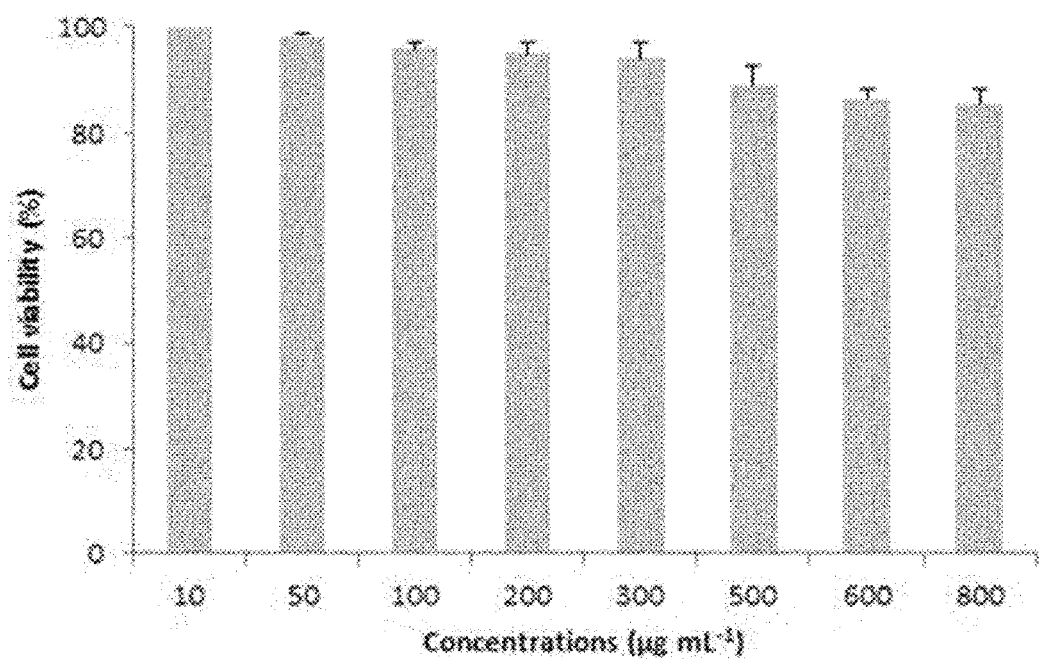

[FIG. 29]
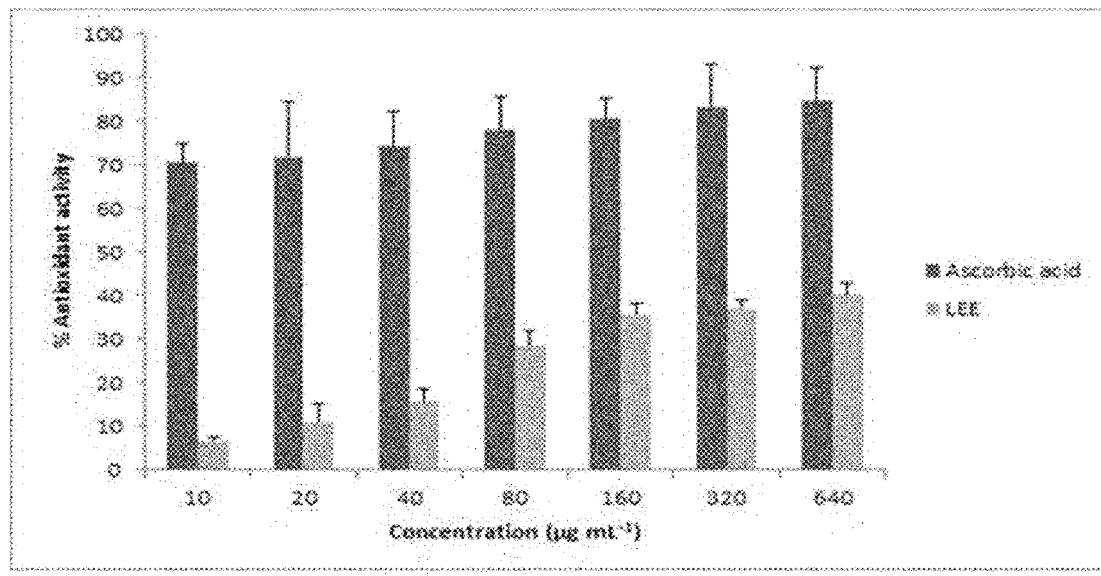
[FIG. 30]
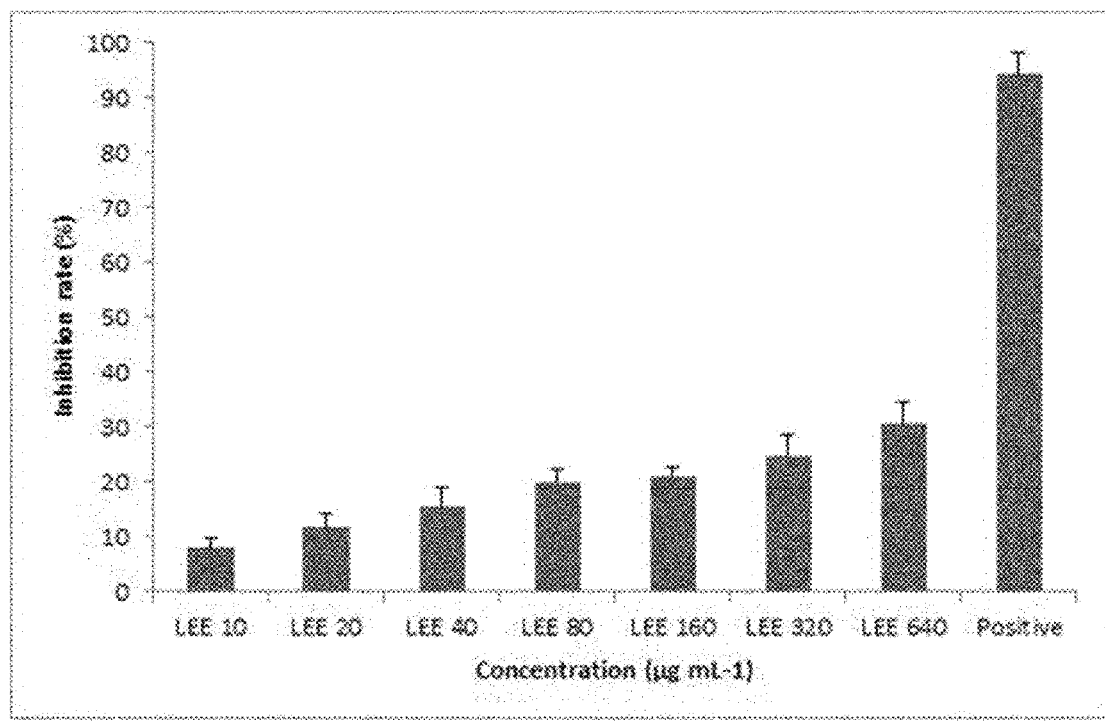

[FIG. 31]
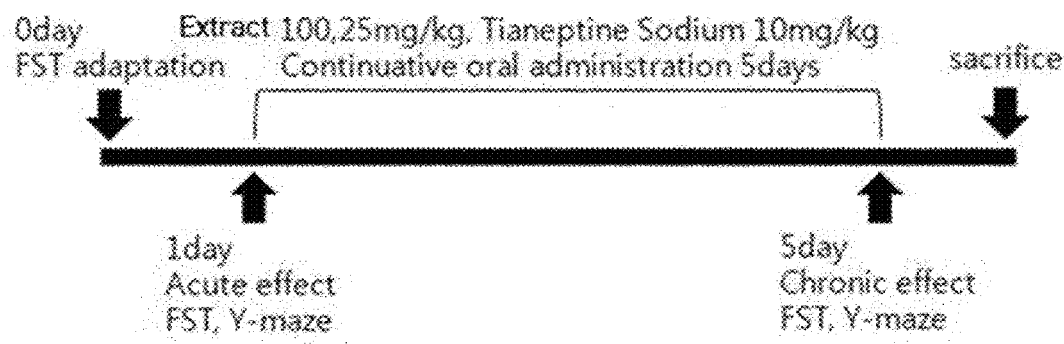
[FIG. 32]
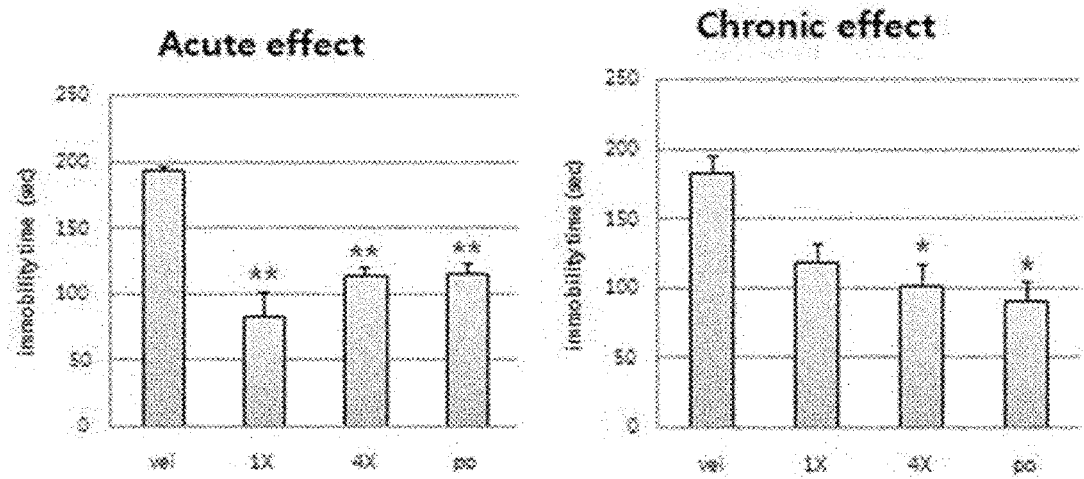

[FIG. 33]
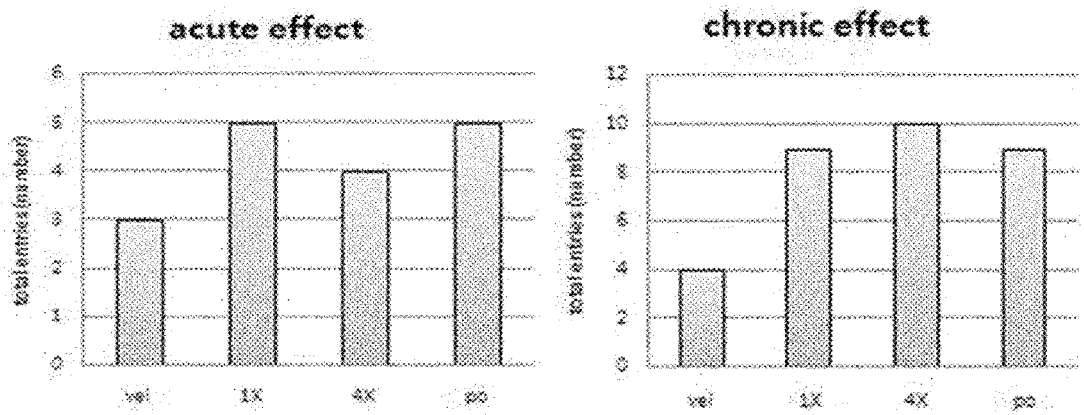
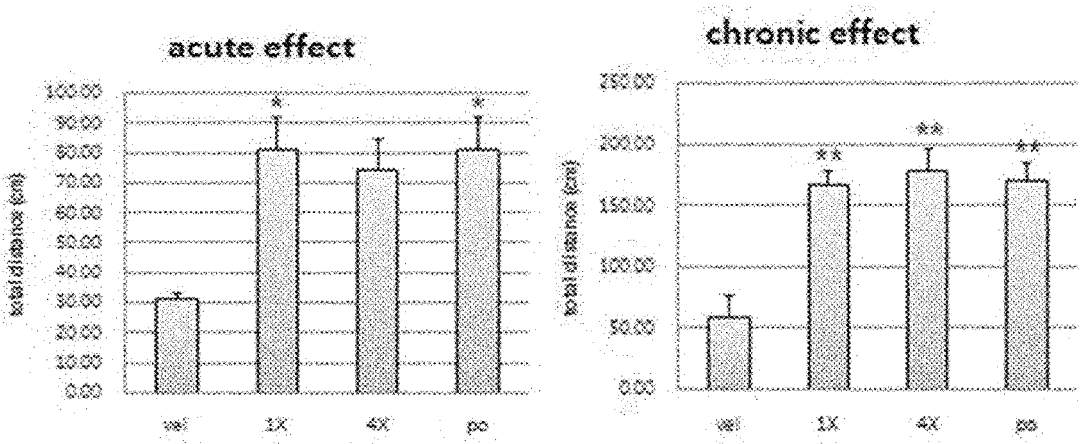
[FIG. 34]
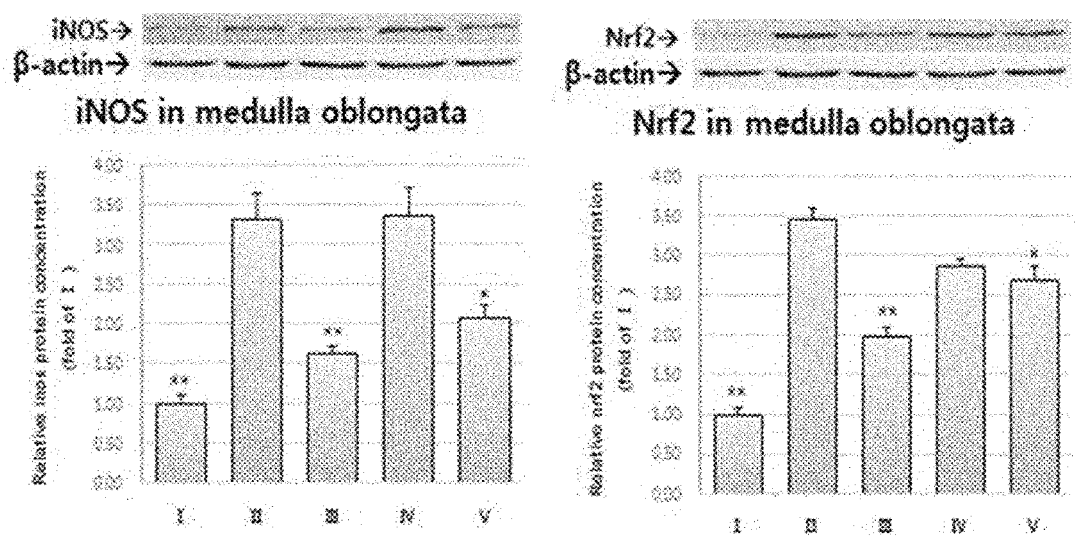

[FIG. 35]
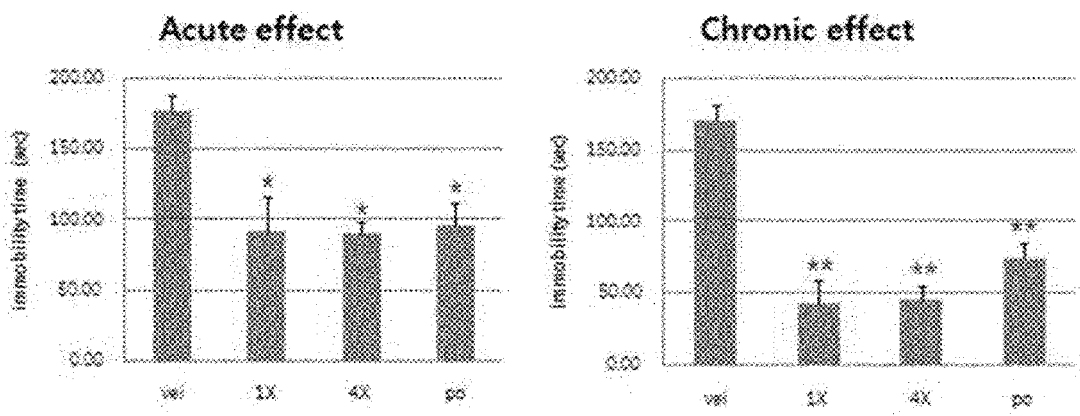
[FIG. 36]
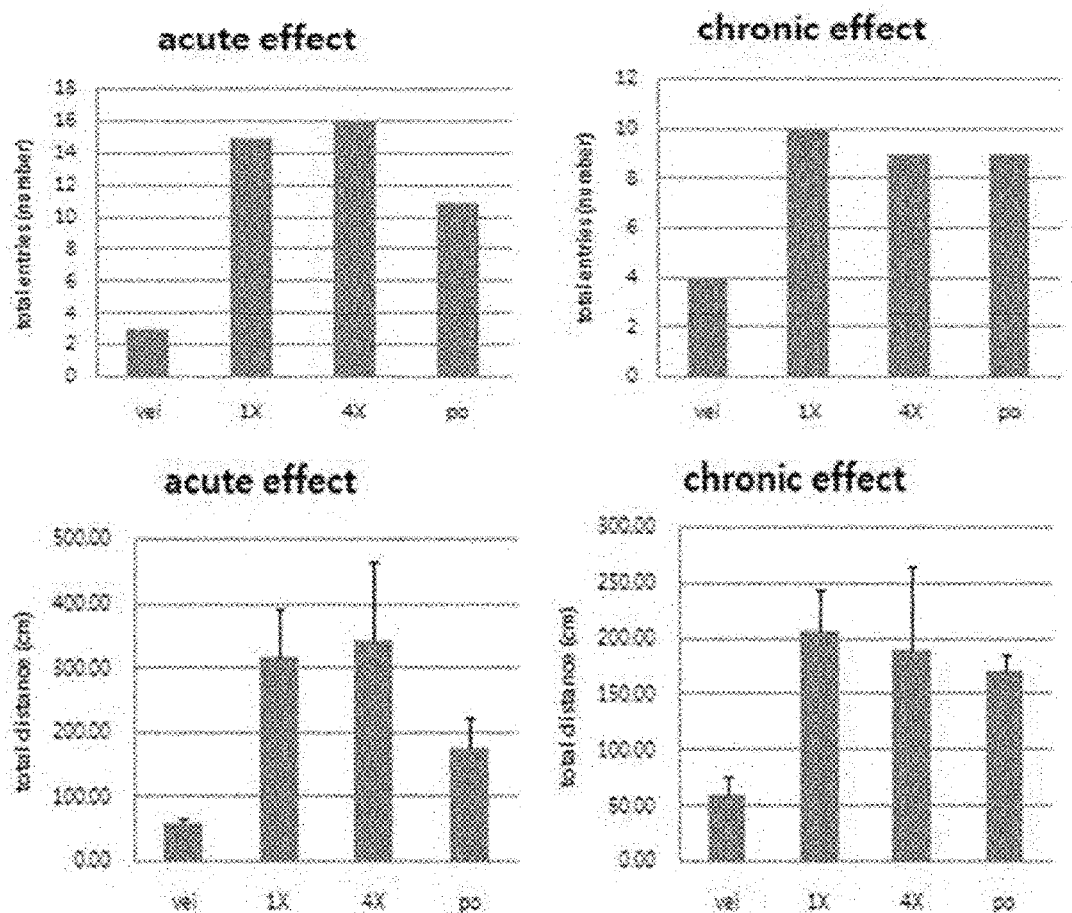

[FIG. 37]
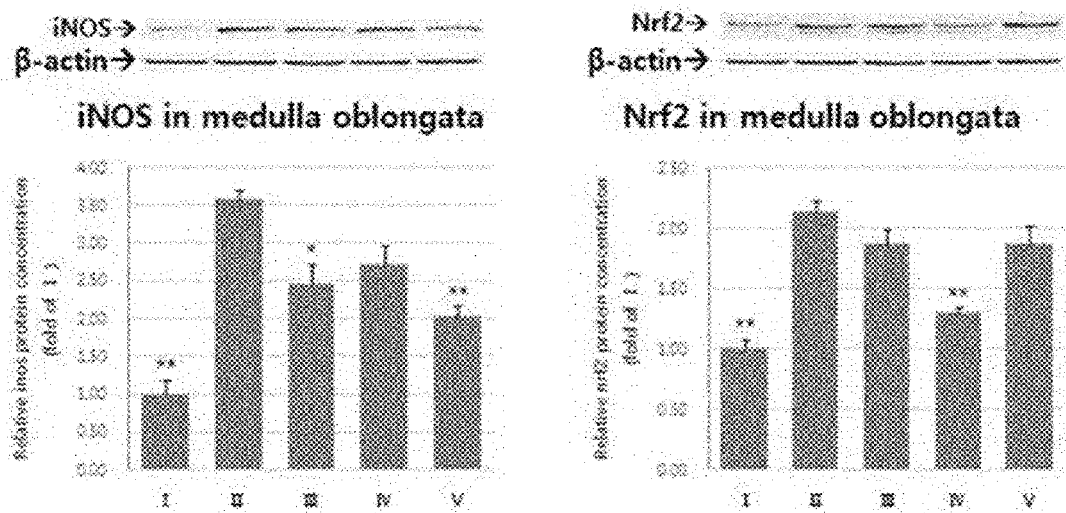
[FIG. 38]
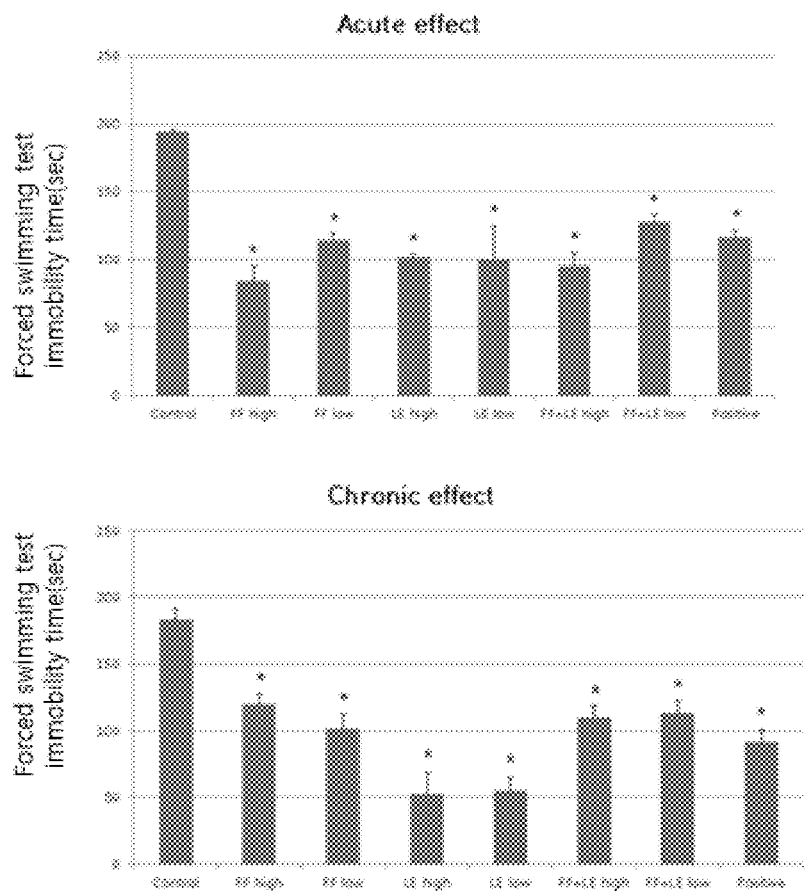

[FIG. 39]
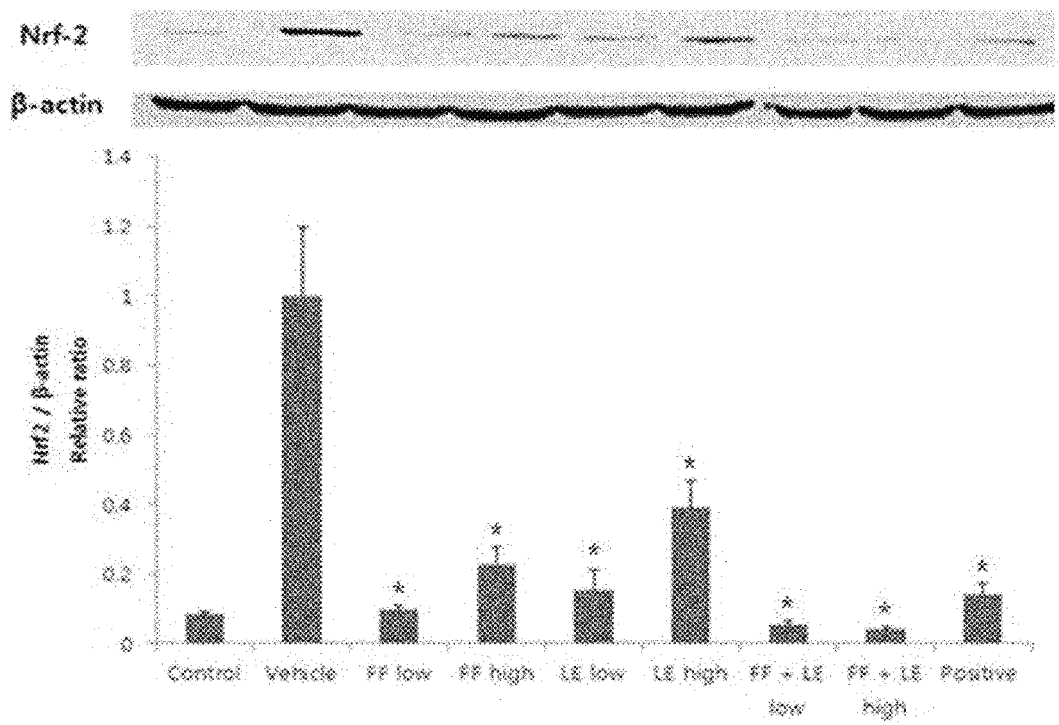
[FIG. 40a]
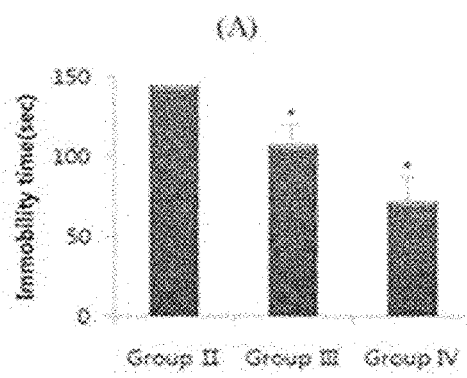
[FIG. 40b]
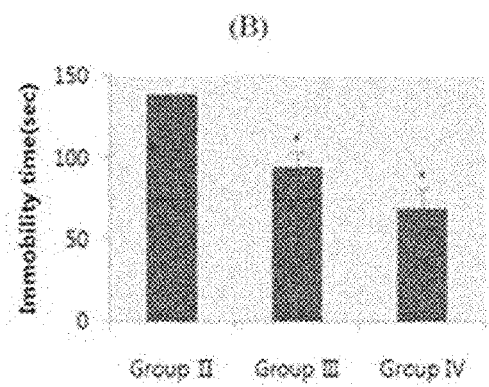

[FIG. 41a]
(A)
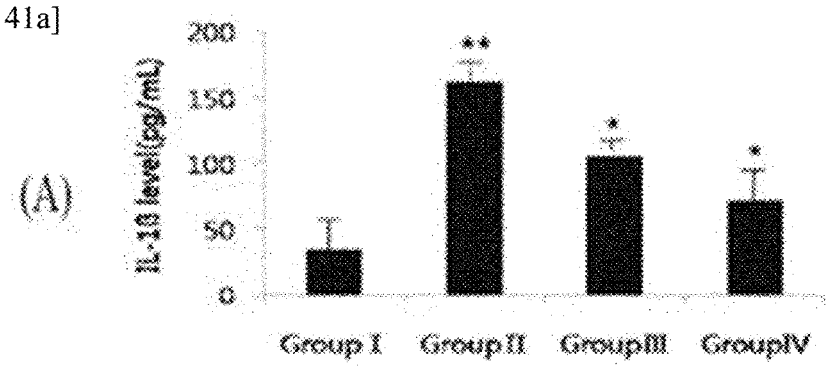
[FIG. 41b]
(B)
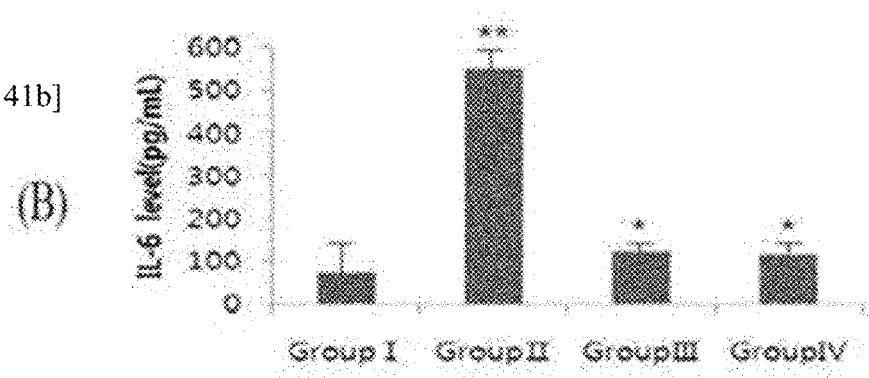
[FIG. 41c]
(C)
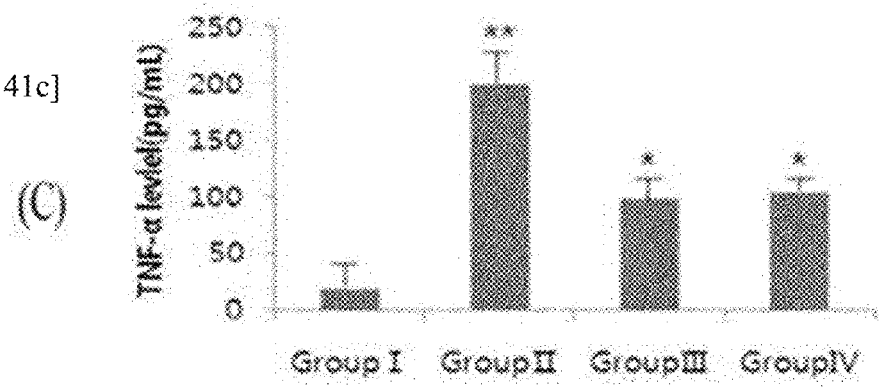

[FIG. 42a]
(A) 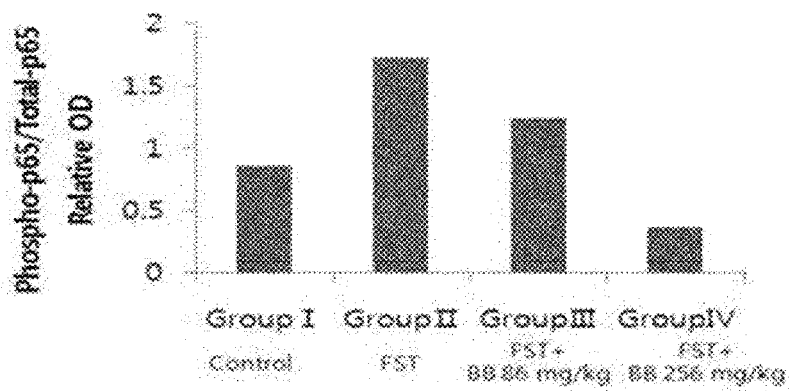
[FIG. 42b]
(B) 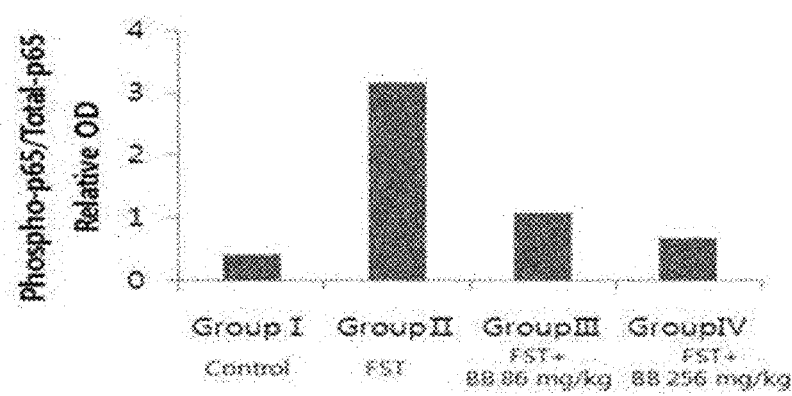
[FIG. 42c]
(C) 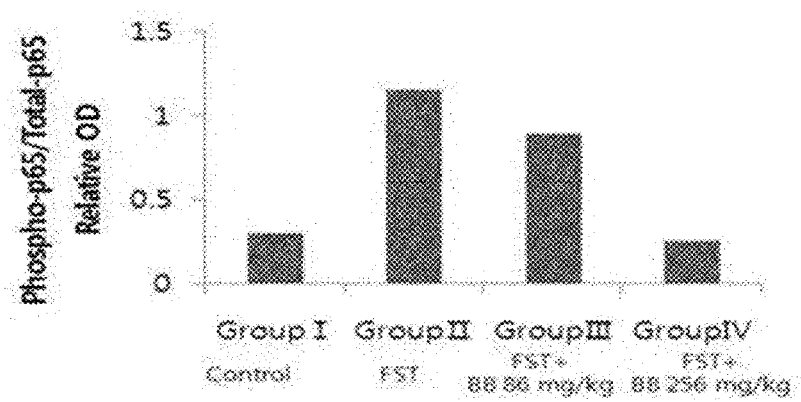

[FIG. 43]
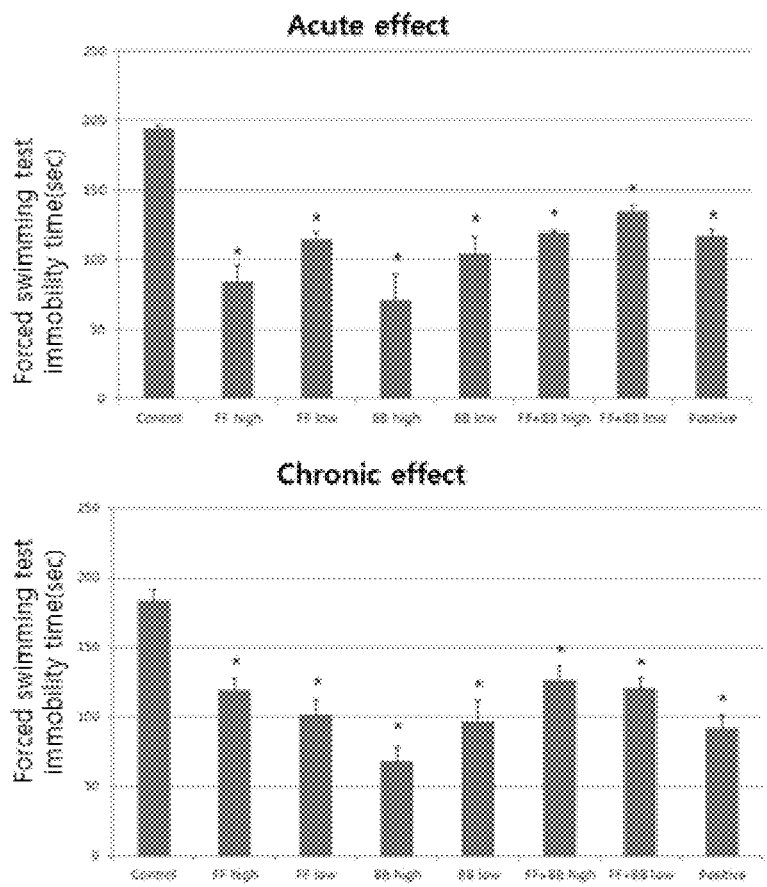
[FIG. 44]
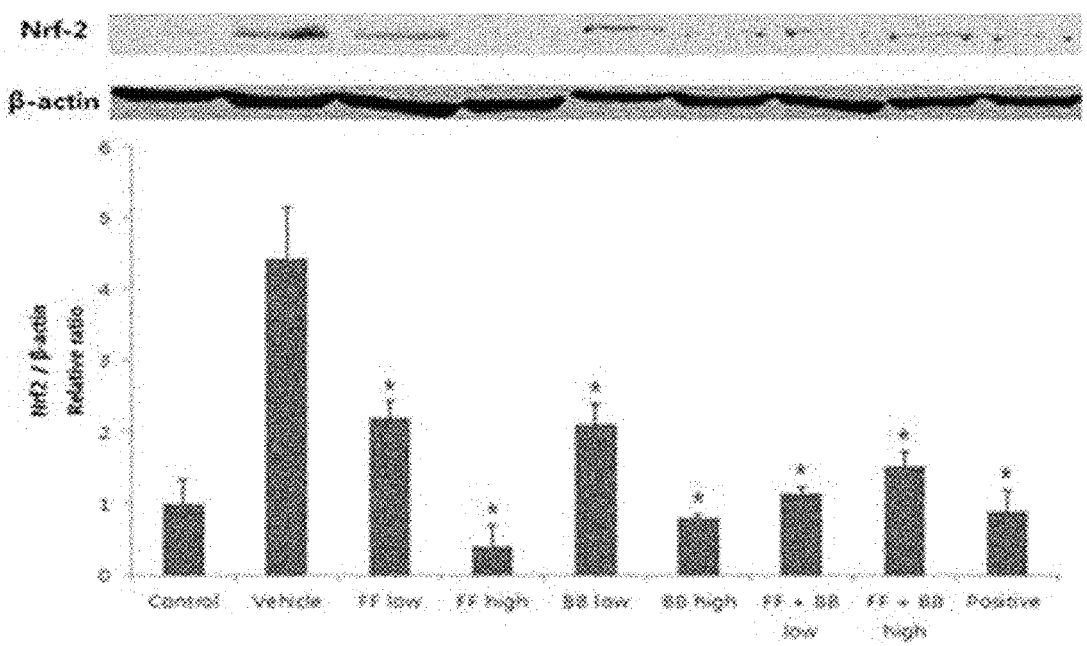

[FIG. 45a] 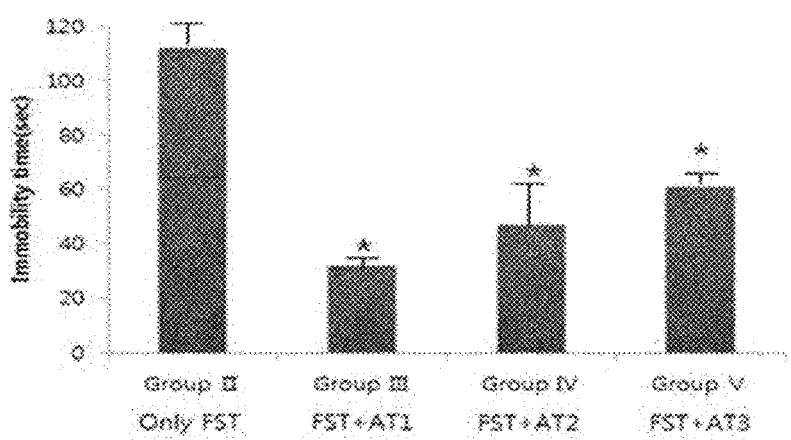
[FIG. 45b] 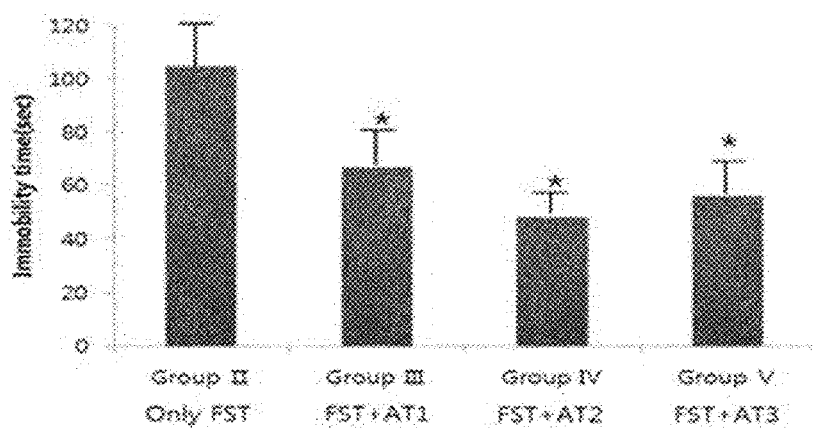

[FIG. 46a]
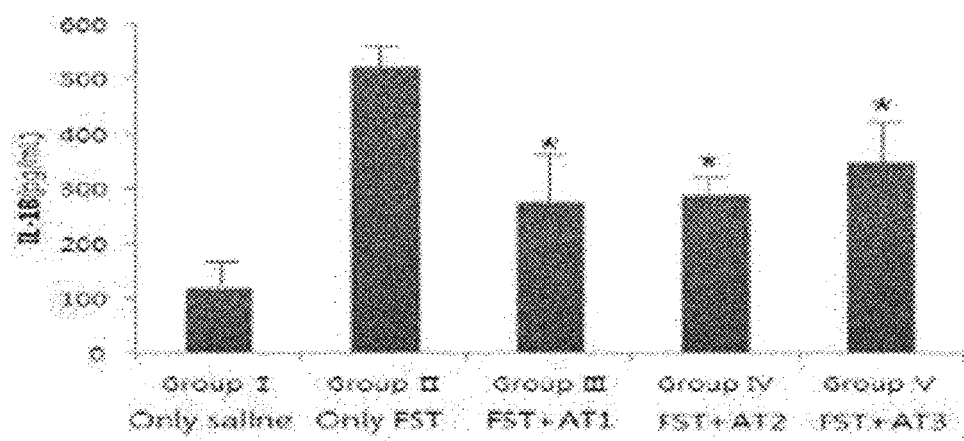
[FIG. 46b]
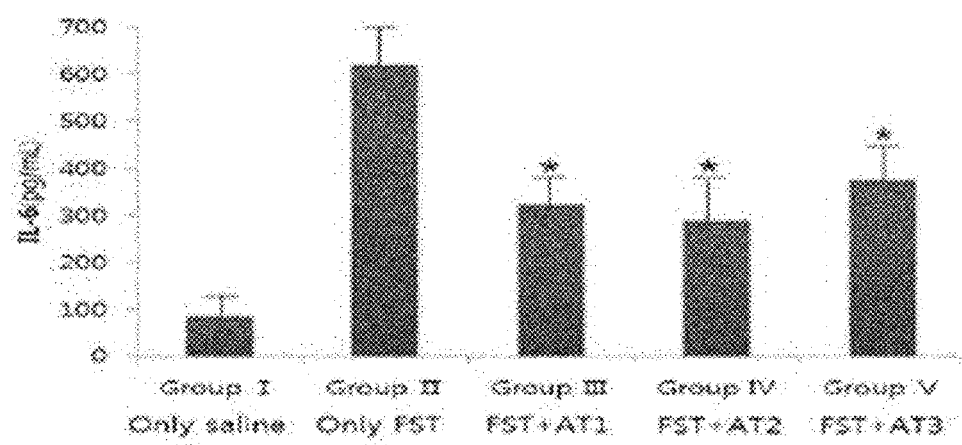
[FIG. 46c]
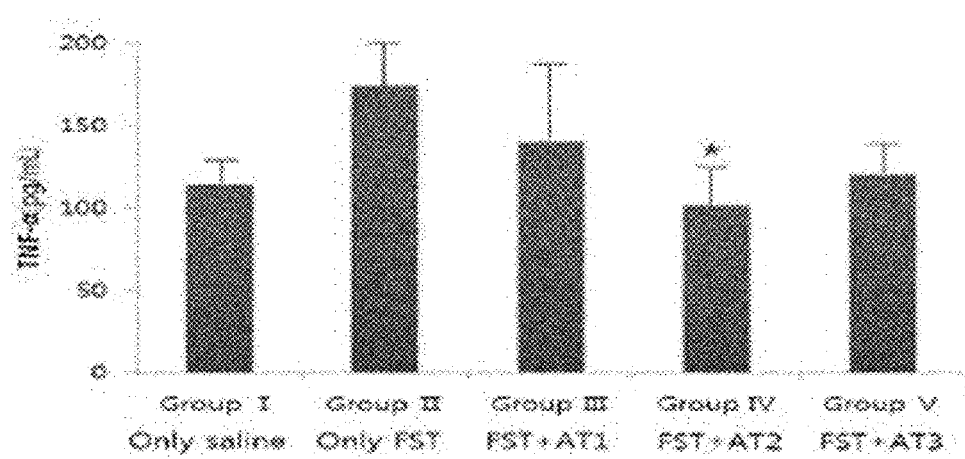

[FIG. 47]
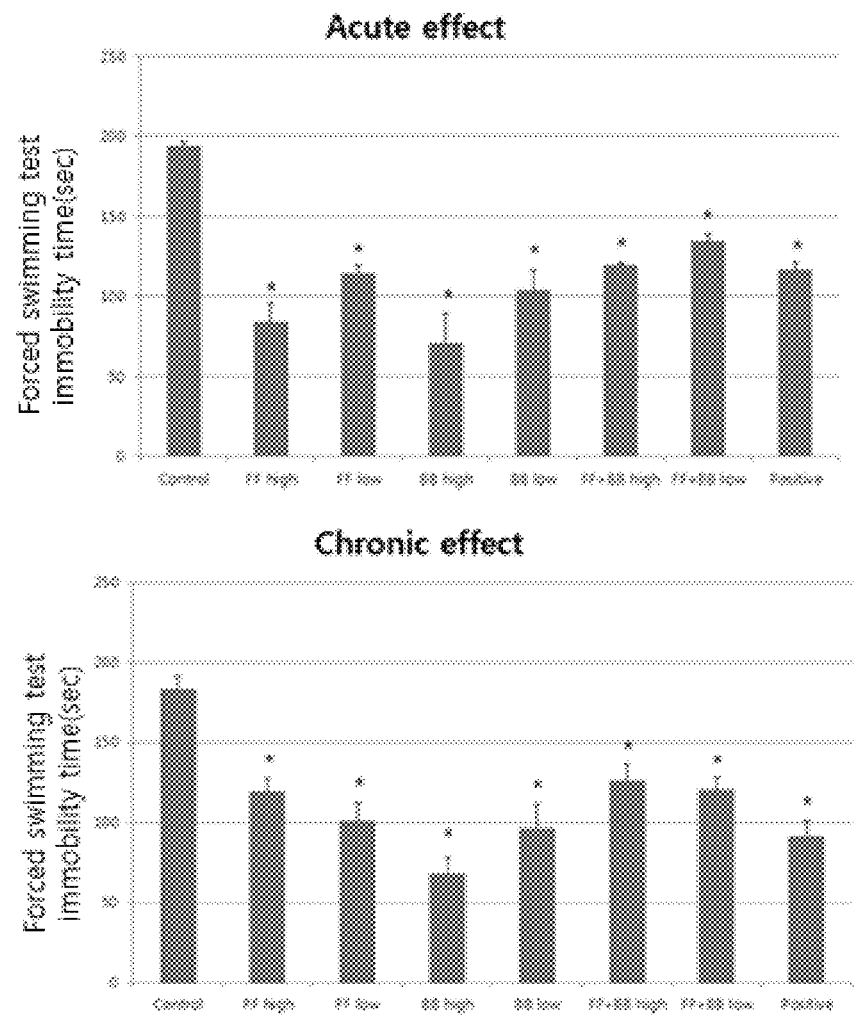

[FIG. 48]
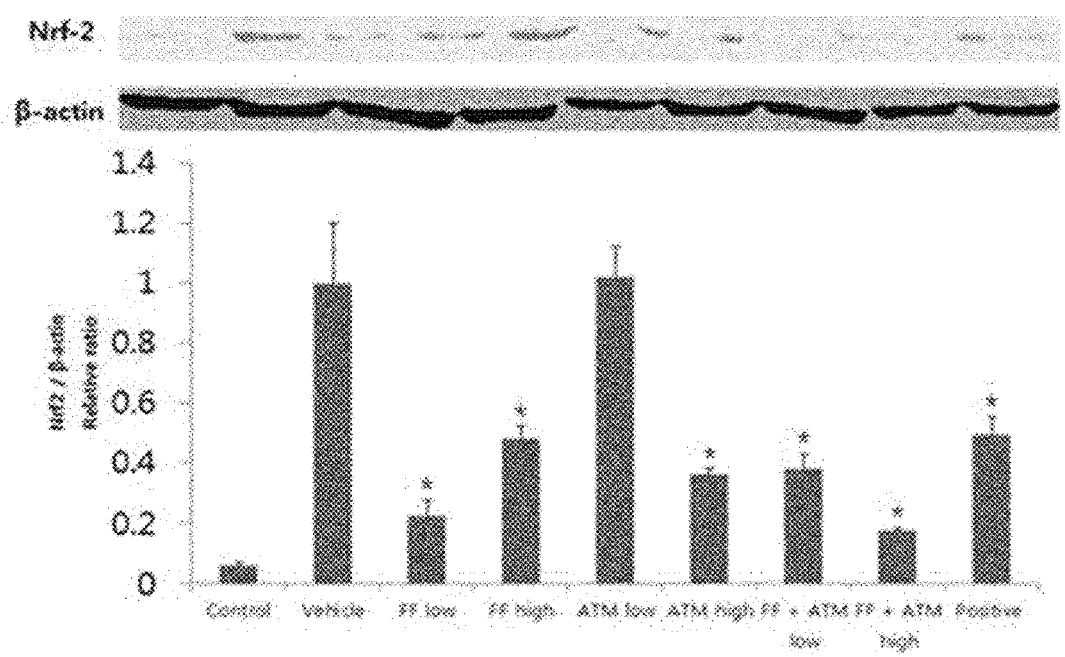

COMPOSITION FOR PREVENTING OR TREATING CRANIAL NERVE DISEASE COMPRISING FOMES FOMENTARIUS EXTRACT, FRACTION THEREOF, OR COMPOUND ISOLATED THEREFROM AS ACTIVE INGREDIENT

TECHNICAL FIELD

The present disclosure relates to a composition for preventing or treating a cranial nerve disease including a *Fomes fomentarius* extract, a fraction thereof, or a compound isolated therefrom as an active ingredient.

BACKGROUND ART

Dementia is a word derived from Latin, which means 'loss of mind,' and refers to a state in which as a person who has been living in normal life is suffering from various causes of brain damage, his or her cognitive function is lowered continuously and overall compared to the past, and his or her daily life is considerably obstructed. Clinically, the dementia is classified into the following diseases: Alzheimer's disease, vascular dementia, and other dementia. Common features of dementia include, e.g., senile plaques and apoptosis of nerve cells.

Drugs to cure dementia have not been developed currently. Medications that slow down neuropathologic progression and medications that relieve symptoms have been used. Immunotherapy for the purpose of reducing accumulation of amyloid protein and tau protein by preclinical experiments and stem cell therapy for nerve regeneration have been studied, but have limitations such as cytotoxicity and cell survival rate. The most common dementia treatment drugs are antioxidants, anti-inflammatory drugs, female hormones, and acetylcholinesterase inhibitors. They are classified into 4 types according to their mechanisms of action. The main dementia treatment drugs used in clinical use are donepezil (Aricept, 1996) and tacrine (Cgnex, 1994), a class of acetylcholinesterase inhibitors). However, the tacrine is more expensive than the efficacy and has serious problems of hepatotoxicity. The donepezil does not have hepatotoxicity but stimulates parasympathetic nerves to cause various side effects such as vomiting, nausea, and diarrhea. In addition, the drugs are not medicines for the treatment of underlying diseases such as improvement of cerebral lesions, but are merely drugs for alleviating major symptoms of dementia such as memory loss.

Therefore, studies for developing a new type of dementia treatment agent allowing the fundamental treatment without the above-mentioned side effects are being actively carried out. Efforts continue to develop a material, as one of them, which can induce the regulation of cytokine activity and block the activation of microglial microglia, which is known to be the cause of dementia. In particular, induction of cytokine activity expressed in microglial cells and inhibition of the expression of MAPK and NF-κB, which are the inflammatory signal pathways thereof, are one of the goals of developing a new therapeutic agent for dementia which has a clear mechanism of action and no side effects.

Currently, Enbrel (USA) is an anti-TNF-α inhibitor and has been approved by the FDA as a drug for treating rheumatoid arthritis. It has been approved as a treatment for dementia. It is known that Enbrel is effective in symptom improvement of dementia patients in clinical practice. Thus, it is currently being used as a treatment for dementia. However, non-steroidal anti-inflammatory drugs such as Enbrel have a limitation in that the therapeutic effect is inconsistent and that it is difficult to overcome the difficulty taking for a long-term due to side effects such as a gastrointestinal disorder and gastric ulcer.

In addition, the development of an inflammatory signal protein pathway modulator is relatively small due to the inhibition of cytokine derived from a natural compound, rather than a synthetic compound.

Accordingly, the present inventors have tried to develop a composition capable of promoting improvement and prevention of dementia and cognitive dysfunction, including an active ingredient derived from a natural substance, which has less adverse effects on the human body and can be easily prepared and ingested than a chemical synthetic medicine, thereby confirming such use of the *Fomes fomentarius* extract and finally completing the present disclosure.

DISCLOSURE

Technical Problem

Therefore, an object of the present disclosure is to provide a pharmaceutical composition for preventing or treating a cranial nerve disease including a *Fomes fomentarius* extract, a fraction thereof, or a compound isolated therefrom as an active ingredient.

Further, another object of the present disclosure is to provide a food composition for preventing or improving cranial nerve disease including a *Fomes fomentarius* extract, a fraction thereof, or a compound isolated therefrom as an active ingredient.

Technical Solution

To achieve the above-described objects, the present disclosure provides a pharmaceutical composition for preventing or treating a cranial nerve disease including a *Fomes fomentarius* extract, a fraction thereof, or a compound isolated therefrom as an active ingredient.

In one exemplary embodiment of the present disclosure, the fraction may be extracted with an ethyl acetate fraction, a hexane fraction, a chloroform fraction, or a butanol fraction.

In one exemplary embodiment of the present disclosure, the compound may be nonadecanone (2-Nonadecanone) or docosenol (cis-13-Docosenol).

In one exemplary embodiment of the present disclosure, the pharmaceutical composition may further include one or more selected from the group consisting of *Berchemia berchemiaefolia*, *Acer tegmentosum maxim*, and *Lithospermum erythrorhizon*.

In one exemplary embodiment of the present disclosure, the *Fomes fomentarius* extract, the fraction thereof, or the compound isolated therefrom can inhibit the production or expression of the inflammatory cytokine.

In one exemplary embodiment of the present disclosure, the *Fomes fomentarius* extract, the fraction thereof, or the compound isolated therefrom may improve the glucose metabolism activity of the brain.

In one exemplary embodiment of the present disclosure, the cranial nerve disease can be one selected from the group consisting of neurodegenerative disease, disease caused by ischemia or reperfusion, and a mental disorder.

In one exemplary embodiment of the present disclosure, the neurodegenerative disease may be one selected from the group consisting of Parkinson's disease, Huntington's disease, Alzheimer's disease, mild cognitive impairment, senile dementia, amyotrophic lateral sclerosis, spinocerebellar atrophy, Tourette's Syndrome, Friedrich's Ataxia, Machado-Joseph's disease, Lewy body dementia, dystonia, progressive supranuclear palsy, and frontotemporal dementia.

In one exemplary embodiment of the present disclosure, the disease caused by ischemia or reperfusion may be one selected from the group consisting of ischemic stroke, cerebral hemorrhage, cerebral infarction, head injury, and a cerebral circulatory-metabolic disorder.

In one exemplary embodiment of the disclosure, the mental disorder may be one selected from the group consisting of anxiety, depression, a mood disorder, insomnia, a delusional disorder, an obsessive-compulsive disorder, migraine, stress, memory impairment, a cognitive disorder, a senile dementia-related disorder, an Alzheimer's disease-related disorder, Parkinson's disease-related disorder, an attention disorder, an insomnia disorder, and an ischemic or brain trauma-related disorder.

Further, the present disclosure provides a food composition for preventing or improving a cranial nerve disease including a *Fomes fomentarius* extract, a fraction thereof, or a compound isolated therefrom as an active ingredient.

In one exemplary embodiment of the present disclosure, the fraction may be extracted with an ethyl acetate fraction, a hexane fraction, a chloroform fraction, or a butanol fraction.

In one exemplary embodiment of the present disclosure, the compound may be nonadecanone (2-Nonadecanone) or docosenol (cis-13-Docosenol).

In one exemplary embodiment of the present disclosure, the pharmaceutical composition may further include at least one selected from the group consisting of *berchemia berchemiaefolia, acer tegmentosum maxim*, and *Lithospermum erythrorhizon*.

Advantageous Effect

According to the present disclosure, it is constituted with a *Fomes fomentarius* extract, a fraction thereof, or a compound isolated therefrom as an active ingredient so that there are significant effects of inhibiting the production or expression of inflammatory cytokines and improving the activity of glucose metabolism in the brain to prevent or treat cranial nerve diseases, of lowering side effects on the human body as a natural product, and of being easily prepared and ingested.

DESCRIPTION OF DRAWINGS

FIG. 1 shows the results of MTT analysis according to an exemplary embodiment of the present disclosure.

FIGS. 2A-2B show graphs of in-vitro (A) IL-1β level and (B) TNF-α level according to one exemplary embodiment of the present disclosure.

FIG. 3 shows the results of a Morris water maze test according to one exemplary embodiment of the present disclosure.

FIG. 4 shows the results of a forced swimming test according to one exemplary embodiment of the present disclosure.

FIGS. 5A-5C show the results of an animal PET-CT test using $^{18}$F-FDG according to one exemplary embodiment of the present disclosure (a: PET-CT photograph, b to d: graphs showing quantitatively comparison of the relative glucose uptake of the brain to each part of the brain relative to each other).

FIGS. 6A-6B show graphs of in-vitro (A) IL-1β level and (B) TNF-α level according to one exemplary embodiment of the present disclosure.

FIGS. 7A-7B show the results of p38 phosphorylation in (a) a spinal cord and (b) a medulla oblongata according to one exemplary embodiment of the present disclosure.

FIGS. 8A-8B show the results of NF κ-B phosphorylation in (a) a spinal cord and (b) a medulla oblongata according to one exemplary embodiment of the present disclosure.

FIG. 9 shows the results of various solvent fractionation of the *Fomes fomentarius* methanol extract.

FIG. 10 shows the results of measuring DPPH radical scavenging activity of various *Fomes fomentarius*.

FIG. 11 shows the results of measuring xanthine oxidase inhibitory activity of various *Fomes fomentarius* fractions.

FIG. 12 shows the results of measuring acetylcholinesterase inhibitory activity of various *Fomes fomentarius* fractions.

FIG. 13 shows the results of measuring acetylcholinesterase inhibitory activity of each fraction of the *Fomes fomentarius* chloroform ($CHCl_3$) fraction.

FIG. 14 shows the results of measuring DPPH radical scavenging activity of nonadecanone (2-Nonadecanone) and docosenol (cis-13-Docosenol) compounds isolated in the present disclosure.

FIG. 15 shows the results of measuring xanthine oxidase inhibitory activity of nonadecanone (2-Nonadecanone) and docosenol (cis-13-Docosenol) compounds isolated in the present disclosure.

FIG. 16 shows the results of measuring acetylcholinesterase inhibitory activity of nonadecanone (2-Nonadecanone) and docosenol (cis-13-Docosenol) compounds isolated in the present disclosure.

FIG. 17 shows the results of confirming the degree of NO production by the treatment with the *Fomes fomentarius* $CHCl_3$ fraction, nonadecanone (2-Nonadecanone) and docosenol (cis-13-Docosenol) compounds.

FIG. 18 shows the results of measuring IL-1β as an inflammatory cytokine by the treatment with the *Fomes fomentarius* $CHCl_3$ fraction, nonadecanone (2-Nonadecanone) and docosenol (cis-13-Docosenol) compounds.

FIG. 19 shows the results of measuring IL-6 as an inflammatory cytokine by the treatment with the *Fomes fomentarius* $CHCl_3$ fraction, nonadecanone (2-Nonadecanone) and docosenol (cis-13-Docosenol) compounds.

FIG. 20 shows the results of measuring TNF-α as an inflammatory cytokine by the treatment with the *Fomes fomentarius* $CHCl_3$ fraction, nonadecanone (2-Nonadecanone) and docosenol (cis-13-Docosenol) compounds.

FIG. 21 shows the results confirmed by Western blotting of the inhibitory effect of the *Fomes fomentarius* $CHCl_3$ fraction, nonadecanone (2-Nonadecanone) and docosenol (cis-13-Docosenol) compounds on NF-κB and p38 phosphorylation induced by LPS.

FIG. 22 shows the results of MTT analysis of the *Acer tegmentosum maxim* extracts with various concentrations.

FIG. 23 shows the results of measuring DPPH radical scavenging activity of the *Acer tegmentosum maxim* extracts with various concentrations.

FIG. 24 shows the results of measuring xanthine oxidase inhibitory activity of the *Acer tegmentosum maxim* extracts with various concentrations.

FIG. 25 shows the results of MTT analysis of the *berchemia berchemiaefolia* extracts with various concentrations.

FIG. 26 shows the results of measuring DPPH radical scavenging activity of the *berchemia* berchemiaefolia extracts with various concentrations.

FIG. 27 shows the results of measuring xanthine oxidase inhibitory activity of the *berchemia* berchemiaefolia extracts with various concentrations.

FIG. 28 shows the results of MTT analysis of the *Lithospermum erythrorhizon* extracts with various concentrations.

FIG. 29 shows the results of measuring DPPH radical scavenging activity of the *Lithospermum erythrorhizon* extracts with various concentrations.

FIG. 30 shows the results of measuring xanthine oxidase inhibitory activity of the *Lithospermum erythrorhizon* extracts with various concentrations.

FIG. 31 shows a scheme of the forced swimming test (FST) method and plan according to one exemplary embodiment of the present disclosure.

FIG. 32 shows the results of measuring the immobility time of the forced swimming test on the oral administration of the *Fomes fomentarius* extract in one exemplary embodiment of the present disclosure (Vei: FST induced group, 1×: FST+FEE 100 mg/kg treated group, 4×: FST+FEE 25 mg/kg treated group, Po: FST+sodium tianeptine 10 mg/kg treated group, *: $p<0.05$ (compare with vehicle), **: $p<0.01$ (compare with vehicle)).

FIG. 33 shows the results of mobility evaluation according to total entries and total distance in Y-maze on the oral administration of the *Fomes fomentarius* extract in one exemplary embodiment of the present disclosure (Vei: FST induced group, 1×: FST+FEE 100 mg/kg treated group, 4×: FST+FEE 25 mg/kg treated group, Po: FST+sodium tianeptine 10 mg/kg treated group, *: $p<0.05$ (compare with vehicle), **: $p<0.01$ (compare with vehicle)).

FIG. 34 shows the results of analysis of the signal transmission protein expression in the medulla oblongata and the adrenal gland on the oral administration of the *Fomes fomentarius* extract in one exemplary embodiment of the present disclosure (I: control, II: FST induced group, III, IV: FST+FEE 100, 25 mg/kg treated group, V: FST+sodium tianeptine 10 mg/kg treated group, *: $p<0.05$ (compare with vehicle), **: $p<0.01$ (compare with vehicle).

FIG. 35 shows the results of measuring the immobility time of the forced swimming test on the oral administration of the *Lithospermum erythrorhizon* extract in one exemplary embodiment of the present disclosure (acute effect: the second FST (1-day operation), chronic effect: the last FST (6-day operation), (Vei: FST induced group, 1×: FST+LE Extract 100 mg/kg treated group, 4×: FST+LE extract 25 mg/kg treated group, Po: FST+sodium tianeptine 10 mg/kg treated group, *: $p<0.05$ (compare with vehicle), **: $p<0.01$ (compare with vehicle)).

FIG. 36 shows the results of mobility evaluation according to total entries and total distance in Y-maze on the oral administration of the *Lithospermum erythrorhizon* extract in one exemplary embodiment of the present disclosure (Vei: FST induced group, 1×: FST+LE extract 100 mg/kg treated group, 4×: FST+LE extract 25 mg/kg treated group, Po: FST+sodium tianeptine 10 mg/kg treated group).

FIG. 37 shows the results of analysis of the signal transmission protein expression in the medulla oblongata and the adrenal gland on the oral administration of the *Lithospermum erythrorhizon* extract in one exemplary embodiment of the present disclosure (I: control, II: FST induced group, III, IV: FST+LE extract 100, 25 mg/kg treated group, V: FST+sodium tianeptine 10 mg/kg treated group, *: $p<0.05$ (compare with vehicle), **: $p<0.01$ (compare with vehicle)).

FIG. 38 shows the results of measuring the immobility time of the forced swimming test on the oral administration of the *Fomes fomentarius/lithospermum erythrorhizon* extract mixture in one exemplary embodiment of the present disclosure (FF: *Fomes fomentarius*, LE: *Lithospermum erythrorhizon*, high: 100 mg/kg, low: 25 mg/kg, positive: sodium tianeptine 10 mg/kg, *: $p<0.05$ (compare with control group), **: $p<0.01$ (compare with control group)).

FIG. 39 shows the results of analysis of the signal transmission protein expression in the medulla oblongata and the adrenal gland on the oral administration of the *Fomes fomentarius/lithospermum erythrorhizon* extract in one exemplary embodiment of the present disclosure (FF: *Fomes fomentarius*, LE: *Lithospermum erythrorhizon*; high: 100 mg/kg, low: 25 mg/kg, positive: sodium tianeptine 10 mg/kg, *: $p<0.05$ (compare with control group), **: $p<0.01$ (compare with control group)).

FIGS. 40A-40B show the results of measuring the immobility time of the forced swimming test on the oral administration of the *berchemia* berchemiaefolia extract in one exemplary embodiment of the present disclosure ((A): the second FST (1-day operation, acute effect), (B): The last FST (6 day operation, chronic effect), (Group II: only FST, Group III: FST+BB 86 mg/kg, Group IV: FST+BB 256 mg/kg, *: $p<0.05$ with compare with Group II).

FIGS. 41A-41C show the results of (A) IL-1β, (B) IL-6, and (C) TNF-α concentration analysis of cytokines on the oral administration of the *berchemia* berchemiaefolia extract in one exemplary embodiment of the present (Group I: control (saline), Group II: only FST, Group III: FST+BB 86 mg/kg, Group IV FST+BB 256 mg/kg, *: $p<0.05$ (compare with Group II)).

FIGS. 42A-42C show the results of the expression of phosphorylated-NFkBp65 proteins in (A) the adrenal gland, (B) the medulla oblongata, and (C) the brain on the oral administration of the *berchemia* berchemiaefolia extract according to one exemplary embodiment of the present disclosure (group II: only FST, group III: FST+BB 86 mg/kg, group IV: FST+BB 256 mg/kg, OD: optical density, BB: *berchemia* berchemiaefolia, FST: forced swimming test).

FIG. 43 shows the results of measuring the immobility time of the forced swimming test on the oral administration of the *Fomes fomentarius/berchemia* berchemiaefolia extract mixture in one embodiment of the present disclosure (FF: *Fomes fomentarius*, BB: *berchemia* berchemiaefolia, high: 100 mg/kg, low: 25 mg/kg, positive: sodium tianeptine 10 mg/kg, *: $p<0.01$ (compare with control group)).

FIG. 44 shows the results of analysis of the signal transmission protein expression in the medulla oblongata on the oral administration of the *Fomes fomentarius/berchemia* berchemiaefolia extract mixture in one exemplary embodiment of the present disclosure (FF: *Fomes fomentarius*, BB: *berchemia* berchemiaefolia, high: 100 mg/kg, low: 25 mg/kg, positive: sodium tianeptine 10 mg/kg).

FIGS. 45A-45B show the results of measuring the immobility time of the forced swimming test on the oral administration of the *Acer tegmentosum maxim* extract in one exemplary embodiment of the present disclosure ((A): the second FST (1-day operation, acute effect), (B): the last FST (6-day operation, chronic effect), (Group II: only FST, Group III: FST+AT 400 mg/kg, Group IV: FST+AT 200 mg/kg, Group V: FST+AT 100 mg/kg, *: $p<0.05$ (compare with Group II)).

FIGS. 46A-46C show the results of (A) IL-1β, (B) IL-6, and (C) TNF-α concentration analysis of cytokines on the oral administration of the *Acer tegmentosum maxim* extract in one exemplary embodiment of the present (Group II: only FST, Group III: FST+AT 400 mg/kg, Group IV: FST+AT 200 mg/kg, Group V: FST+AT 100 mg/kg, *: p<0.05 (compare with Group II)).

FIG. 47 shows the results of measuring the immobility time of the forced swimming test on the oral administration of the *Fomes fomentarius/Acer tegmentosum maxim* extract mixture in one exemplary embodiment of the present disclosure. The ratio of the mixture of the *Fomes fomentarius* extract and the *Acer tegmentosum maxim* extract was 4:1. (FF: *Fomes fomentarius*, ATM: *Acer tegmentosum maxim*, high: 100 mg/kg, low: 25 mg/kg, positive: sodium tianeptine 10 mg/kg, *: p<0.05 (compare with Group II), **: p<0.01 (compare with control group)).

FIG. 48 shows the results of analysis of the signal transmission protein expression in the medulla oblongata on the oral administration of the *Fomes fomentarius/Acer tegmentosum maxim* extract mixture in one exemplary embodiment of the present disclosure (FF: *Fomes fomentarius*, ATM: *Acer tegmentosum maxim*, high: 100 mg/kg, low: 25 mg/kg, positive: sodium tianeptine 10 mg/kg, *: p<0.05 (compare with Group II), **: p<0.01 (compare with control group)).

BEST MODE FOR CARRYING OUT THE INVENTION

The present disclosure relates to a pharmaceutical composition for preventing or treating a cranial nerve disease including a *Fomes fomentarius* extract, a fraction thereof, or a compound isolated therefrom as an active ingredient. Hereinafter, the present disclosure will be described in detail.

First, the term 'extract' as used herein means that it is used as a crude extract in the art, but it also includes broadly a fraction in which the extract is further fractionated. That is, the *Fomes fomentarius* extract used in the present disclosure includes not only those obtained using an extraction solvent but also those obtained by additionally applying a purification process thereto. For example, the *Fomes fomentarius* extract of the present disclosure includes a fraction obtained by passing the extract through an ultrafiltration membrane having a constant molecular weight cut-off value or a fraction obtained through various purification methods additionally performed such as a separation by various chromatography (made for separation according to size, charge, hydrophobicity or affinity). Further the *Fomes fomentarius* extract used in the present disclosure may be prepared in a powder form by an additional process such as distillation under reduced pressure, freeze drying, and spray drying.

Further, the term "including as an active ingredient" used herein includes an amount sufficient to achieve the efficacy or activity of the following *Fomes fomentarius* extract. The present disclosure is a composition extracted from the *Fomes fomentarius* which is a natural plant material. Thus, there is no adverse effect on the human body even when it is administered in an excessive amount. Therefore, the quantitative upper limit of the *Fomes fomentarius* extract contained in the composition of the present disclosure can be selected and carried out within a suitable range by a skilled person in the art.

In one aspect, the present disclosure relates to a pharmaceutical composition for preventing or treating cranial nerve diseases, which includes the *Fomes fomentarius* extract as an active ingredient.

The pharmaceutical composition of the present disclosure can be used for the prevention or treatment of cranial nerve diseases. At this time, the cranial nerve disease includes neurodegenerative disease, disease caused by ischemia or reperfusion, and a mental disorder.

Specifically, the neurodegenerative disease may be a neurological disease selected from the group consisting of Parkinson's disease, Huntington's disease, Alzheimer's dementia, mild cognitive impairment, senile dementia, amyotrophic lateral sclerosis, spinocerebellar atrophy, Tourette's Syndrome, Friedrich's Ataxia, Machado-Joseph's disease, Lewy body dementia, dystonia, progressive supranuclear palsy, and frontotemporal dementia.

Further, the disease caused by ischemia or reperfusion may be a disease selected from the group consisting of ischemic stroke, cerebral hemorrhage, cerebral infarction, head injury, and a cerebral circulatory-metabolic disorder.

Further, the mental disorder may be a mental disorder selected from the group consisting of be anxiety, depression, mood disorder, a delusional disorder, an obsessive-compulsive disorder, migraine, stress, memory impairment, a cognitive disorder, senile dementia, dementia-related disorders, a Parkinson's disease-related disorder, an attention disorder, an insomnia disorder, and an ischemia- or trauma-related disorder.

In particular, early blockade of microglial activity can be a very effective treatment for neurological diseases such as dementia because it inhibits delayed neuronal cell death in the brain so that it can provide the window of therapeutic time to mitigate additional brain damage due to early neuronal cell death. According to one exemplary embodiment of the present disclosure, it was confirmed that the *Fomes fomentarius* extract significantly inhibited the secretion of pro-inflammatory cytokines, IL-6 and TNF-α in LPS-stimulated microglial cells in vitro. (See FIG. 2)

In addition, according to one exemplary embodiment of the present disclosure, when the *Fomes fomentarius* extract is orally administered to an experimental animal in which dementia is induced by scopolamine, IL-1β and TNF-α levels were significantly inhibited in both before and after induction of dementia. (See FIG. 6). Furthermore, the levels of p38 and NF-κB p65 protein were increased sharply in the scopolamine-induced dementia disease model. In the group administered with the *Fomes fomentarius* extract, the expressions of the proteins in the pre-treated group before induction of dementia and the post-treated group were effectively inhibited (See FIGS. 7 and 8).

In other words, the *Fomes fomentarius* extract as an active ingredient contained in the composition of the present disclosure can be effectively used to inhibit production or expression of inflammatory cytokines, so that it can be used for prevention or treatment of cranial nerve diseases.

In addition, as the progress of cranial nerve diseases such as dementia, the degree of glucose metabolic activity in the brain regions decreases as the brain cell activity is decreased or killed. In one exemplary embodiment of the present disclosure related, $^{18}$F-Fluorodeoxyglucose ($^{18}$F-FDG) was used to examine the brain activity mapping and the degree of glucose metabolism in the experimental animals. As a result, in the scopolamine-induced dementia disease model, the degree of glucose metabolism was noticeably elevated in both pre-treated *Fomes fomentarius* extract-administered group and post-treated *Fomes fomentarius* extract-administered group while the degree of glucose metabolism in the brain was significantly decreased compared to control group. That is, the *Fomes fomentarius* extract showed about 21% increase in glucose uptake in the frontal lobe and parietal lobe areas which control the cognition, intellectual ability, and behavioral ability, which are closer to normal than those of the disease model, compared with the vehicle (Alzheimer disease-induced group). Therefore, the *Fomes fomentarius* extract as an active ingredient to be included in the composition of the present disclosure can be used for prevention and treatment of cranial nerve diseases by improving the activity of glucose metabolism in each part of the brain, particularly the cerebrum.

Further, the composition of the present disclosure can be used in combination with other extracts in addition to the *Fomes fomentarius* extract, the fraction thereof or the compound isolated therefrom, including, but not limited to, at least one selected from the group consisting of *berchemia berchemiaefolia*, *Acer tegmentosum maxim*, and *Lithospermum erythrorhizon*.

The present disclosure also relates to a pharmaceutical composition for preventing or treating cranial nerve diseases, including a nonadecanone (2-Nonadecanone) compound represented by the following chemical formula 1 or a docosenol (cis-13-Docosenol) compound represented by the following chemical formula 2 as an active ingredient.

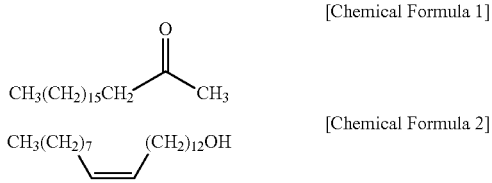

[Chemical Formula 1]

[Chemical Formula 2]

The compound of formula 1 or 2 according to the present disclosure can be obtained by extracting and isolating from nature using a method known in the art for extraction and isolation. In one exemplary embodiment of the disclosure, it may be isolated from *Fomes fomentarius*.

The compound according to the present disclosure can be used in the form of a salt, preferably a pharmaceutically acceptable salt, wherein the salt is preferably an acid addition salt formed by a pharmaceutically acceptable free acid. As the free acid, organic acid and inorganic acid can be used. The organic acid includes, but is not limited to, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid, and aspartic acid. The inorganic acid includes, but is not limited to, hydrochloric acid, bromic acid, sulfuric acid, and phosphoric acid.

The two compounds according to the present disclosure can be isolated from nature or can be prepared by a chemical synthesis method known in the art, and commercially available products can also be used.

When the compounds of the present disclosure are isolated from nature, they can be obtained from all kinds of plants containing such compounds using methods of extraction and separation of conventional materials. That is, a plant extract (such as a *Fomes fomentarius* extract) can be obtained using an appropriate solvent, and the compound can be purified from the extract using a purification method known to those skilled in the art to which the present disclosure belongs.

Further, when the *Fomes fomentarius* extract used in the composition of the present disclosure is obtained by treating the *Fomes fomentarius* with the extracting solvent, various extracting solvents may be used. Preferably, a polar solvent or a non-polar solvent can be used. The suitable polar solvent includes (a) water, (b) alcohol (preferably methanol, ethanol, propanol, butanol, n-propanol, isopropanol, n-butanol, 1-pentanol, 2-butoxyethanol or ethylene glycol), (c) acetic acid, (d) dimethylformamide (DMFO), and (e) dimethyl sulfoxide (DMSO). The suitable non-polar solvent includes acetone, cyclohexane, cyclopentane, diisobutylene, 1-pentene, 1-chlorobutane, 1-chloropentane, xylene, diisopropyl ether, 2-chloropropane, toluene, 1-chloropropane, chlorobenzene, benzene, diethyl ether, diethylsulfide, chloroform, dichloromethane, 1,2-dichloroethane, aniline, diethylamine, ether, carbon tetrachloride, and THF. More preferably, the extracting solvent used in the present disclosure includes (1) water, (2) a dihydric or condensed lower alcohol having 1 to 4 carbon atoms (methanol, ethanol, propanol, butanol, etc.), (3) a mixed solvent of the lower alcohol and water, (4) acetone, (5) ethyl acetate, (6) chloroform, (7) butyl acetate, (8) 1,3-butylene glycol, (9) hexane, and (10) diethyl ether. Most preferably, the *Fomes fomentarius* extract of the present disclosure is obtained by treating *Fomes fomentarius* with water, ethanol or a combination thereof.

Further, (a) a pharmaceutically effective amount of the above-described *Fomes fomentarius* extract of the present disclosure and (b) a pharmaceutically acceptable carrier may be included to be prepared when the pharmaceutical composition of the present disclosure. The term "pharmaceutically effective amount" means an amount sufficient to achieve efficacy or activity of the above-described *Fomes fomentarius* extract.

Herein, the pharmaceutically acceptable carriers may be those conventionally used in pharmaceutical preparations such as, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil.

Further, the pharmaceutical composition of the present disclosure may further include a lubricant, a wetting agent, a sweetener, a flavoring agent, an emulsifying agent, a suspending agent, a preservative, etc., in addition to the above components. Suitable pharmaceutically acceptable carriers and formulations are described in detail in Remington's Pharmaceutical Sciences (19th ed., 1995).

The pharmaceutical composition of the present disclosure may be administered orally or parenterally. At this time, a suitable dosage of the pharmaceutical composition of the present disclosure varies depending on factors such as formulation method, administration method, age, body weight, sex, pathological condition, food, administration time, administration route, excretion rate, and responsiveness of the patient. Typical dosages of the pharmaceutical compositions of the present disclosure are in the range of 0.001 mg/kg to 100 mg/kg on an adult basis.

In addition, the pharmaceutical composition of the present disclosure may be formulated using a pharmaceutically acceptable carrier and/or an excipient according to a method which can be easily carried out by a person having ordinary skill in the art to which the present disclosure belongs, so as to be prepared into a unit dose form or manufactured by penetrating into a multi-dose container. Herein, the formulations may be in the form of solutions, a suspension, a syrup, or an emulsion in an oils or aqueous media, or in the form of an excipient, a flour, a powder, a granule, a tablet, or a capsule, and may additionally contain a dispersing or safening agent.

Further, according to another aspect of the present disclosure, the present disclosure relates to a food composition for preventing or improving cranial nerve disease including a *Fomes fomentarius* extract, a fraction thereof, or a compound isolated therefrom.

The food composition means a natural product or a processed product containing one or more nutrients, preferably a state of being able to be directly eaten through a certain degree of processing, and in a usual sense, includes a health functional food, a beverage, a food additive, and a beverage additive.

At this time, the food composition may contain, as an active ingredient, not only *Fomes fomentarius* extract but also ingredients that are ordinarily added in food production. For example, the food composition may contain proteins, carbohydrates, fats, nutrients, seasoning agents, and flavoring agents. Examples of the above-mentioned carbohydrates are monosaccharides such as glucose and fructose; disaccharides such as maltose, sucrose and oligosaccharides; and polysaccharides such as conventional glucose, e.g., dextrin and cyclodextrin and sugar alcohols such as xylitol, sorbitol, and erythritol. As a flavoring agent, natural flavoring agents [tau martin, stevia extract (e.g., rebaudioside A and glycyrrhizin) and synthetic flavoring agents (e.g., saccharin and aspartame) can be used.

In addition, when the food composition of the present disclosure is prepared as a drink, it may further contain citric acid, liquid fructose, sugar, glucose, acetic acid, malic acid, juice, an *eucommia ulmoides* oliver extract, a jujube extract, a licorice extract, and etc.

Further, the present disclosure provides a method for treating a cranial nerve disease, including the step of administering a pharmaceutically effective amount of the above composition, i.e., a *Fomes fomentarius* extract, a fraction thereof, or a compound isolated therefrom, to a mammal other than a human suffering from the cranial nerve disease.

In addition, the present disclosure provides a method for preventing a cranial nerve disease, including the step of administering the composition to a subject.

In the method of the present disclosure, in addition to the *Fomes fomentarius*, the present disclosure may further include at least one selected from the group consisting of *berchemia* berchemiaefolia, *Acer tegmentosum maxim*, and *Lithospermum erythrorhizon*.

In this method, the composition can be administered orally or parenterally at the time of administration and can be used in the form of a general pharmaceutical preparation. That is, the composition of the present disclosure can be administered in various formulations for oral and parenteral administration at the time of actual clinical administration. In the case of formulation, a diluent or excipient such as a filler, an extender, a binder, a wetting agent, a disintegrating agent and a surfactant usually used is used. Solid formulations for oral administration include a tablet, a pill, a powder, a granule and a capsule, which may be prepared by mixing the pharmaceutical composition of the present disclosure with at least one excipient such as starch, calcium carbonate, sucrose, lactose, and gelatin. In addition to simple excipients, a lubricant such as magnesium, styrate, and talc are also used. Liquid preparations for oral administration include a suspension, a solution, an emulsion, and a syrup. Various excipients such as a wetting agent, a flavoring agent, a fragrance, and a preservative may be included in addition to commonly used simple diluents such as water and liquid paraffin. Formulations for parenteral administration include a sterilized aqueous solution, a non-aqueous solution, a suspension, an emulsion, a freeze-dried preparation, and a suppository. Examples of the non-aqueous solution and the suspension include propylene glycol, polyethylene glycol, vegetable oil such as olive oil, injectable ester such as ethyl oleate, and the like. Witepsol, macrogol, tween 61, cacao paper, laurin butter, glycerol, and gelatin can be used as a base for suppositories. The composition of the present disclosure can be administered subcutaneously, intravenously, or intramuscularly on the parenteral administration.

The dosage unit may contain, for example, 1, 2, 3, or 4 times the individual dose or may contain ½, ⅓ or ¼ times the individual dose. The individual dosages preferably contain amounts in which the active drug is administered in a single dose, which usually corresponds to the full, half, one-third or one-fourth of the daily dose. The effective dose of the composition of the present disclosure is 0.0001 g/kg to 10 g/kg, preferably 0.0001 g/kg to 5 g/kg, and may be administered 1 to 6 times a day.

The composition of the present disclosure may be used alone or in combination with methods using a surgery, hormone therapy, chemotherapy, and biological response modifier for the prevention and treatment of a cranial nerve disease.

Hereinafter, the present disclosure will be described in detail with reference to Examples, but the scope of the present disclosure is not limited to the following Examples.

MODE FOR CARRYING OUT THE INVENTION

Example 1

Confirmation of Treatment Effect of Cranial Nerve Disease with *Fomes Fomentarius* Extract <1-1> Production of *Fomes Fomentarius* Extract

*Fomes fomentarius* purchased from Busan Pharmtekbio Co., Ltd. was dried and pulverized in a freeze dryer to prepare powders. The *Fomes fomentarius* powder was repeatedly extracted 5 times with 10 times volume (w/w) of 50% ethyl alcohol aqueous solution for 10 hours using ultrasonic waves, and the mixture was immediately filtered and concentrated in vacuum, and dextrin was mixed by a blending ratio and freeze-dried so that the extract (FFE) was obtained. At this time, the temperature during the concentration was kept at 45° C. or lower so as to prevent decomposition and hydrolysis of the constituents. By extraction using the above method, all substituent groups such as the sugar (the monosaccharide to the polysaccharide) and the methyl group ($-CH_3$) bonded to the aglycon can be extracted in non-decomposed forms.

<1-2> Measurement of Cytotoxicity of *Fomes Fomentarius* Extract on Nerve Cell (1) Cell Culture BV-2 cells, a microglial cell of rodent nerve, were obtained from the Graduate School of Pharmacy, Inje University. DMEM supplemented with 10% fetal bovine serum (FBS) and 1% penicillin/streptomycin was used as the culture medium. The wetness of $CO_2$ (2-5%) was maintained at 37° C. Two hours before the experiment, the medium was changed to a low serum culture medium (DMEM with 1% FBS).

(2) Microglial Cell Conditioned Medium

Lipopolysaccharide (LPS) was purchased from Sigma and dissolved in phosphate buffered saline (PBS, pH 7.4) to be used.

BV-2 microglial cells were stimulated with LPS (100 ng/mL) for 24 hours in the presence or absence of the prepared *Fomes fomentarius* extract.

The used culture medium was centrifuged to remove the detached cells collected from the culture dish. A supernatant was then used as conditioned medium.

The following four conditioned medium groups were set.

1) Control: conditioned medium of BV-2 cell group
2) Vehicle: conditioned medium of BV-2 cell group treated with LPS
3) FFE: conditioned medium treated with the *Fomes fomentarius* extract on LPS-treated BV-2 cell group
4) Positive Control: conditioned medium treated with the positive drug on LPS-treated BV-2 cell group (3) Measurement of Cytotoxicity on Microglial Cell Conditioned Medium In order to examine the cytotoxicity of the *Fomes fomentarius* extract to the nerve cells, the BV-2 cells were treated in groups of conditioned medium for 48 hours, and the *Fomes fomentarius* extract prepared in Example 1 was added thereto, and then the viability of microglial cells was measured by MTT assay at 6, 12, 18, 24, and 48 hours.

Specifically, the MTT assay was carried out by measuring the cell viability effects using MTT [3-(4,5-dimethylthiazol-2-yl)-2,5-diphenyltetrazolium bromide), the absorbance was continuously measured at 540 nm using a microplate reader (Model 550, Bio-Rad, USA), and the results are shown in FIG. 1.

Referring to FIG. 1, it was confirmed that the *Fomes fomentarius* extract did not exhibit cytotoxicity to nerve cells at its concentration of 40 µg/mL or less.

<1-3> Inhibitory Effect on Release of Pro-Inflammatory Cytokine in LPS-Stimulated Microglial Cell In the present example, the inhibitory effect of *Fomes fomentarius* extract on the secretion of pro-inflammatory cytokines such as IL-6 and TNF-α was measured in LPS-stimulated BV-2 microglial cells.

Specifically, BV-2 microglial cells were stimulated with LPS (100 ng/mL) for 24 hours in the presence or absence of the *Fomes fomentarius* extract. The *Fomes fomentarius* extract was pre-treated 2 hours before the co-treatment of LPS. The level of cytokine in the culture medium was then measured using an enzyme-linked immunosorbent assay (ELISA) kit. At this time, the amount of pro-inflammatory cytokine (IL-6 and TNF-α) released into the culture medium was collected by centrifugation of the supernatant of the medium, and the supernatant was measured using ELISA kit according to the instruction of the manufacturer (R&D, USA). The results are shown in FIG. 2.

Referring to FIG. 2, IL-1β and TNF-α levels were rapidly increased in the culture medium of LPS-stimulated BV-2 cells. On the other hand, it was confirmed that the concentration of pro-inflammatory cytokine was effectively suppressed in the case of the *Fomes fomentarius* extract-treated group according to the present example. In particular, on FFE 40 µg/ml treated group, the level of IL-1β was inhibited by 804±15.1% compared with the LPS-stimulated experimental group and the level of TNF-α was inhibited by 429±11.8% compared with the LPS-stimulated experimental group. Therefore, the levels of IL-1β and TNF-α are significantly inhibited in the *Fomes fomentarius* extract-treated group. Therefore, it is known that the *Fomes fomentarius* extract inhibits the generation of a potential neurotoxic cytokine in the microglial cells so that it is useful for prevention and treatment of dementia.

<1-4> In Vivo Animal Behavior Test for Cognitive Function Protective Effect (1) Experimental Animal and Induction of Animal Group with Cognitive Function Declined Male SD rats were used as experimental animals, which were provided from Orientbio (Busan, Korea) and were 5-week rats having a range of 100 g to 120 g. The experimental animals were housed and raised in plastic cages in a cage kept constantly at a temperature of 23±2° C. and a humidity of 50±10% and a 12-hour light/dark cycle, and unlimited feeds and water were supplied during the adaptation period.

Further, the experimental animals were adapted for 14 days in the laboratory, and then used by separating into the normal group, the control group, the vehicle, the pre-treatment *Fomes fomentarius* extract high-concentration orally administered group (200 mg/kg $rat_{weight}$), the pre-treatment *Fomes fomentarius* extract low-concentration orally administered group (100 mg/kg $rat_{weight}$), the post-treatment *Fomes fomentarius* extract high-concentration orally administered group (200 mg/kg $rat_{weight}$), the post-treatment *Fomes fomentarius* extract low-concentration orally administered group (100 mg/kg $rat_{weight}$), and the positive control group (Donepezil 0.5 mg/kg $rat_{weight}$), respectively.

At this time, the pre-treatment *Fomes fomentarius* extract group started the oral administration at 10:00 am once a day from 2 weeks before the induction of dementia, and the extract was continuously oral-administered once a day for 90 days after the induction of the disease. The pre-treatment *Fomes fomentarius* extract group started the administration after the induction of dementia, and they were orally administered once a day for 90 days as the pre-treatment group.

In order to induce the animal group with cognitive function declined, scopolamine dissolved in physiological saline was administered intraperitoneally to animals in all animal groups except the normal group at a dose of 1.5 mg/kg 1 hour before the memory test. After 7 times administration of scopolamine for 14 days at intervals of two days, the cognitive function was lost in the experimental group, which was confirmed by the Morris water maze test. Thus, it was confirmed that the animal model of dementia disease was completed.

(2) Morris Water Maze Test

Morris water maze test was carried out as described in Behav. Brain Res (155, 185-196). The water tank used in the water maze test was a cylindrical water tank with a diameter of 95 cm and a height of 50 cm and was filled with 23±2° C. water to which an ink was diluted during the test. A transparent platform was installed at 2 cm below the water surface in the water tank, and four markers were placed outside the water tank. The movement trajectories of animals were analyzed through a video tracking system and the latency of finding the transparent platform and the tendency and frequency of traversing each quadrant were analyzed to confirm the protection and maintenance effects of the cognitive function of the animals. The results of the analysis are shown in FIG. 3.

Referring to FIG. 3, the scopolamine-induced amnestic animal experimental group (vehicle) in the SD rats showed a significantly lower time latency of finding the platform, which was an increased result in compared to the control group. However, in the *Fomes fomentarius* extract-administered experimental group, a significantly lower latency was showed compared to the animal experimental group (vehicle). In other words, it can be confirmed that the *fomes fomentarius* extract is effective in protecting and improving cognitive function. Especially, the group administered with 200 mg/kg of the *Fomes fomentarius* extract showed an improvement of 293±3.2% compared with the experimental group and the group administered with 100 mg/kg of the *Fomes fomentarius* extract showed an improvement of 226±5.2% compared with the experimental group. Therefore, it can be confirmed from the present example that the *Fomes fomentarius* extract has effects of protection and maintenance of cognitive function.

(3) Forced Swimming Test (FST)

After having the environment adaptation period for the breeding room for one week, the first forced swimming test was carried out for 15 minutes to have adaptation period. After 24 hours, the second forced swimming test was performed for 5 minutes, and oral administration of the *Fomes fomentarius* extract was performed 30 minutes before the test. The *Fomes fomentarius* extract was orally administered once a day for 5 days and the final forced swimming test was carried out for 5 minutes before sacrifice.

At this time, each experimental animal group was classified as follows.

Group I: physiological saline orally administered group (control, n=10)
Group II: forced swimming test group (vehicle, n=10)
Group III: forced swimming test+*Fomes fomentarius* extract (200 mg/kg (rat$_{weight}$)) orally administered group (n=10)
Group IV: forced swimming test+*Fomes fomentarius* extract (100 mg/kg (rat$_{weight}$)) orally administered group (n=10)
Group V: forced swimming test+positive control (Donepezil 0.5 mg/kg (rat$_{weight}$)) orally administered group (n=10)

Specifically, the forced swimming test is a short-term sudden stress test on animal using the animal's ecological habit of 'water horror,' and thus the immobility time and the mobility time on the water has been separately measured on the animal. The results of sudden stress-related behavior are related to stress-induced overexpression of NF-κB in the brain, which is closely related to the cognitive ability of biologic changes and maintenance of bio homeostasis. The measurement results are shown in FIG. 4.

Referring to FIG. 4, the animal experimental group (vehicle) in which the forced swimming test was performed in the SD species rats showed a pattern of 140 seconds in the first trial and 120 seconds in the second trial. However, in the *Fomes fomentarius* extract-treated experimental group, the immobility time was significantly lower than that of the animal experimental group (vehicle). In other words, it was confirmed that the *Fomes fomentarius* extract was effective in protecting and improving stress. In particular, 200 mg/kg of the *Fomes fomentarius* extract-administered group showed an improvement of 202±7.2% compared with that of the experimental group, and 100 mg/kg of the *Fomes fomentarius* extract-administered group showed an improvement of 173±6.5% compared to the experimental group. Therefore, it can be confirmed from the present example that the *Fomes fomentarius* extract is effective in protecting and improving stress.

<1-5> Animal PET-CT Using $^{18}$F-FDG

As dementia progresses, the activity of glucose metabolism in each region of the brain decreases as the activity of the brain cells decreases or ceases to exist, which is used as a quantitative test for a function evaluation of anatomically functional brain on each brain region in the clinical practice. In this regard, objective information on dementia and information on quantitative brain activity can be obtained using the degree of glucose metabolism in the brain by $^{18}$F-fluorodeoxyglucose ($^{18}$F-FDG). In the present example, the brain activity maps for the experimental animals were confirmed. In this regard, the degree of glucose metabolism was analyzed and quantitated using Pmod 3.6, View computer program with animal PET-CT (SIEMENS Inveon, Germany). At this time, the experimental animal group was the same as example 4-(1). The measurement results are shown in Table 1 and FIG. 5.

Specifically, FIG. 5a shows the results of animal PET-CT imaging of the tomo-parts of the brain. Referring to FIG. 5a, the glucose metabolism of the scopolamine-induced dementia disease group (vehicle, Alzheimer's disease, AD) was significantly lowered in the overall brain compared to that of the normal group. On the other hand, the levels of glucose metabolism of both the pre-treatment *Fomes fomentarius* extract-administered group and the post-treatment *Fomes fomentarius* extract-administered group were significantly elevated compared to that of the dementia disease group (vehicle, Alzheimer's disease, AD). The *Fomes fomentarius* extract was found to be effective in preventing and treating dementia.

Further, FIGS. 5b to 5d are graphs that quantitatively show the relative comparison of the brain's glucose uptake on each part of the brain. In this case, FIG. 5b shows the normal group, the dementia disease group (vehicle, Alzheimer's disease, AD), the pre-treatment *Fomes fomentarius* extract high-concentration orally administered group (200 mg/kg rat$_{weight}$), the pre-treatment *Fomes fomentarius* extract low-concentration orally administered group (100 mg/kg rat$_{weight}$), and the positive control administered group (Donepezil). FIG. 5c shows the normal group, the disease group, the post-treatment *Fomes fomentarius* extract high-concentration orally administered group (200 mg/kg rat$_{weight}$), and the post-treatment *Fomes fomentarius* extract low-concentration orally administered group (100 mg/kg rat$_{weight}$). FIG. 5d shows incorporation of FIGS. 5b and 5c.

In addition, the parts of the brain displayed on the X-axis in the graph are shown in Table 1 below.

Referring to this, the scopolamine-induced dementia disease group (AD) showed significantly lower levels of glucose metabolism in the cerebral cortex area (7 to 30) of the brain. Compared with this, the pre-treatment *Fomes fomentarius* extract high-concentration administered group (pre-high) showed the improved effect of 240±2.8% compared with the dementia disease group (AD), and the post-treatment *Fomes fomentarius* extract low-concentration administered group (post-low) showed the improved effect of 187±5.5% compared with the dementia disease group (AD). That is, it can be confirmed that the *Fomes fomentarius* extract has an effect on the prevention and the treatment of dementia.

TABLE 1

1. Accumbens_l
2. Accumbens_r
3. Amygdala l
4. Amygdala r
5. Striatum l
6. Striatum r
7. AuditoryCortex l
8. Auditory Cortex r
9. Cingulate Cortex l
10. Cingulate Cortex r
11. Entorhinal Cortex l

TABLE 1-continued

12. Entorhinal Cortex r
13. Frontal Association Cortex l
14. Frontal Association Cortex r
15. Nsular Cortex l
16. Nsular Cortex r
17. Medial Prefrontal Cortex l
18. Medial Prefrontal Cortex r
19. Motor Cortex l
20. Motor Cortex r
21. Orbitofrontal Cortexl l
22. Orbitofrontal Cortexl r
23. ParACortex l
24. ParACortex r
25. Retrosplenial Cortex l
26. Retrosplenial Cortex r
27. Somatosensory Cortex l
28. Somatosensory Cortex r
29. Visual Cortex l
30. Visual Cortex r
31. Hippocampus AnteroDorsal l
32. Hippocampus AnteroDorsal r
33. Hippocampus Posterior l
34. Hippocampus Posterior r
35. Hypothalamus l
36. Hypothalamus r
37. Olfactory l
38. Olfactory r
39. Colliculus Superior l
40. Colliculus Superior r
41. Midbrain l
42. Midbrain r
43. Ventral Tegmental Area l
44. Ventral Tegmental Area r
45. Cerebellum GM l
46. Cerebellum GM r
47. Cerebellum WM l
48. Cerebellum WM r
49. Colliculus Inferior l
50. Colliculus Inferior r
51. Thalamus l
52. Thalamus r
53. Pituitary
54. Cerebellum-blood
55. Central Canal-PAG
56. Pons
57. Septum
58. Medulla <1-6> Control Effect of Inflammatory Cytokine by Administration of *Fomes Fomentarius* Extract to Scopolamine Dementia-Induced Group The inhibitory effect of *Fomes fomentarius* extract on the secretion of pro-inflammatory cytokines such as IL-6 and TNF-α was measured in the scopolamine dementia-induced group.

Specifically, blood was collected using heparinized syringes in the abdominal vein after sacrifice of animals. The collected blood was centrifuged at 3,000 rpm for 15 minutes, and plasma was collected. The collected plasma was measured by an enzyme-linked immunosorbent assay (ELISA) kit according to the manufacturer's instructions (R&D, USA).

At this time, the experimental animal group was the same as Example 4-(1). The measurement results are shown in FIG. 6.

Referring to FIG. 6, it can be confirmed that the levels of IL-1β and TNF-α in the scopolamine-induced dementia group increased sharply, but the levels of pro-inflammatory cytokines were effectively suppressed in the experimental group treated with the *Fomes fomentarius* extract. In particular, it was showed that the levels of IL-1β and TNF-α, respectively, in the high-concentration pre-treatment *Fomes fomentarius* extract-administered group was significantly inhibited by 658±21.4% and 290±14.5% compared to the dementia-induced group, and similarly, the levels of IL-1β and TNF-α, respectively, in the high-concentration post-treatment *Fomes fomentarius* extract-administered group was significantly inhibited by 416±34.1% and 245±21.1% compared to the dementia-induced group.

Therefore, it can be confirmed from the results of the above examples that the *Fomes fomentarius* extract is useful for the prevention and treatment of dementia by inhibiting the generation of potential neurotoxic cytokines in the scopolamine dementia-induced experimental group.

<1-7> Inhibitory Effect on MAPKs Phosphorylation in Brain Parenchymal Tissue of Dementia-Induced Animal Group Oxidation of mitroken-activated protein kinases (MAPKs) is known to be critical for LPS-induced activation of a pro-inflammatory adjusting agent that initiates an inflammatory process. Oxidation of mitroken-activated protein kinases (MAPKs) against the signal transmission cascade of microglial cells activation is known to be critical for LPS-induced activation of a pro-inflammatory adjusting agent that initiates an inflammatory process. In particular, MAPKs are known to be involved in the expression of inflammatory genes such as IL-6, TNF-α, and iNOS.

The protein expression is directly related to the activation of microglial cells of the brain. In the present example, the *Fomes fomentarius* extract was directly administered orally over 70 days in order to confirm the effect of the *Fomes fomentarius* in vivo through animal experiments. It was to confirm effects of the *Fomes fomentarius* extract on the protection and improvement of cognitive function in this regard.

Specifically, after 2 weeks of administration of scopolamine (1.5 mg/kg), the *Fomes fomentarius* extract-administered group was tested to confirm the therapeutic effect of the extract on diseases. Before the administration of scopolamine, the *Fomes fomentarius* extract-administered group was tested to examine the preventive effect against diseases. After 70 days of experiment, animal behavioral evaluation of each animal and animal PET-CT results were combined to evaluate cognitive function protection and therapeutic effect. Animals were sacrificed on the $70^{th}$ day, and the phosphorylation of p38 was evaluated by Western blot in brain tissue and medulla oblongata. The measurement results are shown in FIG. 7.

Referring to FIG. 7, it can be confirmed that the level of p38 in the scopolamine-induced dementia disease model was dramatically increased, and the expression of the protein was effectively inhibited in the *Fomes fomentarius* extract-administered group. In particular, it was measured that in the case of the high-concentration pre-treatment *Fomes fomentarius* extract-administered group, the phosphorylation of p38 was significantly inhibited by 248±5.8% in the spinal cord and 229±8.1% in the medulla oblongata. It was measured that in the low-concentration post-treatment *Fomes fomentarius* extract-administered group, the phosphorylation of p38 was significantly inhibited by 291±4.9% in the spinal cord and 238±8.9% in the medulla oblongata. Therefore, it can be confirmed from the results of the present example that the *Fomes fomentarius* extract suppresses the phosphorylation of p38 to have effects for the prevention and treatment of dementia.

<1-8> Inhibitory Effect on NF-κB Signal Transmission in Brain Parenchymal Tissue of Dementia-Induced Animal Group NF-κB plays a key role in the inflammatory response by adjusting and elevating the pro-inflammatory mediator. Because the promoter region of the gene encoding iNOS contains the NF-κB binding site, blocking of NF-κB nucleus translocation inhibits iNOS gene expression. In addition, the expression of pro-inflammatory cytokines such as IL-6 and TNF-α is regulated by NF-κB.

The protein expression is directly related to the activation of the microglial cells of the brain. In the present example, *Fomes fomentarius* extract was directly administered orally over 70 days in order to confirm the effect of the *Fomes fomentarius* in vivo through animal experiments. It is to confirm the effect of the *Fomes fomentarius* extract on the protection and improvement of cognitive function in this regard.

Specifically, after 2 weeks of administration of scopolamine (1.5 mg/kg), the *Fomes fomentarius* extract-administered group was tested to confirm the therapeutic effect of the extract on diseases. Before the administration of scopolamine, the *Fomes fomentarius* extract-administered group was tested to examine the preventive effect against diseases. After 70 days of experiment, animal behavioral evaluation of each animal and animal PET-CT results were combined to evaluate cognitive function protection and therapeutic effect. Animals were sacrificed on the $70^{th}$ day, and the signal transmission of NF-κB was evaluated by Western blot in brain tissue and medulla oblongata. The measurement results are shown in FIG. 8.

Referring to FIG. 8, it can be confirmed that the value of NF-κB p65 protein in the scopolamine-induced dementia disease model was dramatically increased, and the expression of the protein was effectively inhibited in the *Fomes fomentarius* extract-administered group. In particular, it was measured that in the high-concentration pre-treatment *Fomes fomentarius* extract-administered group, it was significantly weakened by 493±7.2% in the spinal cord, and in the high-concentration post-treatment *Fomes fomentarius* extract-administered group, it was significantly weakened by 229±11.5% in the spinal cord. Further, it was measured that in the high-concentration pre-treatment *Fomes fomentarius* extract-administered group, it was significantly weakened by 244±8.0% in the medulla oblongata, and in the high-concentration post-treatment *Fomes fomentarius* extract-administered group, it was significantly weakened by 169±13.8% in medulla oblongata. Therefore, it can be confirmed from the results of the present example that the *Fomes fomentarius* extract suppresses the NF-κB p65 protein to have effects for the prevention and treatment of dementia.

As described above, the *Fomes fomentarius* extract according to the present disclosure can inhibit the generation of potential neurotoxic cytokines of microglial cells without showing cytotoxicity at a low concentration. Further, from the above-mentioned animal test results, the *Fomes fomentarius* extract may have effects on protection and improvement of cognitive function and protection and improvement of on stress. In addition, from the imaging results of animal PET-CT, it was confirmed that the *Fomes fomentarius* extract can be effectively applied to the prevention and treatment of dementia by increasing the glucose metabolism activity in the cerebral portion of the brain in particular. Further, it can be confirmed that the *Fomes fomentarius* extract can be effectively applied to the prevention and treatment of dementia by showing effects of adjusting inflammation cytokines and inhibiting MARKs phosphorylation and NF-κB signal transmission. Therefore, the *Fomes fomentarius* extract of the present disclosure is considered to be very usefully applied to prevention or treatment of cranial nerve diseases.

Example 2

Confirmation of Therapeutic Effect of *Fomes Fomentarius* Fraction on Cranial Nerve Disease <2-1> Method of Fractioning Solvent of *Fomes Fomentarius* Extract 15 g of a *Fomes fomentarius* methanol extract was dissolved in 800 ml of distilled water to be placed on a separate funnel, and 800 ml of hexane was added and stirred so that the two solvents were mixed well. Then, after confirming that the layers of the two solvents were clearly separated, the distilled water layer in the lower layer was transferred and put to another separate funnel so that 800 ml of a hexane layer was obtained. 800 ml of chloroform was poured into the distilled water layer transferred and put, and the mixture was stirred in the same manner as hexane and then was separated so that 800 ml of a chloroform layer was obtained. As the above method, 800 ml of ethyl acetate was poured into the remaining distilled water layer to obtain 800 ml of an ethyl acetate layer. Finally, 800 ml of butyl alcohol was poured into the distilled water layer to obtain 800 ml of a butyl alcohol layer and 800 ml of a distilled water layer (See FIG. 9).

<2-2> Measurement of DPPH Radical Scavenging Activity of *Fomes Fomentarius* Fraction The present experiment used the property that the hydrazyl of diphenylpicrylhydrazyl (DPPH) used in the present experiment has a property of easily accepting a hydrogen atom since the nitrogen atom is unstable, so as to react with the antioxidant material to accept the hydrogen atom to lose its own orthochromatism.

First, in order to measure DPPH radical scavenging activity of the *Fomes fomentarius* fraction, 1.9 ml of 0.2 mM DPPH solution (99.5% ethanol) was added to 0.1 ml of solutions (control: 99.5% ethanol) in which the concentrated dried material of each *Fomes fomentarius* substance was prepared at 7 concentrations of 10, 20, 40, 80, 160, 320 and 640 μg/ml, respectively. The mixture was shaken with a vortex mixer for 10 seconds and then incubated at 37° C. for 30 minutes. Then, the absorbance was measured at 517 nm using a spectrophotometer.

As a positive control drug, L-ascorbic acid was prepared at 6 concentrations of 10, 20, 40, 80, 160, 320, and 640 μg/mL (99.5% ethanol). The antioxidant activity of each sample was showed as % antioxidant activity (electron donating ability) against DPPH.

As a result, the ascorbic acid, which is a positive substance, was concentration-dependently increased as 70.5±4.5, 71.8±12.5, 74.1±8.2, 77.8±7.6, 80.6±4.5, 83.2±9.6, and 84.5±7.7, respectively, as the concentration was increased as 10, 20, 40, 80, 160, 320, and 640 μg/mL. It can be indicated that there were concentration-dependent increases despite the differences in all concentrations as the hexane fractions had 0.9±0.1, 1.8±0.2, 0.8±0.1, 1.9±0.3, 3.1±0.2, 1.9±0.3, and 3±0.1, the CHCl₃ had 11.2±1.8, 13.5±2.3, 16.5±1.9, 22.1±2.4, 30.6±3.5, 33.7±2.6, and 35.8±3.8, the EtOAc factions had 1.8±0.2, 3.1±0.4, 2.9±0.1, 5.1±0.3, 3.8±0.1, 3.1±0.2, and 4.2±0.4, the BuOH factions had 3.8±0.3, 5.1±0.4, 6.1±0.6, 8.9±0.5, 10.6±0.1, 10.8±0.4, and 11.4±0.3, and the water factions had 5.1±0.2, 7.1±0.1, 11.1±0.3, 12.5±0.4, 15.3±0.3, 15.8±0.2, and 16.3±0.6. (See FIG. 10).

<2-3> Measurement of Xanthine Oxidase Inhibitory Activity of *Fomes Fomentarius* Fraction 0.2 ml of the substrate solution in which 2 mM xanthine was dissolved was added to 0.1 ml of a sample solution and 0.6 ml of 0.1 M potassium phosphate buffer at pH 7.5, and 0.1 ml of 0.2 unit/ml xanthine oxidase was added thereto, followed by reaction at 37° C. for 5 minutes. Then, 1 ml of 1N HCl was added to terminate the reaction, and then the absorbance of the uric acid produced in the reaction solution was measured at 292 nm. The inhibitory activity of xanthine oxidase was shown by the absorbance reduction rate of the addition group and the non-addition group of the sample solution.

Xanthine oxidase acts as a rate-limiting enzyme in the terminal oxidation of all purines and is an enzyme that acts as a source of oxidizing agents such as superoxide radicals and hydrogen peroxide. The superoxide anion inhibition by xanthine/xanthine oxidase enzymes is shown by superoxide anion scavenging activity and xanthine oxidase inhibition and has biologically important meaning through inhibition of gout and formation of free radicals. The superoxide radical scavenging effects of 10, 20, 40, 80, 160, 320, and 640 μg mL-1 of each fraction extract of the *Fomes fomentarius* were compared using butylated hydroxy anisole (BHA) as a positive control group. BHA (butylated hydroxyanisole), which is a positive substance, was concentration-dependently increased to 24.1±0.1, 35.8±0.3, 58.1±0.4, 68.1±0.5, 76.1±0.8, 83.5±1.2, and 85.6±1.3, respectively, as the concentration was increased as 10, 20, 40, 80, 160, 320, and 640 μg/mL. There were concentration-dependent increases despite the differences in all concentrations as the hexane fractions had 0.8±1.8, 1.5±3.1, 3.5±4.1, 5.1±2.9, 4.9±3.1, 5±4.5, and 5.4±3.8, the $CHCl_3$ had 12.5±0.5, 18.5±0.6, 20.1±0.2, 22.1±0.4, 31.9±1.1, 36.5±0.3, and 40.5±0.8, the EtOAc factions had 1.5±0.4, 3.5±0.6, 3.8±0.3, 4.5±0.2, 4.1±0.6, 5±0.4, and 5.3±0.8, the BuOH factions had 2.1±0.9, 4.1±1.1, 4.8±1.6, 5.9±1.5, 8.1±2.1, 9.4±2.2, and 11.5±3.5, and the water factions had 8.1±1.8, 9.9±2.5, 11.5±0.9, 13.5±1.1, 15.5±2.5, 16.1±3.5, 16.4±2.8.

As a result, it was found that all *Fomes fomentarius* fractions had a high inhibition rate of xanthine oxidase, and among them, the *Fomes fomentarius* chloroform ($CHCl_3$) fraction showed the highest inhibitory effect of xanthine oxidase (See FIG. 11). In addition, it was confirmed that the inhibitory rate effect of xanthine oxidase was meaningfully good in the concentration of the *Fomes fomentarius* fraction <2-4> Measurement of Inhibitory Activity of Acetylcholinesterase of *Fomes Fomentarius* Fraction AChE and acetylthocholine iodine (ATC) were dissolved in 100 mM phosphate buffer (pH 8.0) to prepare 0.25 U/mL and 75 mM, respectively. The chromogenic reagent was prepared such that 39.6 mg of DTNB [5,5-dithiobis (2-nitrobenzoic acid)] and 15 mg of sodium bicarbonate were dissolved in 10 mL of 100 mM phosphate buffer (pH 8.0). 2.8 mL of phosphate buffer (100 mM, pH 8.0), 30 μL of AChE (0.25 U/mL), and 100 μL of DTNB were added to 30 μL of the extract, and were mixed. Then, the mixture was preincubated at 37° C. for 10 minutes. Then, 30 μL of substrate ATC was added thereto and was reacted at 37° C. for 3 minutes, and then the absorbance was measured at 412 nm. As a control group, 30 μL of 100 mM phosphate buffer (pH 8.0) was added instead of the extract, and then was measured. The formula calculated the inhibitory activity: acetylcholinesterase inhibitory activity (%)=[1−(CAbs−SAbs)/(CAbs−BAbs)]×100: "CAbs: absorbance of the control group, SAbs: sample absorbance, BAbs: absorbance of sample non-addition group." AChE inhibitory effects of 10, 20, 40, 80, 160, 320, and 640 μg mL-1 of each fraction extract of *Fomes fomentarius* were compared using TA (Tacrine) as a positive control.

As a result, TA (Tacrine), which is a positive control substance group, was concentration-dependently increased as 35.8±3.5, 45.1±4.5, 51.8±6.5, 61.1±4.1, 61.9±3.8, 76.1±4.6, and 87.9±5.6, respectively, as the concentration was increased to 10, 20, 40, 80, 160, 320, and 640 μg/mL. There were concentration-dependent increases despite the differences in all concentrations as the hexane fractions had 8.1±0.8, 13.1±1.2, 14.1±2.6, 15.4±1.5, 16.1±0.9, 17.8±2.1, and 18.1±3.5, the $CHCl_3$ had 13.2±1.8, 22±2.1, 24.1±0.9, 25.9±2.5, 32.1±1.5, 34.1±3.5, and 35.1±4.8, the EtOAc factions had 6.1±0.9, 6.6±2.1, 7.1±0.5, 8.6±1.2, 9.5±1.6, 10.3±0.9, and 11.8±2.1, the BuOH factions had 5.8±2.1, 7.1±3.1, 8.7±1.9, 9.5±3.1, 10.9±2.8, 12.5±3.5, and 14±4.2, and the water factions had 11.8±1.8, 16.1±2.1, 17.5±3.5, 18.1±4.1, 19.9±0.9, 23.1±2.1, and 21.1±1.9. (See FIG. 10).

As a confirmation result, it was found that all of the *Fomes fomentarius* fractions exhibited high acetylcholinesterase inhibitory activity, and that among them, the *Fomes fomentarius* chloroform ($CHCl_3$) fraction exhibited the highest acetylcholinesterase inhibitory effect (See FIG. 12). In addition, it was confirmed that the inhibitory effect of acetylcholinesterase was meaningfully good in the concentration of the *Fomes fomentarius* fractions.

<2-5> Fractionation and Separation of *Fomes Fomentarius* $CHCl_3$ Fractions by Thin Layer Chromatography (TLC)

In the qualitative analysis by TLC, the lyophilized powder of the *Fomes fomentarius* $CHCl_3$ extract was dissolved in 80% methanol, and filtered through a 0.45 μm syringe filter (Whatman, Rockland, Mass., USA), and used as a sample for TLC analysis. Each sample was drop the silica plate (aluminum sheet silica gel60 F254, Merck, Darmstadt, Germany), and was deployed as mixed solvent of toluene/acetone/formic acid (6:6:1. v/v/v). Component identification was confirmed by the Rf value of each component and the color of the band using ultraviolet light (UV-254 nm, UV-366 nm). The following four fractions were selected.

1 fraction: Rf (0.08) was 12.1±0.6, Rf (0.13) was 5.6±0.8, Rf (0.27) was 25.6±2.1 and Rf (0.37) was 11.5±1.9%.

Further, the following experiments were conducted on two substances, nonadecanone (2-Nonadecanone), and docosenol (cis-13-Docosenol), which are expected to Rf (0.27) in the present disclosure.

<2-6> Measurement of DPPH Radical Scavenging Activity of Two Kinds of Compounds of the Present Disclosure The present inventors measured DPPH radicals scavenging activity in the same manner as in Example <2-2> above using nonadecanone (2-nonadecanone) and docosenol (cis-13-Docosenol) compounds found in the above and *Fomes fomentarius* $CHCl_3$ fraction of the present disclosure.

As a result, the ascorbic acid, which is a positive control substance group, was concentration-dependently increased as 70.5±4.5, 71.8±12.5, 74.1±8.2, 77.8±7.6, 80.6±4.5, 83.2±9.6, and 84.5±7.7, respectively, as the concentration was increased as 10, 20, 40, 80, 160, 320, and 640 μg/ml. There were concentration-dependent increases despite differences in all concentration as the nonadecanone (2-Nonadecanone) had 5.6±0.9, 8.9±0.8, 11.6±1.1, 13.5±1.4, 14.6±1.0, 16.8±2.1, and 20.5±1.8, and the docosenol (cis-13-Docosenol) compound had 1.3±0.4, 2.6±0.2, 5.8±0.6, 7.7±0.6, 6.6±0.7, 8.8±1.1, and 10.6±0.9.

As a confirmation result, it can be found that the high DPPH radical scavenging activity was also found in the nonadecanone (2-Nonadecanone) and the docosenol (cis-13-Docosenol) compounds of the present disclosure although it did not reach ascorbic acid, which is a positive control group. It was confirmed that the DPPH radical scavenging activity was slightly higher in the nonadecanone (2-Nonadecanone) among the two compounds (See FIG. 15).

<2-7> Measurement of Xanthine Oxidase Inhibitory Activity of Two Kinds of Compounds of the Present Disclosure The present inventors measured xanthine oxidase inhibitory activity using the nonadecanone (2-Nonadecanone) and the docosenol (cis-13-Docosenol) compounds and the *Fomes fomentarius* $CHCl_3$ fraction of the present disclosure in the same manner as in Example <2-3>.

As a result, the ascorbic acid, which is a positive control substance group, was concentration-dependently increased as 24.1±1.8, 35.1±2.5, 58.1±0.9, 68.1±1.1, 76.1±2.5, 83.5±3.5, and 85.6±2.8, as the concentration was increased as 10, 20, 40, 80, 160, 320, and 640 µg/ml. There were concentration-dependent increases despite differences in all concentration as the nonadecanone (2-Nonadecanone) had 4.1±0.5, 6.9±0.8, 12.3±1.1, 20.5±0.9, 21.6±0.7, 24.6±1.1, and 30.8±1.4, and the docosenol (cis-13-Docosenol) compound had 0.9±0.3, 2.5±0.5, 3.6±0.7, 5.8±1.1, 7.7±0.9, 9.6±0.8, and 11.8±1.4.

As a confirmation result, it can be found that the high xanthine oxidase inhibitory activity was also found in the nonadecanone (2-Nonadecanone) and the docosenol (cis-13-Docosenol) compounds of the present disclosure although it did not reach ascorbic acid, which is a positive control group. It was confirmed that the xanthine oxidase inhibitory activity was slightly higher in the nonadecanone (2-Nonadecanone) among the two compounds (See FIG. 16).

<2-8> Measurement of Acetylcholinesterase Inhibitory Activity of Two Kinds of Compounds of the Present Disclosure The present inventors measured acetylcholinesterase inhibitory activity using the nonadecanone (2-Nonadecanone) and the docosenol (cis-13-Docosenol) compounds and the *Fomes fomentarius* $CHCl_3$ fraction of the present disclosure in the same manner as in Example <2-4>.

As a result, the ascorbic acid, which is a positive control substance group, was concentration-dependently increased as 35.8±3.5, 45.1±4.5, 51.8±6.5, 61.1±4.1, 61.9±3.8, 76.1±4.6, and 87.9±5.6, as the concentration was increased as 10, 20, 40, 80, 160, 320, and 640 µg/ml. There were concentration-dependent increases despite differences in all concentration as the nonadecanone (2-Nonadecanone) had 11.6±1.1, 18.9±0.9, 23.4±2.8, 30.1±1.8, 35.1±3.1, 41.5±2.2, and 41.9±3.8, and the docosenol (cis-13-Docosenol) compound had 18.1±2.6, 23.1±3.8, 28.41±1.9, 35.9±5.1, 40.9±6.8, 55.1±4.9, and 59.6±6.6.

As a confirmation result, it can be found that the acetylcholinesterase inhibitory activity was also found in the nonadecanone (2-Nonadecanone) and the docosenol (cis-13-Docosenol) compounds of the present disclosure although it did not reach slightly ascorbic acid, which is a positive control group. It was confirmed that the acetylcholinesterase inhibitory activity was slightly higher in the docosenol (cis-13-Docosenol) among the two compounds (See FIG. 17). It was also found that the inhibition rate of acetylcholinesterase was increased depending on the treatment concentration.

<2-9> Confirmation of Therapeutic Effect on Cranial Nerve Disease of Two Kinds of Compounds of the Present Disclosure (1) Cell Culture A mouse BV2 cell line was stored and maintained in a humidified incubator at 37° C. under a 5% $CO_2$ condition using a DMEM culture medium supplemented with 10% FBS, 100 U/ml of penicillin and 100 µg/ml of streptomycin, was trypsinized, and was subcultured.

(2) Measurement of NO (Nitric Oxide)

The mouse BV2 cell line used in the experiment is a microglial cell and an inflammatory cell present in the brain. Activated microglial cells secrete inflammatory mediators to induce the death of nerve cells. Therefore, suppressing the inflammatory response prevents nerve cell damage and further prevents the development and progression of degenerative brain diseases.

In the present disclosure, the amount of nitrite produced was measured to determine the anti-inflammatory activity of the *Fomes fomentarius* fraction. Nitrite is a major stable product of nitric oxide (NO), one of the inflammatory mediators, and was measured by using Griess reagent.

First, the cells were cultured at $5 \times 10^5$ cells/ml in a 6-well plate. They were treated with *Fomes fomentarius* extracts having various concentrations (5, 20, 50, and 100 µg/ml) and then reacted for 24 hours in the presence or absence of LPS (0.5 µg/ml). DMEM medium for BV2 cells and the fresh medium containing LPS (1 µg/ml) and the sample were treated at the same time and cultured for 24 hours. The amount of NO produced was determined using Griess reagent in which 100 µl of cell culture supernatant and 100 µl of Griess reagent [1% (w/v) sulfanilamide, 0.1% (w/v) naphthyl ethylenediamine in 2.5% (v/v) phosphoric acid] were mixed and reacted on a 96-well plate for 10 minutes, and then an ELISA reader was used to measure absorbance at 540 nm. Standard concentration curves were obtained by stepwise dilution of sodium nitrite ($NaNO_2$).

The $CHCl_3$ fractions were concentration-dependently decreased as 1.14±011, 10.15±1.25, 4.61±0.85, 2.76±0.25, 2.29±0.41, and 2.181±0.39 in the *Fomes fomentarius* extract (control, vehicle, 5, 20, 50, and 100 µg/ml). There were the concentration-dependent decreases despite differences in all concentrations as the nonadecanone (2-Nonadecanone) had 1.95±0.15, 10.25±2.09, 2.98±0.78, 2.35±0.68, 1.99±0.39, and 1.62±0.41, and the docosenol (cis-13-Docosenol) compound had 1.0±0.1, 10.54±1.81, 8.04±0.55, 5.56±0.61, 4.42±0.48, and 2.76±40.59.

As a result of examining the degree of NO production by the treatment of the *Fomes fomentarius* $CHCl_3$ fraction, the nonadecanone (2-Nonadecanone) and the docosenol (cis-13-Docosenol) compounds of the present disclosure, in the group in which inflammation was induced by LPS, the amount of NO production was about 5 times higher than that of the control group without any treatment. It can be confirmed that when the group in which inflammation was induced by LPS was treated with the *Fomes fomentarius* $CHCl_3$ fraction, the nonadecanone (2-Nonadecanone) and the docosenol (cis-13-Docosenol) compounds, a significantly reduced effect of NO production was showed in the entire concentration range (See FIG. 18).

(3) Measurement of Inflammatory Cytokine Inhibitory Activity

In the present disclosure, IL-1β, IL-6, and TNF-α were measured to confirm the degree of inflammatory cytokine inhibition of the *Fomes fomentarius* fraction. The $CHCl_3$ fraction of IL-1β was concentration-dependently decreased as 28.12±3.5, 89.51±9.1, 61.45±5.8, 51.45±6.1, 40.12±3.5, and 39.88±4.1 in the *Fomes fomentarius* extract (control, vehicle, 5, 20, 50 and 100 µg/ml). There were concentration-dependent decreases despite differences in all concentration as the nonadecanone (2-Nonadecanone) had 30.65±2.9, 91.81±3.5, 70.12±4.8, 65.56±5.1, 58.11±6.5, and 43.66±3.4, and the docosenol (cis-13-Docosenol) compound had 29.88±3.1, 87.12±5.5, 65.15±7.6, 59.12±6.1, 50.55±4.2, and 48.19±5.8. The $CHCl_3$ fraction of IL-6 was concentration-dependently decreased as 89.11±7.5, 489.23±21.2, 289.55±8.2, 254.13±10.2, 184.69±5.1, and 141.59±8.8 in the *Fomes fomentarius* extract (control, vehicle, 5, 20, 50 and 100 μg/ml). There were concentration-dependent decreases despite differences in all concentration as the nonadecanone (2-Nonadecanone) had 87.54±6.2, 475.66±19.5, 451.25±6.9, 441.61±7.1, 389.64±10.1, and 351.85±8.7, and the docosenol (cis-13-Docosenol) compound had 90.61±8.1, 491.25±25.1, 301.56±7.6, 249.35±10.1, 171.68±5.5, and 138.51±6.8. The $CHCl_3$ fraction of TNF-α was concentration-dependently decreased as 17.56±3.3, 95.15±9.0, 55.15±5.5, 43.12±6.0, 30.57±3.2, and 24.81±4.0 in the *Fomes fomentarius* extract (control, vehicle, 5, 20, 50 and 100 μg/ml). There were concentration-dependent decreases despite differences in all concentration as the nonadecanone (2-Nonadecanone) had 16.58±2.7, 91.89±3.3, 79.12±4.1, 70.24±5.0, 59.56±6.2, and 50.47±3.1, and the docosenol (cis-13-Docosenol) compound had 17.99±3.2, 93.47±5.6, 60.12±7.4, 40.58±6.2, 28.15±4.1, and 22.87±5.6.

As a measurement result of IL-1β, IL-6 and TNF-α, which are inflammatory cytokines by the treatment of the *Fomes fomentarius* $CHCl_3$ fraction, the nonadecanone (2-Nonadecanone), and the docosenol (cis-13-Docosenol) compounds of the present disclosure, in the group in which inflammation was induced by LPS, the inflammatory cytokine expression was showed about 3 to 5 times higher than that of the control group without any treatment.

It can be confirmed that when the group in which inflammation was induced by LPS was treated with the *Fomes fomentarius* $CHCl_3$ fraction, the nonadecanone (2-Nonadecanone) and the docosenol (cis-13-Docosenol) compounds, a significant reduced effect of IL-1β, IL-6 and TNF-α production was showed in the entire concentration range (See FIGS. 19 to 21).

(4) Western Blotting Analysis

BV2 cells were placed in a 6-well plate at $7.5 \times 10^5$ cells/well, and stabilized at 37° C. and 5.0% $CO_2$ for 12 hours. After that, LPS and the *Fomes fomentarius* $CHCl_3$ fractions, the nonadecanone (2-Nonadecanone) or the docosenol (cis-13-Docosenol) compounds were placed according to groups and were incubated for 1 hour. The cell culture was collected and used for cytokine analysis. All the cell culture was removed, and then 1 ml of dPBS was dispensed to each well to wash and remove the wells. 200 μl of the lysis buffer was dispensed per well and the cells attached to the bottom of the well were removed with a cell scriper, and then were slowly mixed and reacted for 30 on ice at 4° C. The cells were removed with a scriper again and all the lysis solution was collected. The collected lysis solution was centrifuged at 15,000 rpm for 15 minutes at 4° C. so that only the supernatant was collected. In order to plot standard curves for protein quantification, a standard BSA solution (2 g/1 ml, 1 g, 0.5 g, 0.25 g, 0.125 g, 0.0625 g) and a dilution were prepared in which bradford solution and D.W. were diluted with 4:1. After the bradford dilution was dispensed in each 200 μl to 96-well, the standard BSA solution and the cell lysis supernatant were dispersed in a volume of 10 μl per well, and then they were mixed by pipetting. After 10 minutes, the protein was quantitated by measuring the absorbance at 595 nm in a reader. The subsequent procedures were carried out in the same manner as in the quantitative analysis of the protein of Example 3-3.

As a confirmation result, p-NF-κB/NF-κB ratio (%) of the nonadecanone (2-Nonadecanone) showed 0% and 100% expression ratio, respectively, in the control and the vehicle, but showed that the expression ratio was concentration-dependently decreased to about 35%, about 21%, about 15%, and about 12%, respectively, in 5, 20, 50, and 100 μg/ml. In the docosenol (cis-13-Docosenol), the vehicle showed 100% expression ratio, but showed that the expression ratio was concentration-dependently decreased to about 41%, about 28%, and about 8%, respectively, in 5, 20, and 50 μg/ml. p-p38/p-38 ratio (%) of the nonadecanone (2-Nonadecanone) showed 19% and 100% expression ratio, respectively, in the control and the vehicle, but showed that the expression ratio was concentration-dependently decreased to about 75%, about 54%, about 42%, and about 29%, respectively, in 5, 20, 50, and 100 μg/ml. In the docosenol (cis-13-Docosenol), the control and the vehicle, respectively, showed 11% and 100% expression ratio, but showed that the expression ratio was concentration-dependently decreased to about 69%, about 48%, about 36%, and about 25%, respectively, in 5, 20, 50, 100 μg/ml.

<2-10> Measurement of Cytotoxicity of *Acer Tegmentosum Maxim* Extract

In order to examine the cytotoxicity of the *Acer tegmentosum maxim* extract on nerve cells, the BV-2 cells were treated in the group of conditioned medium for 48 hours, and the concentrated dry material of each *Acer tegmentosum maxim* material was treated at 8 concentrations of 10, 50, 100, 200, 300, 500, 600, and 800, and then the viability of microglial cells was measured by MTT assay.

Specifically, the MTT assay was carried out by measuring the cell viability effects using MTT [3-(4,5-dimethylthiazol-2-yl)-2,5-diphenyltetrazolium bromide), the absorbance was continuously measured at 540 nm using a microplate reader (Model 550, Bio-Rad, USA), and the results are shown in FIG. 22.

Referring to FIG. 22, it can be confirmed that the *Acer tegmentosum maxim* did not exhibit cytotoxicity to nerve cells at its concentration of 800 μg/mL or less.

<2-11> Measurement of DPPH Radical Scavenging Activity of *Acer Tegmentosum Maxim* Extract First, in order to measure DPPH radical scavenging activity of the *Acer tegmentosum maxim* extract, 1.9 ml of 0.2 mM DPPH solution (99.5% ethanol) was added to 0.1 ml of solutions (control: 99.5% ethanol) in which the concentrated dried material of each *Acer tegmentosum maxim* material was prepared at 7 concentrations of 10, 20, 40, 80, 160, 320 and 640 μg/ml, respectively. The mixture was shaken with a vortex mixer for 10 seconds and then incubated at 37° C. for 30 minutes. Then, the absorbance was measured at 517 nm using a spectrophotometer.

As a positive control, L-ascorbic acid was prepared at 6 concentrations of 10, 20, 40, 80, 160, 320, and 640 μg/mL (99.5% ethanol). The antioxidant activity of each sample was showed as % antioxidant activity (electron donating ability) against DPPH.

As a result, the ascorbic acid, which is a positive substance, was concentration-dependently increased as about 70.5%, about 71.8%, about 74.1%, about 77.8%, about 80.6%, about 83.2%, and about 84.5%, respectively, as the concentration was increased as 10, 20, 40, 80, 160, 320, and 640 μg/mL. It can be indicated that the anti-oxidation rate in the *Acer tegmentosum maxim* extract was concentration-dependently increased as the *Acer tegmentosum maxim* extract was about 5.1%, about 6.8%, about 15.5%, about 21.6%, about 25.5%, about 34.8%, and about 35.3% (See FIG. 23).

<2-12> Measurement of Xanthine Oxidase Inhibitory Activity of *Acer Tegmentosum Maxim* Extract The superoxide radical scavenging effects of 10, 20, 40, 80, 160, 320, and 640 μg mL-1 of the *Acer tegmentosum maxim* extract were compared using butylated hydroxy anisole (BHA) as a positive control group. BHA (butylated hydroxy anisole), which is a positive substance, was concentration-dependently increased to about 5.6%, about 8.2%, about 10.5%, about 22.1%, about 29.6%, about 31.6%, and about 32.1%, respectively, as the concentration was increased as 10, 20, 40, 80, 160, 320, and 640 μg/mL.

In addition, it can be confirmed that the effect of xanthine oxidase inhibition ratio was almost ⅓ times as compared with the positive control group (butylated hydroxy anisole, BHA) (See FIG. 24).

<2-13> Measurement of Cytotoxicity of *Berchemia* Berchemiaefolia Extract

In order to examine the cytotoxicity of the *berchemia berchemiaefolia* extract on nerve cells, the BV-2 cells were treated in the group of conditioned medium for 48 hours, and the concentrated dry material of each *berchemia berchemiaefolia* material was treated at 8 concentrations of 10, 50, 100, 200, 300, 500, 600, and 800, and then the viability of microglial cells was measured by MTT assay.

Specifically, the MTT assay was carried out by measuring the cell viability effects using MTT [3-(4,5-dimethylthiazol-2-yl)-2,5-diphenyltetrazolium bromide), the absorbance was continuously measured at 540 nm using a microplate reader (Model 550, Bio-Rad, USA), and the results are shown in FIG. 25.

Referring to FIG. 25, it can be confirmed that the *berchemia berchemiaefolia* extract did not exhibit cytotoxicity to nerve cells at its concentration of 800 μg/mL or less.

<2-14> Measurement of DPPH Radical Scavenging Activity of *Berchemia* Berchemiaefolia Extract First, in order to measure DPPH radical scavenging activity of the *berchemia berchemiaefolia* extract, 1.9 ml of 0.2 mM DPPH solution (99.5% ethanol) was added to 0.1 ml of solutions (control: 99.5% ethanol) in which the concentrated dried material of each *berchemia berchemiaefolia* material was prepared at 7 concentrations of 10, 20, 40, 80, 160, 320 and 640 μg/ml, respectively. The mixture was shaken with a vortex mixer for 10 seconds and then incubated at 37° C. for 30 minutes. Then, the absorbance was measured at 517 nm using a spectrophotometer.

As a positive control drug, L-ascorbic acid was prepared at 6 concentrations of 10, 20, 40, 80, 160, 320, and 640 μg/mL (99.5% ethanol). The antioxidant activity of each sample was showed as % antioxidant activity (electron donating ability) against DPPH.

As a result, the ascorbic acid, which is a positive substance, was concentration-dependently increased as about 70.5%, about 71.8%, about 74.1%, about 77.8%, about 80.6%, about 83.2%, and about 84.5%, respectively, as the concentration was increased as 10, 20, 40, 80, 160, 320, and 640 μg/mL. It can be indicated that the anti-oxidation rate in the *berchemia berchemiaefolia* extract was concentration-dependently increased as the *berchemia berchemiaefolia* extract was about 4.5%, about 5.2%, about 6.7%, about 11.5%, about 15.6%, about 17.8%, and about 18.4% (See FIG. 26).

<2-15> Measurement of Xanthine Oxidase Inhibitory Activity of *Berchemia* Berchemiaefolia Extract The superoxide radical scavenging effects of 10, 20, 40, 80, 160, 320, and 640 μg mL-1 of the *berchemia berchemiaefolia* extract were compared using butylated hydroxy anisole (BHA) as a positive control group. BHA (butylated hydroxy anisole), which is a positive substance, was concentration-dependently increased to about 3%, about 10.2%, about 13.5%, about 18.6%, about 22.5%, about 25.1%, and about 26.8%, respectively, as the concentration was increased as 10, 20, 40, 80, 160, 320, and 640 μg/mL. Further, it was showed that the effect of xanthine oxidase inhibition ratio was almost ⅓% as compared with the positive control group (butylated hydroxy anisole, BHA) (See FIG. 27).

<2-16> Measurement of Cytotoxicity of *Lithospermum Erythrorhizon* Extract

In order to examine the cytotoxicity of the *Lithospermum erythrorhizon* extract on nerve cells, the BV-2 cells were treated in the group of conditioned medium for 48 hours, and the concentrated dry material of each *Lithospermum erythrorhizon* material was treated at 8 concentrations of 10, 50, 100, 200, 300, 500, 600, and 800, and then the viability of microglial cells was measured by MTT assay.

Specifically, the MTT assay was carried out by measuring the cell viability effects using MTT [3-(4,5-dimethylthiazol-2-yl)-2,5-diphenyltetrazolium bromide), the absorbance was continuously measured at 540 nm using a microplate reader (Model 550, Bio-Rad, USA), and the results are shown in FIG. 28.

Referring to FIG. 28, it can be confirmed that the *Lithospermum erythrorhizon* extract did not exhibit cytotoxicity to nerve cells at its concentration of 800 μg/mL or less.

<2-17> Measurement of DPPH Radical Scavenging Activity of *Lithospermum Erythrorhizon* Extract First, in order to measure DPPH radical scavenging activity of the *Lithospermum erythrorhizon* extract, 1.9 ml of 0.2 mM DPPH solution (99.5% ethanol) was added to 0.1 ml of solutions (control: 99.5% ethanol) in which the concentrated dried material of each *Lithospermum erythrorhizon* material was prepared at 7 concentrations of 10, 20, 40, 80, 160, 320 and 640 μg/ml, respectively. The mixture was shaken with a vortex mixer for 10 seconds and then incubated at 37° C. for 30 minutes. Then, the absorbance was measured at 517 nm using a spectrophotometer.

As a positive control drug, L-ascorbic acid was prepared at 6 concentrations of 10, 20, 40, 80, 160, 320, and 640 μg/mL (99.5% ethanol). The antioxidant activity of each sample was showed as % antioxidant activity (electron donating ability) against DPPH.

As a result, the ascorbic acid, which is a positive substance, was concentration-dependently increased as about 70.5%, about 71.8%, about 74.1%, about 77.8%, about 80.6%, about 83.2%, and about 84.5%, respectively, as the concentration was increased as 10, 20, 40, 80, 160, 320, and 640 μg/mL. It can be indicated that the anti-oxidation rate in the *Lithospermum erythrorhizon* extract was concentration-dependently increased as the *Lithospermum erythrorhizon* extract was about 6.8%, about 11.2%, about 15.8%, about 28.5%, about 35.6%, about 37.1%, and about 40.1%, and the anti-oxidation rate was close to 50% at the highest concentration. (See FIG. 29).

<2-18> Measurement of Xanthine Oxidase Inhibitory Activity of *Lithospermum Erythrorhizon* Extract The superoxide radical scavenging effects of 10, 20, 40, 80, 160, 320, and 640 μg mL-1 of the *Lithospermum erythrorhizon* extract were compared using butylated hydroxy anisole (BHA) as a positive control group. BHA (butylated hydroxy anisole), which is a positive substance, was concentration-dependently increased to about 8.1%, about 11.8%, about 15.4%, about 20.1%, about 24.8%, and about 30.6%, respectively, as the concentration was increased as 10, 20, 40, 80, 160, 320, and 640 μg/mL. The positive control group (butylated hydroxy anisole, BHA) was 94.1% and the effect of xanthine oxidase inhibition ratio showed about ⅓ (See FIG. 30).

Example 3

Oral Administration and Analysis of *Fomes Fomentarius* Extract in Induced Depression Rat Model
<3-1> Test Subject
The experimental animals were 15 female Sprague-Dawley (SD) rats, 10 weeks old (220 g to 280 g) purchased from Oriental Biotech Corp. The feeding ground was maintained at a temperature of 25° C., a humidity of 50%, and 12-hour light/dark circulation. Purchased rats were allowed to adapt for a week after the transfer, and feed and drinking water were provided freely without limit.
<3-2> Production of *Fomes Fomentarius* Extract (FFE) Liquid
The *Fomes fomentarius* was ground with a grinder, mixed with 70% ethanol, and extracted with a rounded mixed machine for 18 hours. After the extraction, the extracts were filtered through a filter paper and centrifuged to collect the supernatant, which was then concentrated by evaporation in a bath at 40° C. The remaining material was repeated twice in the same manner and the yield ratio was 7.8%.
<3-3> Preparation of Depression-Induced Rat Model
As an animal model for induction of depression, the animal was subject to Forced Swimming Test (FST) in which the animal attempted to escape in the early stage, but the animal was forced to give up its over time to be in frustration and then to measure the immobility time. Specifically, the depression-induced model used in the test employed a method used by Detke et al. [Detke M J, Rickels M, Lucki I (1995). Psychopharm 121: 66-72]. For this purpose, the forced swimming was performed to be adapted such that a glass cylinder having a height of 50 cm and a diameter of 25 cm was filled with water at 23° C., and for 15 minutes, the rat was dropped in the water 24 hours to perform FST before the experiment in order for the rat's adaptation. Behavioral testing was performed on each of the 1st and 5th days of oral administration of the drug to evaluate the acute effects and moderate chronic effects of the drugs.
The experiment was performed in a method described in FIG. 31. The experiment was performed in that the experimental groups were divided into ① Group I: normal group (n=3), ② Group II: depression-induced group (n=3), ③ Group III: depression+100 mg/kg of *Fomes fomentarius* extract orally administered group (n=3), ④ Group IV: depression+25 mg/kg of *Fomes fomentarius* extract orally administered group (n=3), and ⑤ Group V: depression+10 mg/kg of tianeptine sodium orally administered group (n=3, positive control group). Specifically, in order to see acute effects of the *Fomes fomentarius* extract 24 hours later, the *Fomes fomentarius* extract and tianeptine sodium were orally administered alternately, and then the forced swimming test (FST) was carried out for 5 minutes after having the absorption time of 30 minutes. Immediately after the forced swimming test, the Y-maze test was performed for 3 minutes. In order to confirm moderate chronic effects, behavioral response tests were performed by oral administration of the *Fomes fomentarius* extract and tianeptine sodium 5 times for 5 days in the same way. After the measurement of the behavioral response, the animals were inhaled with ether and anesthetized, and then the medulla oblongata and the adrenal gland were immediately removed from the rats and stored at 70° C.

<3-4> Analysis Method
(1) Measurement of Time of Immobility on Forced Swimming Test
The rat's behavior for 5 minutes was classified into the immobility, climbing, and swimming, and thus measured the time of the immobility except the climbing and swimming. The immobility time measurement was performed 30 minutes after oral administration of the *Fomes fomentarius* extract and tianeptine sodium and performed on each of the 1st and 5th days of oral administration of the drug to evaluate the acute effects and moderate chronic effects of the drugs.
(2) Measurement of Total Number of Entries and Total Travel Distance of Y-Maze
Immediately after the immobility time measurement, the Y-maze test was performed for 3 minutes. The total number of times in which the rats in each group entered the three arms were compared between the groups, and the total distance traveled by the rats in the maze was statistically analyzed to analyze the difference between the groups. In order to evaluate acute and chronic effects as well as immobility time measurement, the study was carried out on the 1st and 5th day of drug administration.
(3) Quantitative Analysis of Protein
After the drug was orally administered to rats for 5 days and then the behavioral tests were performed, the rats were immediately sacrificed and the medulla oblongata and the adrenal gland were extracted. The appropriate amount of lysis buffer (PRO-Prep™, protein extraction solution) was added according to an amount of the tissue. They were homogenized evenly with a homogenizer (Intron Biotechnology, Gyeonggi-do, Korea) and were centrifuged at 4° C., 13,000 rpm using a centrifuge (Hanil Science, Korea) for 10 minutes to obtain a cell extract. The total protein content was determined by measuring the absorbance of the cell extracts at 595 nm using the Bio-Rad Protein Assay Kit (Bio-Rad Hercules, Calif., USA) by Bradford method. Each sample was quantitated with equivalent amount of protein, heated at 95° C. for 10 minutes, cooled at 20° C. for 3 minutes. After 18.5 µl of sample was loaded in each well with 10% to 12% sodium dodecyl sulfate-polyacrylamide gel, an electrophoresis was performed at 70 V for 30 minutes, at 100 V for 1 hour and 30 minutes, and at 110 V for 1 hour and 40 minutes. The electrophoresed proteins were transferred to a nitrocellulose membrane under refrigeration at 100 V for 1 hour and 30 minutes. To confirm the transfer of protein, the cells were stained with Ponceau solution and blocked twice with 5% skim milk for 1 hour. The primary antibodies iNOS, Nrf2, and β-actin were diluted to 1:500, 1:500, and 1:4000, respectively, and reacted at 4° C. for 24 hours. The cells were washed 5 times with 1×PBST (10×PBST, DW, 0.1% Tween 20) once every 7 minutes. Secondary antibody (rabbit, mouse) was reacted for 2 hours according to the primary antibody species, and was washed in the same method. ECL prime (Amersham Pharmacia Biotech, Buckinghamshire, UK) was used to measure and analyze the amount of protein expression in the dark.
(4) Statistical Processing
The forced swimming test immobility time and Y-maze total travel distance were analyzed by ANOVA using SPSS Version 18. Protein quantification results were quantified using Vision Works Image Software and analyzed with ANOVA.

(5) Analysis Result

1. Measurement Result of Immobility Time of Forced Swimming Test

FIG. 32 shows the decrease in the immobility time according to the oral administration of the *Fomes fomentarius*. Referring to this, in the acute effect, the *Fomes fomentarius* extract orally administered groups (100 mg/kg and 25 mg/kg) showed significant decreases in immobility time (p<0.01) compared to FST induced group. In the chronic effect, the *Fomes fomentarius* extract orally administered group (25 mg/kg) showed a significant decrease (p<0.05). Excellent effect of immobility time decrease was showed in acute than chronic.

2. Measurement Result of Total Number of Entry and Total Travel Distance in Y-Maze FIG. 33 shows the results of the mobility evaluation according to the total number of entries and the total movement distance in the Y-maze. Referring to this, the total number of entries was increased by 3 times in the FST-induced group and 5 times and 4 times, respectively, in 100 and 25 mg/kg of the *Fomes fomentarius* extract administered groups in the acute effect, and showed similar elevation effect compared to that of the positive control group. The chronic effect also showed an increase in the number of entries. In the acute effect, total travel distance was significantly increased (p<0.05) in 25 mg/kg of the *Fomes fomentarius* extract administered group. In the chronic effect, both of 100 mg/kg and 25 mg/kg of the *Fomes fomentarius* extract administered groups were significantly increased compared to FST induced group (p<0.01). It is determined that the overall increases in the number of entries and in travel distance of the acute and chronic effects are due to the adaptation of repeated experiments.

3. Result of Quantitative Analysis of Protein

FIG. 34 shows the analysis results of expression of signal transmission proteins in medulla oblongata and adrenal glands. Referring to this, it can be firstly shown that iNOS expression of Group II was surely increased than that of Group I and iNOS expression of Group III was significantly decreased than that of Group II (p<0.01), and Nrf2 also showed same patterns as iNOS regarding expression of iNOS and Nrf2, inflammatory regulation and anti-oxidative signal transmission proteins, of the *Fomes fomentarius* extract in the medulla oblongata. Further, regarding expression of iNOS and Nrf2 of the *Fomes fomentarius* extract in the adrenal glands, the expression of iNOS was significantly reduced in Group IV compared to Group II (p<0.05), and the expression of Nrf2 was significantly reduced in Group III (p<0.01).

Example 4

Oral Administration and Analysis of *Lithospermum Erythrorhizon* Extract in Induced Depression Rat Model <4-1> Test Subject The experiment was carried out in the same manner as in Example 1, except that 15 female rats of five weeks old (100 g to 130 g) were used as test subjects.

<4-2> Preparation of *Lithospermum Erythrorhizon* Extract Liquid

The *Lithospermum erythrorhizon* was ground with a grinder, mixed with 70% ethanol, and extracted with a rounded mixed machine for 18 hours. After the extraction, the extracts were filtered through a filter paper and centrifuged to collect the supernatant, which was then concentrated by evaporation in a bath at 40° C. The remaining material was repeated twice in the same manner and the yield ratio was 8.8%.

<4-3> Preparation of Depression Induced Rat Model

The same procedure as in Example 1 was conducted except that the *Lithospermum erythrorhizon* extract was used, and the experimental group were divided into ① Group I: normal group (n=3), ② Group II: depression-induced group (n=3), ③ Group III: depression+100 mg/kg of *Lithospermum erythrorhizon* extract orally administered group (n=3), ④ Group IV: depression+25 mg/kg of *Lithospermum erythrorhizon* extract orally administered group (n=3), and ⑤ Group V: depression+10 mg/kg of tianeptine sodium orally administered group (n=3, positive control group).

<4-4> Analysis Method

The immobility time measurement analysis of forced swimming test, total number of entries and total travel distance measurement analysis of Y-maze, and protein quantitative analysis were carried out as the same procedure as in Example 3, except that the *Lithospermum erythrorhizon* extract was used.

<4-5> Analysis Result (1) Measurement Result of Immobility Time of Forced Swimming Test FIG. 35 shows the decrease in the immobility time according to the oral administration of the *Lithospermum erythrorhizon* extracts. Referring to this, showed was the effects that immobility time was significantly lowered in both acute and moderate chronic effects compared to the control group. The same reduction effect was shown in comparison with the positive control, and the immobility time reduction effect was better in chronic than acute.

(2) Measurement Result of Total Number of Entry and Total Travel Distance in Y-Maze FIG. 36 shows the results of the mobility evaluation according to the total number of entries and the total movement distance in the Y-maze. Referring to this, the total number of entries was significantly increased by 3 times in the FST-induced group and 15 times and 16 times, respectively, in 100 and 25 mg/kg of the *Lithospermum erythrorhizon* extract administered groups in the acute effect, and show excellent elevation effect compared to that of the positive control group. The chronic effect also showed an excellent increase in the number of entries. In the total travel distance, there was a tendency that the *Lithospermum erythrorhizon* extract administered group was higher than the control group. However, the total number of entries in the Y-maze showed an increase in mobility compared to the control group, but the total travel distance showed a tendency to increase compared to the control group, but no significant results were seen because of the large error range between individuals.

(3) Result of Quantitative Analysis of Protein

FIG. 37 shows the analysis results of expression of signal transmission proteins in medulla oblongata and adrenal glands.

Referring to this, it can be firstly shown that iNOS and Nrf2 expressions of Group II were surely increased than that of Group I, iNOS expression of Group III was significantly decreased than that of Group II (p<0.01), and Nrf2 expression of Group IV showed a pattern of a significant decrease compared with Group II (p<0.05), regarding expression of iNOS and Nrf2, inflammatory regulation and anti-oxidative signal transmission proteins of the *Lithospermum erythrorhizon* extract in the medulla oblongata.

Further, in the adrenal glands, the expressions of iNOS and Nrf2 were significantly reduced in the *Lithospermum erythrorhizon* extract administered group compared to the control group, and in particular, the expression of Nrf2 was significantly reduced in Group III (p<0.01).

Example 5

Oral Administration and Analysis of Mixture of *Fomes Fomentarius/Lithospermum Erythrorhizon* Extracts in Induced Depression Rat Model
<5-1> Analysis Method
The immobility time measurement analysis of forced swimming test and protein quantitative analysis were carried out as the same procedure as in Example 3, except that a mixture of the *Fomes fomentarius* extract and *Lithospermum erythrorhizon* extract was used.

It was carried out that the ratio of the mixture of the *Fomes fomentarius* extract and *Lithospermum erythrorhizon* extract was 4:1.
<5-2> Analysis Result
(1) Measurement Result of Immobility Time of Forced Swimming Test
FIG. 38 shows the measurement result of the immobility time on the oral administration of the mixture of the *Fomes fomentarius* extract and *Lithospermum erythrorhizon* extract. Referring to this, showed was the effects that immobility time was significantly lowered in both acute and chronic effects compared to the control group. The same reduction effect was shown in comparison with the positive control, and the immobility time reduction effect was better in chronic than acute.
(2) Result of Quantitative Analysis of Protein
FIG. 39 shows the analysis results of expression of signal transmission proteins in medulla oblongata on the oral administration of the mixture of the *Fomes fomentarius* extract and *Lithospermum erythrorhizon* extract.

Referring to this, regarding expression of iNOS and Nrf2, inflammatory regulation and anti-oxidative signal transmission proteins, it can be shown that iNOS and Nrf2 expressions of the vehicle group were surely increased than that of the control group, iNOS and Nrf2 expressions of both of the *Fomes fomentarius* extract administered group and the *Lithospermum erythrorhizon* extract administered group were significantly decreased than that of the vehicle group, and in particular, iNOS and Nrf2 expressions of the mixture of the *Fomes fomentarius* extract and *Lithospermum erythrorhizon* extract administered group showed a pattern of a certain decrease. Although this is compared with the *Fomes fomentarius* extract administered group and the *Lithospermum erythrorhizon* extract administered group having small reduction of iNOS expression, such expression amount showed a significant reduction, and it was thus determined that the effect of controlling expressions of iNOS and Nrf2, inflammatory regulation and anti-oxidative signal transmission proteins was excellent in the mixture of the *Fomes fomentarius* extract and *Lithospermum erythrorhizon* extract administered group.

As described above, in the present example, anti-depressant effect of the *Fomes fomentarius* extract was evaluated by measuring immobility time which indicates a frustrated state in the depression induced rat model through the forced swimming test (FST), evaluating mobility after depression induction through the Y-maze test, and comparing and measuring expressions of iNOS and Nrf2, inflammatory regulation and anti-oxidative signal transmission proteins, in the medulla oblongata and the adrenal gland. As a result, the immobility time was significantly decreased in the *Fomes fomentarius* extract administered group, and the total number of entries and total travel distance also showed a significant increase compared to the forced swimming test induced group. Expressions of iNOS and Nrf2 were also significantly decreased. These results suggest that the *Fomes fomentarius* extract has anti-depressive effects of the regulation of inflammatory response and anti-stress by inhibiting the expressions of iNOS and Nrf2, signal transmission proteins.

In addition, the same evaluation was also carried out on the *Lithospermum erythrorhizon* extract. The results showed decrease of immobility time, increase of total number of entries and travel distance, and decrease of expressions of iNOS and Nrf2 in the *Lithospermum erythrorhizon* extract orally administered group compared to the forced swimming test induced group. These results suggest that the oral administration of the *Lithospermum erythrorhizon* extract as well as the *Fomes fomentarius* extract inhibits the expressions of iNOS and Nrf2 to have anti-depressive effects of the regulation of inflammatory response and anti-stress.

In addition, as results of measuring the immobility time and comparing and measuring the expression of iNOS and Nrf2 in inflammatory and anti-oxidative signal transmission proteins in the medulla oblongata for the mixture of the *Fomes fomentarius* extract and *Lithospermum erythrorhizon* extract, in particular, shown were decrease of immobility time as well as significant reduction of the expressions of iNOS and Nrf2 on the oral administration of the mixture of the *Fomes fomentarius* extract and *Lithospermum erythrorhizon* extract compared to each single extract administration.

Therefore, it can be concluded from the results of this example that the *Fomes fomentarius* extract and *Lithospermum erythrorhizon* extract of the present disclosure can exhibit anti-stress and anti-psychotic effects by control of the inflammatory response and anti-oxidative function in the mental disorder including depression.

Example 6

Oral Administration and Analysis of *Berchemia Berchemiaefolia* Extract in Induced Depression Rat Model
<6-1> Test Subject
The experimental animals were 20 female Sprague-Dawley (SD) family rats, 4 weeks old (150 g to 170 g) purchased from Korean Central Animal. The feeding ground was maintained at a temperature of 20±2° C., a humidity of 55% to 60%, and 12-hour light/dark circulation. Purchased rats were allowed to adapt for a week after the transfer, and feed and drinking water were provided freely without limit.
<6-2> Preparation of *Berchemia* Berchemiaefolia Extract
*Berchemia* berchemiaefolia root was purchased from Pharmtekbio in Busan. The complete dried *berchemia* berchemiaefolia root was finely crushed using a crusher and lyophilized. 2 g of the lyophilized sample and 10 mL of 70% ethanol were placed in a 15 mL tube and dissolved in a mixer for 18 hours, followed by centrifugation at 3000 rpm to collect only supernatant. The collected supernatant was evaporated at high temperature and the remaining sample was concentrated and lyophilized. The *berchemia* berchemiaefolia samples used in the present experiment were extracted with 6.3% yield ratio from *berchemia* berchemiaefolia raw materials.

<6-3> Preparation of Depression-Induced Rat Model

The first forced swimming test (FST) was carried out for 15 minutes after having the incubator environmental adaptation for one week.

24 hours later, the second FST experiment was performed for 5 minutes. 30 minutes before the experiment, the *berchemia* berchemiaefolia extract was put in the experimental group according to the determined dose. The *berchemia* berchemiaefolia extract was orally administered once a day for 5 days. Animals were sacrificed immediately after the last FST experiment was carried out for 5 minutes. The day before sacrifice was fasted and water was supplied well. Immediately after the last FST experiment, blood was collected over 6 ml from the abdominal vein after ether anesthesia. The blood collected from the abdominal vein was stored in a 5 ml SST tube. SST tube blood specimens were centrifuged at 3000 rpm for 15 min and then the serum was stored in an E-tube at −70° C. Tissue from brain, medulla oblongata, and adrenal gland was removed by perfusion with saline solution through the ascending aorta. The specimens were transferred to an E-tube and stored at −70° C. until homogenization.

The test was carried out such that the experimental group was divided into ① Group I: normal group (n=5), ② Group II: forced swimming test group (n=5), ③ Group III: forced swimming test+86 mg/kg of *berchemia* berchemiaefolia extract orally administered group (n=5), and ④ Group IV: forced swimming test+256 mg/kg of *berchemia* berchemiaefolia extract orally administered group (n=5).

<6-4> Analysis Method

The *berchemia* berchemiaefolia extract was used, and immobility time measurement analysis of the forced swimming test and protein quantitative analysis were performed as in Example 3. Analysis of liver function markers and inflammatory markers and analysis of cytokines and hormones were further carried out.

(1) Analysis of Liver Function Marker and Inflammatory Marker

In order to confirm the toxicity of the *berchemia* berchemiaefolia extract, aspartate aminotransferase (AST), alanine aminotransferase (ALT), and alkaline phosphatase (ALP), which are liver markers in plasma, were measured by ECLIA (Chemiluminescence immunoassay) principle using a Cobas 6000 analyzer series (Roche Diagnostics, Switzerland) device. The high sensitivity C-reactive protein, an inflammatory marker, was measured by the ECLIA principle using a HITACHI 7600-210 (Hitachi, Japan) instrument.

(2) Analysis of Cytokine and Hormone

IL-6, TNF-α, and IL-1β were measured using an ELISA kit (R&D systems, America).

Serum cortisol and adrenocorticotropic hormone (ACTH) concentrations were measured by the ECLIA principle using the Beckman Coulter AU5800 Chemistry system (Bechman Coulter, America) instrument.

<6-5> Analysis Result (1) Measurement Result of Immobility Time of Forced Swimming Experiment FIG. 40 shows the decrease in the immobility time according to the oral administration of the *berchemia* berchemiaefolia extract. Referring to this, Group III and Group IV showed a significant decrease compared to the control group (Group II) (P<0.05). Compared the second forced swimming test (A) and the forced swimming test (B) just before the animal sacrifice, the control groups showed 144 seconds and 138 seconds, respectively, which were similar, but the high concentration (256 mg/kg) the *berchemia* berchemiaefolia extract oral administered groups showed 71±11.4 seconds and 68±8.7 seconds, respectively, which indicated a large difference.

(2) Analysis of Liver Function Marker and Inflammatory Marker

Table 2 below shows liver damage markers and CRP concentration evaluation results. Referring to this, there was no significant difference in liver function markers (ALT, AST, and ALP) from the control group (p>0.05). Concentrations of high sensitive C proteins (hS-CRP) were also not significantly different from the test groups (p>0.05).

TABLE 2

| Var- | Group | | | |
| iable | I | II | III | IV |
|---|---|---|---|---|
| ALP (IU/L) | 141.1 ± 3.9 | 150.3 ± 8.9 | 148.1 ± 9.1 | 151.9 ± 7.7 |
| ALT (IU/L) | 50.1 ± 8.1 | 49.4 ± 7.6 | 41.2 ± 6.8 | 55.7 ± 10.2 |
| AST (IU/L) | 70.1 ± 13.6 | 74.6 ± 9.8 | 71.9 ± 11.6 | 73.2 ± 12.2 |
| hS-CRP (ng/mL) | 7.1 ± 1.8 | 8.9 ± 4.2 | 6.1 ± 3.9 | 8.1 ± 1.8 |

Data are expressed ±SD.

(3) Analysis Result of Cytokine and Hormone

The results of the cytokine (A) IL-1β, (B) IL-6 (C) TNF-α concentration analysis between the groups are shown in FIG. 41.

Referring to this, there was a significant difference in IL-1β between the experimental groups (Group III and Group IV: 105.7±10.5 and 72.8±9.8) and Group II (vehicle), and thus the concentration of IL-1β was significantly reduced in Group III and Group IV compared to Group II (162.8±15.9) (P<0.05), and Group I showed 34.7±21.9 which was the lowest. IL-6 showed the same tendency as IL-1β. In this case, the values of Group I, Group II, Group III, and Group IV, respectively, showed 76.0±39.8, 551.6±28.1, 124.8±17.9, 116.9±24.1, and there was a statistically significant difference between Group II and the other Groups (p<0.05). Regarding TNF-α, a result of Group II also showed the highest (199.7±38.2) and there was a significant difference compared to the other groups (p<0.05).

Table 3 below shows the evaluation results of the cortisol and ACTH concentrations as a result of hormone analysis. Referring to this, the concentration of cortisol was the highest in Group II, and the result of adrenocorticotrophic hormone (ACTH) also showed the highest concentration in Group II.

TABLE 3

| Var- | Group | | | |
| iable | I | II | III | IV |
|---|---|---|---|---|
| Cortisol (ng/mL) | 62.1 ± 12.9 | 245.1 ± 39.1 | *122.1 ± 25.3 | *109.1 ± 18.1 |
| ACTH (pg/mL) | 38.1 ± 6.8 | 61.9 ± 17.8 | 21.9 ± 6.8 | 19.9 ± 10.9 |

Data are expressed ±SD.
*P <0.05 compared with Group II.

(4) Quantitative Analysis Result of Protein

Tissue of adrenal gland, medulla oblongata, and brain were quantitatively analyzed by Western blotting, and the results are shown in FIG. 42, which is indicated in terms of the ratio of p-p65/total p65.

Referring to FIG. 42(A), in the adrenal gland, the *berchemia* berchemiaefolia extract non-administered group (Group II, 1.73) showed about twice the activity as the control group (Group I, 0.86), and it was observed that there was a pattern of sharp decrease in the Group IV (0.375), the high concentration *berchemia* berchemiaefolia extract administered group compared to the control group.

Referring to FIGS. 42(B) and 42(C), the medulla oblongata (B) and the brain (C) showed a tendency similar to the adrenal gland, and thus, the *berchemia* berchemiaefolia extract non-administered group showed improved activity compared to the control group. Specifically, in the medulla oblongata (3.15/0.49) and the brain (1.15/0.30), respectively, the *berchemia* berchemiaefolia extract non-administered group showed 6.42 times and 3.83 times higher activity than the control group. Similarly, it was confirmed that p-p65 expression was sharply decreased in the high concentration *berchemia* berchemiaefolia extract administered group.

Example 7

Oral Administration and Analysis of Mixture of *Fomes Fomentarius*/*Berchemia* Berchemiaefolia Extracts in Induced Depression Rat Model <7-1> Analysis Method The immobility time measurement analysis of forced swimming test and protein quantitative analysis were carried out as the same procedure as in Example 3, except that a mixture of the *Fomes fomentarius* extract and *berchemia* berchemiaefolia extract was used. It was carried out that the ratio of the mixture of the *Fomes fomentarius* extract and *berchemia* berchemiaefolia extract was 4:1.

<7-2> Analysis Result (1) Measurement Result of Immobility Time of Forced Swimming Test FIG. 43 shows the measurement result of the immobility time of forced swimming test on the oral administration of the mixture of the *Fomes fomentarius* extract and *berchemia* berchemiaefolia extract. Referring to this, showed was the effects that immobility time was significantly lowered in both acute and chronic effects compared to the control group. The same reduction effect was shown in comparison with the positive control, and the immobility time reduction effect in chronic was similar to that in acute.

(2) Result of Quantitative Analysis of Protein

FIG. 44 shows the analysis results of expression of signal transmission proteins in medulla oblongata on the oral administration of the mixture of *Fomes fomentarius* extract and *berchemia* berchemiaefolia extract.

Referring to this, regarding expression of iNOS and Nrf2, inflammatory regulation and anti-oxidative signal transmission proteins, it can be shown that iNOS and Nrf2 expressions of the vehicle group were surely increased than that of the control group, iNOS and Nrf2 expressions of both of the *Fomes fomentarius* extract administered group and the *berchemia* berchemiaefolia extract administered group were significantly decreased than that of the vehicle group, and in particular, Nrf2 expression of the mixture of the *Fomes fomentarius* extract and *berchemia* berchemiaefolia extract administered group showed a pattern of a certain decrease. It was determined that the effect of controlling expressions of iNOS and Nrf2, inflammatory regulation and anti-oxidative signal transmission proteins was excellent in the mixture of the *Fomes fomentarius* extract and *berchemia* berchemiaefolia extract administered group.

As described above, in the present example, anti-depressant effect of the *Fomes fomentarius* extract was evaluated by measuring immobility time which indicates a frustrated state in the depression induced rat model through the forced swimming test (FST), evaluating mobility after depression induction through the Y-maze test, and comparing and measuring expressions of iNOS and Nrf2, inflammatory regulation and anti-oxidative signal transmission proteins, in the medulla oblongata and the adrenal gland. As a result, the immobility time was significantly decreased in the *Fomes fomentarius* extract administered group, and the total number of entries and total travel distance also showed a significant increase compared to the forced swimming test induced group. Expressions of iNOS and Nrf2 were also significantly decreased. These results suggest that the *Fomes fomentarius* extract has anti-depressive effects of the regulation of inflammatory response and anti-stress by inhibiting the expressions of iNOS and Nrf2, signal transmission proteins.

In addition, in the case of the *berchemia* berchemiaefolia extract, the liver function test and hS-CRP were performed to confirm the presence of cytotoxicity of the natural product itself and the fact that there was no specific inflammation in rats before the experiment. As a result, it was confirmed that there was no significant difference between the control group and the experimental group and that the result of the forced swimming test showed a decrease in immobility time. Further, it was confirmed that IL-1β, IL-6 and TNF-α, NFκ-B signal transmission-related cytokines, were abruptly reduced in the *berchemia* berchemiaefolia extract administered group. It is presumed that the *berchemia* berchemiaefolia extract acted as an inhibitor against acute inflammatory reaction. In addition, hormone analysis showed that the cortisol secretion was significantly decreased in the *berchemia* berchemiaefolia extract administered group compared with the non-administered group, and the ACTH concentration was maintained in a proper manner. It was anticipated that the *berchemia* berchemiaefolia extract had positive effects that not only reduced stress hormones by lowering the concentration of excess secreted cortisol, but also helped maintain HPA axis feedback. Further, the presence or absence of NFκ-B expression was evaluated by the analysis of phosphorylated p65 (p-p65). As a result, the rapid p-p65 expression inhibition effect was observed in the *berchemia* berchemiaefolia administered group, especially the high concentration administered group. It was confirmed that the high concentration of the *berchemia* berchemiaefolia extracts was more effective for the down-regulation of NFκ-B expression compared to the low concentration. When these results were incorporated, it was determined that the *berchemia* berchemiaefolia extract may have the effect of anti-psychotic disorder by acting as NFκ-B phosphorylation inhibitor by anti-inflammatory regulatory mechanism.

In addition, as results of measuring the immobility time and comparing and measuring the expression of iNOS and Nrf2 in inflammatory and anti-oxidative signal transmission proteins in the medulla oblongata for the mixture of the *Fomes fomentarius* extract and *berchemia* berchemiaefolia extract, in particular, the immobility time was decreased, and the expressions of iNOS and Nrf2 were significantly reduced by the oral administration of the mixture of the *Fomes fomentarius* extract and *berchemia* berchemiaefolia extract, and further the expression of iNOS was significantly reduced compared to each single extract administration.

Therefore, it can be concluded from the results of this example that the *Fomes fomentarius* extract and *berchemia* berchemiaefolia extract of the present disclosure can exhibit anti-stress and anti-psychotic effects by control of the inflammatory response and anti-oxidative function in the mental disorder including depression.

Example 8

Oral Administration and Analysis of *Acer Tegmentosum Maxim* Extract in Induced Depression Rat Model <8-1> Test Subject The experimental animals were 25 female Sprague-Dawley (SD) family rats, 4 weeks old (150 g to 170 g) purchased from Korean Central Animal. The feeding ground was maintained at a temperature of 20±2° C., a humidity of 55% to 60%, and 12-hour light/dark circulation. Purchased rats were allowed to adapt for a week after the transfer, and feed and drinking water were provided freely without limit.

<8-2> Preparation of *Acer Tegmentosum Maxim* Extract

*Acer tegmentosum maxim* bark was purchased from Pharmtekbio in Busan. The *Acer tegmentosum maxim* was washed with water, was dried under the shade for 1 week or more, and was finely crushed using a crusher and lyophilized. 2 g of the lyophilized sample and 10 mL of 70% ethanol were placed in a 15 mL tube and dissolved in a mixer for 18 hours, followed by centrifugation at 3000 rpm to collect only supernatant. The collected supernatant was evaporated at a temperature of 40° C. and the remaining sample was concentrated and lyophilized. The *Acer tegmentosum maxim* samples used in the present experiment were extracted with 10.1% yield ratio from *Acer tegmentosum maxim* raw materials.

<8-3> Preparation of Depression-Induced Rat Model

The first forced swimming test (FST) was carried out for 15 minutes after having the incubator environmental adaptation for one week.

24 hours later, the second FST experiment was performed for 5 minutes. 30 minutes before the experiment, the *Acer tegmentosum maxim* extract was put in the experimental group according to the determined dose. The *Acer tegmentosum maxim* extract was orally administered once a day for 5 days. Animals were sacrificed immediately after the last FST experiment was carried out for 5 minutes. The day before sacrifice was fasted and water was supplied well. Immediately after the last FST experiment, blood was collected over 6 cc from the abdominal vein after ether anesthesia. The blood collected from the abdominal vein was stored in a 1 cc EDTA tube and 5 cc SST tube. EDTA tube blood specimens were analyzed within 1 hour, and SST tube blood specimens were centrifuged at 3000 rpm for 15 min and then the serum was stored in an E-tube at −70° C.

The test was carried out such that the experimental group was divided into ① Group I: normal group (n=5), ② Group II: forced swimming test group (n=5), ③ Group III: forced swimming test+400 mg/kg of *Acer tegmentosum maxim* extract orally administered group (n=5), ④ Group IV: forced swimming test+200 mg/kg of *Acer tegmentosum maxim* extract orally administered group (n=5), and ⑤ Group V: forced swimming test+100 mg/kg of *Acer tegmentosum maxim* extract orally administered group (n=5).

<8-4> Analysis Method

The *Acer tegmentosum maxim* extract was used, and immobility time measurement analysis of the forced swimming test was performed as in Example 3. Hematologic analysis, analysis of liver function markers and inflammatory markers, and analysis of cytokines and hormones were further carried out.

(1) Hematologic Analysis

The whole blood collected in the EDTA-tube was analyzed for the distribution of erythrocytes and leukocytes using LC-600 (HORIBA, Japan).

<8-5> Analysis Result (1) Measurement Result of Immobility Time of Forced Swimming Experiment FIG. 45 shows the decrease in the immobility time according to the oral administration of the *Acer tegmentosum maxim* extract. All experimental groups (Group III, Group IV, and Group V) showed significant decreases ($p<0.05$) compared to the control group (Group II) whose immobility time was 100 seconds or more. In particular, compared the second forced swimming test (A) and the forced swimming test just before the animal sacrifice (B), the control groups (Group II) showed 112±5.9 seconds and 105±8.6 seconds, respectively, which were similar, but the high concentration (400 mg/kg) the *Acer tegmentosum maxim* extract oral administered groups (Group III) showed 32±1.9 seconds and 67±7.0 seconds, respectively, which indicated a large difference.

(2) Analysis Result of Hematological Variables

The evaluation results of hematological marker concentration are shown in Table 4 below. Referring to this, there was no significant change in the blood level of all rat groups and all of them showed distribution within normal range. The absolute value of leukocyte of the *Acer tegmentosum maxim* extract not-administered group tended to be higher than that of Group II, which contained the *Acer tegmentosum maxim* extract, but there was no significant difference ($p>0.05$).

TABLE 4

| Variable | Group | | | | |
|---|---|---|---|---|---|
| ($\times 10^2/mm^3$) | I | II | III | IV | V |
| Erythrocyte ($\times 10^4/mm^3$) | 541.3 ± 18.1 | 551.7 ± 23.6 | 593.1 ± 19.4 | 584.3 ± 22.6 | 583.6 ± 22.7 |
| Lymphocye | 37.5 ± 4.6 | 41.3 ± 5.1 | 39.6 ± 5.9 | 36.7 ± 6.1 | 40.1 ± 4.8 |
| Neutrophil | 12.0 ± 3.5 | 15.3 ± 5.6 | 12.9 ± 3.1 | 13.4 ± 6.1 | 13.5 ± 4.9 |
| Monocyte | 3.9 ± 0.2 | 4.1 ± 1.0 | 3.9 ± 0.4 | 4.0 ± 0.7 | 3.8 ± 0.6 |
| Eosinophil | 1.6 ± 0.1 | 1.8 ± 0.5 | 2.1 ± 0.4 | 1.9 ± 0.2 | 1.9 ± 0.4 |
| Basophil | 2.4 ± 0.3 | 2.7 ± 0.4 | 2.9 ± 0.3 | 2.7 ± 0.5 | 2.7 ± 0.4 |

Data are expressed ±SD.

(2) Analysis of Liver Function Marker and Inflammatory Marker

Table 5 below shows liver damage markers and CRP concentration evaluation results. Referring to this, there was no significant difference in liver function markers (ALT, AST, and ALP) from the control group ($p>0.05$). Concentrations of high sensitive C proteins (hS-CRP) were also not significantly different from the test groups ($p>0.05$).

TABLE 5

| Variable | Group | | | | |
|---|---|---|---|---|---|
| | I | II | III | IV | V |
| ALP (IU/L) | 197.5 ± 4.6 | 179.5 ± 7.6 | 186.0 ± 3.6 | 191.5 ± 4.1 | 184.2 ± 5.6 |
| ALT (IU/L) | 41.2 ± 2.6 | 38.3 ± 1.9 | 40.8 ± 3.8 | 44.1 ± 5.1 | 38.7 ± 1.6 |
| AST (IU/L) | 81.6 ± 10.5 | 77.4 ± 8.6 | 88.1 ± 7.5 | 89.1 ± 6.9 | 90.1 ± 5.8 |
| hS-CRP (ng/mL) | 10.5 ± 0.4 | 11.4 ± 1.9 | 12.5 ± 1.6 | 10.8 ± 2.4 | 11.5 ± 1.4 |

Data are expressed ±SD.

(4) Analysis of Cytokine and Hormone

The results of the cytokine (A) IL-1β, (B) IL-6, and (C) TNF-α concentration analysis between the groups are shown in FIG. 46.

Referring to this, in the case of IL-1β, Group I was the lowest with 118.1±31.2, and Group II was the highest with 521.8±12.5. The experimental group, that is Group III, Group IV, and Group V were 275.2±58.1, 288.5±14.3, and 346.9±63.1, respectively, and the gap was significant and the difference was statistically significant compared to the vehicle (Group II) ($p<0.05$). IL-6 showed the same tendency as IL-1β. In this case, the values of Group I, Group II, Group III, and Group IV, respectively, were 85.6±21.8, 619.2±67.9, 321.8±39.8, 288.1±69.2, 376.8±42.5, and there was a statistically significant difference between Group II and the other groups ($p<0.05$). In the case of TNF-α, the result of Group II (174.8±23.5) was the highest, which was similar as above. Although there was a significant different from that of group IV (101.9±34.8) ($p<0.05$), there was no difference from the other groups ($p>0.05$).

Table 6 below shows the evaluation results of the cortisol and ACTH concentrations as a result of hormone analysis. Referring to this, the concentration of cortisol was the highest in Group II, and the result of adrenocorticotrophic hormone (ACTH) also showed the highest concentration in Group II.

TABLE 6

| Variable | Group | | | | |
|---|---|---|---|---|---|
| | I | II | III | IV | V |
| Cortisol (ng/mL) | 77.5 ± 10.4 | 379.5 ± 24.3 | *,286.0 ± 13.0 | *,141.5 ± 22.4 | *,184.2 ± 19.9 |
| ACTH (pg/mL) | 48.5 ± 7.1 | 51.5 ± 6.0 | 30.8 ± 7.8 | 34.1 ± 5.1 | 28.7 ± 11.6 |

Data are expressed ±SD.
*,P <0.05 compared with Group II.

Example 9

Oral Administration and Analysis of Mixture of *Fomes Fomentarius*/*Acer Tegmentosum Maxim* Extracts in Induced Depression Rat Model <9-1> Analysis Method The immobility time measurement analysis of forced swimming test and protein quantitative analysis were carried out as the same procedure as in Example 3, except that a mixture of the *Fomes fomentarius* extract and *Acer tegmentosum maxim* extract was used.

<9-2> Analysis Result (1) Measurement Result of Immobility Time of Forced Swimming Test FIG. 47 shows the measurement result of the immobility time on the oral administration of the mixture of the *Fomes fomentarius* extract and *Acer tegmentosum maxim* extract. Referring to this, showed was the effects that immobility time was significantly lowered in both acute and chronic effects compared to the control group. The same reduction effect was shown in comparison with the positive control, and the immobility time reduction effects were similar in chronic and acute.

(2) Result of Quantitative Analysis of Protein

FIG. 48 shows the analysis results of expression of signal transmission proteins in medulla oblongata on the oral administration of the mixture of the *Fomes fomentarius* extract and *Acer tegmentosum maxim* extract.

Referring to this, regarding expression of iNOS and Nrf2, inflammatory regulation and anti-oxidative signal transmission proteins, it can be shown that iNOS and Nrf2 expressions of the vehicle group were surely increased than that of the control group, iNOS and Nrf2 expressions of both of the *Fomes fomentarius* extract administered group and the *Acer tegmentosum maxim* extract administered group were significantly decreased than that of the vehicle group, and in particular, iNOS expression of the mixture of the *Fomes fomentarius* extract and *Acer tegmentosum maxim* extract administered group was certainly decreased. In high concentration mixture of the *Fomes fomentarius* extract and *Acer tegmentosum maxim* extract administered group, Nrf2 expression showed a pattern of a certain decrease. Therefore, it was determined that the effect of controlling expressions of iNOS and Nrf2, inflammatory regulation and anti-oxidative signal transmission proteins was excellent in the mixture of the *Fomes fomentarius* extract and *Acer tegmentosum maxim* extract administered group.

As described above, in the present example, anti-depressant effect of the *Fomes fomentarius* extract was evaluated by measuring immobility time which indicates a frustrated state in the depression induced rat model through the forced swimming test (FST), evaluating mobility after depression induction through the Y-maze test, and comparing and measuring expressions of iNOS and Nrf2, inflammatory regulation and anti-oxidative signal transmission proteins, in the medulla oblongata and the adrenal gland. As a result, the immobility time was significantly decreased in the *Fomes fomentarius* extract administered group, and the total number of entries and total travel distance also showed a significant increase compared to the forced swimming test induced group. Expressions of iNOS and Nrf2 were also significantly decreased. These results suggest that the *Fomes fomentarius* extract has anti-depressive effects of the regulation of inflammatory response and anti-stress by inhibiting the expressions of iNOS and Nrf2, signal transmission proteins.

In addition, in the case of the *Acer tegmentosum maxim* extract, the liver function test and hS-CRP were performed to determine the presence or absence of cytotoxicity of the natural product itself and the fact that there was no specific inflammation in rats before the experiment. As a result, it can be confirmed that there was no significant difference between the control group and the experimental group, and the immobility time in the forced swimming test was decreased. cyHerein, in particular, the concentration-dependent pattern was observed in single-dose oral administration, while low-concentration administration was more effective than high-concentration *Acer tegmentosum maxim* oral administration (400 mg/kg) in short and middle terms oral administration. Further, it was confirmed that IL-1β, IL-6 and TNF-α, NFκ-B signal transmission-related proinflammatory cytokines, were abruptly reduced in the *Acer tegmentosum maxim* extract administered group. In addition, hormone analysis showed that the cortisol secretion was significantly decreased in the *Acer tegmentosum maxim* extract administered group compared with the non-administered group, and the ACTH concentration was maintained in a proper manner. From this, it was anticipated that the *Acer tegmentosum maxim* extract not only reduced stress hormones by lowering the concentration of excess secreted cortisol, but also helped maintain HPA axis feedback. In particular, considering that both cytokine and cortisol contents were reduced, it was considered to have helped to maintain homeostasis of HPA-axis by increasing resistance to stress inflammation.

In addition, as results of measuring the immobility time and comparing and measuring the expression of iNOS and Nrf2 in inflammatory and anti-oxidative signal transmission proteins in the medulla oblongata for the mixture of the *Fomes fomentarius* extract and *Acer tegmentosum maxim* extract, in particular, the expressions of iNOS and Nrf2 were significantly reduced by the oral administration of the mixture of the *Fomes fomentarius* extract and *Acer tegmentosum maxim* extract, and further the expression of iNOS was significantly reduced compared to each single extract administration.

Therefore, it can be concluded from the results of this example that the *Fomes fomentarius* extract and *Acer tegmentosum maxim* extract of the present disclosure can exhibit anti-stress and anti-psychotic effects by control of the anti-inflammatory response and anti-oxidative function in the mental disorder including depression.

The invention claimed is:

1. A method for preventing or treating a cranial nerve disease comprising administering to a person in need thereof a pharmaceutical composition comprising a *Fomes fomentarius* extract, a fraction thereof, or a compound isolated therefrom as an active ingredient, wherein the cranial nerve disease is depression.

2. The method of claim 1, wherein the fraction is extracted with an ethyl acetate fraction, a hexane fraction, a chloroform fraction, or a butanol fraction.

3. The method of claim 1, wherein the compound is nonadecanone (2-Nonadecanone) or docosenol (cis-13-Docosenol).

4. The method of claim 1, further comprising administering an extract of one or more selected from the group consisting of *Berchemia* berchemiaefolia, *Acer tegmentosum maxim*, and *Lithospermum erythrorhizon*.

5. The method of claim 1, wherein the *Fomes fornentarius* extract, the fraction thereof, or the compound isolated therefrom inhibits production or expression of an inflammatory cytokine.

6. The method of claim 1, wherein the *Fomes fornentarius* extract, the fraction thereof, or the compound isolated therefrom improves glucose metabolism activity of a brain.

7. A method for preventing or improving a cranial nerve disease comprising administering to a person in need thereof a food composition comprising a *Fornes fomentarius* extract, a fraction thereof, or a compound isolated therefrom as an active ingredient, wherein the cranial nerve disease is depression.

8. The method of claim 7, wherein the fraction is extracted with an ethyl acetate fraction, a hexane fraction, a chloroform fraction, or a butanol fraction.

9. The method of claim 7, wherein the compound is nonadecanone (2-Nonadecanone) or docosenol (cis-13-Docosenol).

10. The method of claim 7, further comprising administering an extract of one or more selected from the group consisting of *Berchemia* berchemiaefolia, *Acer tegmentosum maxim*, and *Lithospermum erythrorhizon*.

* * * * *